(12) United States Patent
Beardsley et al.

(10) Patent No.: US 11,207,066 B2
(45) Date of Patent: Dec. 28, 2021

(54) APPARATUS FOR ENDOSCOPIC PROCEDURES

(71) Applicant: Covidien LP, Mansfield, MA (US)

(72) Inventors: John W. Beardsley, Wallingford, CT (US); David M. Farascioni, Bethel, CT (US)

(73) Assignee: COVIDIEN LP, Mansfield, MA (US)

( * ) Notice: Subject to any disclaimer, the term of this patent is extended or adjusted under 35 U.S.C. 154(b) by 173 days.

(21) Appl. No.: 16/158,427

(22) Filed: Oct. 12, 2018

(65) Prior Publication Data

US 2019/0125341 A1 May 2, 2019

Related U.S. Application Data

(60) Provisional application No. 62/578,673, filed on Oct. 30, 2017.

(51) Int. Cl.
*A61B 17/072* (2006.01)
*A61B 17/00* (2006.01)
*A61B 17/29* (2006.01)

(52) U.S. Cl.
CPC ...... *A61B 17/072* (2013.01); *A61B 17/00234* (2013.01); *A61B 17/07207* (2013.01); *A61B 17/29* (2013.01); *A61B 2017/00017* (2013.01); *A61B 2017/0046* (2013.01); *A61B 2017/00367* (2013.01); *A61B 2017/00398* (2013.01); *A61B 2017/00473* (2013.01); *A61B 2017/00477* (2013.01); *A61B 2017/00734* (2013.01); *A61B 2017/07257* (2013.01); *A61B 2017/07271* (2013.01); *A61B 2017/07278* (2013.01); *A61B 2017/07285* (2013.01); *A61B 2017/2901* (2013.01); *A61B 2017/2923* (2013.01);
(Continued)

(58) Field of Classification Search
CPC .............. A61B 17/07207; A61B 2017/07285
See application file for complete search history.

(56) References Cited

U.S. PATENT DOCUMENTS

| 37,165 A | 12/1862 | Gary |
| 3,079,606 A | 3/1963 | Bobrov et al. |
| 3,209,754 A | 10/1965 | Brown |

(Continued)

FOREIGN PATENT DOCUMENTS

| CN | 101683284 A | 3/2010 |
| CN | 102648864 A | 8/2012 |

(Continued)

OTHER PUBLICATIONS

European Search Report dated Jun. 28, 2019, issued in EP Appln. No. 18 20 3222.

(Continued)

*Primary Examiner* — Joshua G Kotis
(74) *Attorney, Agent, or Firm* — Carter, DeLuca & Farrell LLP

(57) ABSTRACT

A surgical stapling system includes a hand-held instrument, an adapter assembly, a pair of stapling reloads having end effectors, and a drive mechanism. The drive mechanism is longitudinally movable through one of the end effectors to fire staples therefrom. The drive mechanism extends through a support block positioned to move across a mounting member of the adapter assembly as the mounting member articulates the end effectors.

7 Claims, 43 Drawing Sheets

(52) U.S. Cl.
CPC .............. *A61B 2017/2926* (2013.01); *A61B 2017/2927* (2013.01)

(56) References Cited

U.S. PATENT DOCUMENTS

| | | |
|---|---|---|
| 3,273,562 A | 9/1966 | Brown |
| 3,490,675 A | 1/1970 | Green et al. |
| 3,499,591 A | 3/1970 | Green |
| 3,528,693 A | 9/1970 | Pearson et al. |
| 3,744,495 A | 7/1973 | Johnson |
| 3,862,631 A | 1/1975 | Austin |
| 3,949,924 A | 4/1976 | Green |
| 4,060,089 A | 11/1977 | Noiles |
| 4,204,623 A | 5/1980 | Green |
| 4,217,902 A | 8/1980 | March |
| 4,263,903 A | 4/1981 | Griggs |
| 4,275,813 A | 6/1981 | Noiles |
| 4,331,277 A | 5/1982 | Green |
| 4,428,376 A | 1/1984 | Mericle |
| 4,429,695 A | 2/1984 | Green |
| 4,444,181 A | 4/1984 | Wevers et al. |
| 4,454,875 A | 6/1984 | Pratt et al. |
| 4,456,006 A | 6/1984 | Wevers et al. |
| 4,485,816 A | 12/1984 | Krumme |
| 4,485,817 A | 12/1984 | Swiggett |
| 4,488,523 A | 12/1984 | Shichman |
| 4,508,253 A | 4/1985 | Green |
| 4,508,523 A | 4/1985 | Leu |
| 4,522,206 A | 6/1985 | Whipple et al. |
| 4,534,350 A | 8/1985 | Golden et al. |
| 4,535,772 A | 8/1985 | Sheehan |
| 4,566,620 A | 1/1986 | Green et al. |
| 4,570,623 A | 2/1986 | Ellison et al. |
| 4,606,343 A | 8/1986 | Conta et al. |
| 4,606,344 A | 8/1986 | Di Giovanni |
| 4,610,383 A | 9/1986 | Rothfuss et al. |
| 4,612,923 A | 9/1986 | Kronenthal |
| 4,612,933 A | 9/1986 | Brinkerhoff et al. |
| D286,442 S | 10/1986 | Korthoff et al. |
| 4,627,437 A | 12/1986 | Bedi et al. |
| 4,635,637 A | 1/1987 | Schreiber |
| 4,662,371 A | 5/1987 | Whipple et al. |
| 4,671,280 A | 6/1987 | Dorband et al. |
| 4,705,038 A | 11/1987 | Sjostrom et al. |
| 4,712,550 A | 12/1987 | Sinnett |
| 4,719,917 A | 1/1988 | Barrows et al. |
| 4,724,839 A | 2/1988 | Bedi et al. |
| 4,731,058 A | 3/1988 | Doan |
| 4,805,617 A | 2/1989 | Bedi et al. |
| 4,807,628 A | 2/1989 | Peters et al. |
| 4,852,558 A | 8/1989 | Outerbridge |
| 4,913,144 A | 4/1990 | Del Medico |
| 4,960,420 A | 10/1990 | Goble et al. |
| 4,962,877 A | 10/1990 | Hervas |
| 4,990,153 A | 2/1991 | Richards |
| 4,994,073 A | 2/1991 | Green |
| 4,995,877 A | 2/1991 | Ams et al. |
| 5,040,715 A | 8/1991 | Green et al. |
| 5,065,929 A | 11/1991 | Schulze et al. |
| 5,089,009 A | 2/1992 | Green |
| 5,108,422 A | 4/1992 | Green et al. |
| 5,114,399 A | 5/1992 | Kovalcheck |
| 5,129,570 A | 7/1992 | Schulze et al. |
| 5,143,453 A | 9/1992 | Weynant nee Girones |
| 5,203,864 A | 4/1993 | Phillips |
| 5,207,697 A | 5/1993 | Carusillo et al. |
| 5,209,756 A | 5/1993 | Seedhom et al. |
| 5,246,443 A | 9/1993 | Mai |
| 5,258,008 A | 11/1993 | Wilk |
| 5,271,543 A | 12/1993 | Grant et al. |
| RE34,519 E | 1/1994 | Fox et al. |
| 5,282,829 A | 2/1994 | Hermes |
| 5,300,081 A | 4/1994 | Young et al. |
| 5,307,976 A | 5/1994 | Olson et al. |
| 5,312,023 A | 5/1994 | Green et al. |
| 5,312,024 A | 5/1994 | Grant et al. |
| 5,313,935 A | 5/1994 | Kortenbach et al. |
| 5,318,221 A | 6/1994 | Green et al. |
| 5,326,013 A | 7/1994 | Green et al. |
| 5,330,486 A | 7/1994 | Wilk |
| 5,332,142 A | 7/1994 | Robinson et al. |
| 5,342,376 A | 8/1994 | Ruff |
| 5,350,355 A | 9/1994 | Sklar |
| 5,356,064 A | 10/1994 | Green et al. |
| 5,359,993 A | 11/1994 | Slater et al. |
| 5,364,001 A | 11/1994 | Bryan |
| 5,381,943 A | 1/1995 | Allen et al. |
| 5,383,874 A | 1/1995 | Jackson et al. |
| 5,383,880 A | 1/1995 | Hooven |
| 5,389,098 A | 2/1995 | Tsuruta et al. |
| 5,391,166 A | 2/1995 | Eggers |
| 5,395,030 A | 3/1995 | Kuramoto et al. |
| 5,395,033 A | 3/1995 | Byrne et al. |
| 5,400,267 A | 3/1995 | Denen et al. |
| 5,403,312 A | 4/1995 | Yates et al. |
| 5,405,344 A | 4/1995 | Williamson et al. |
| 5,411,508 A | 5/1995 | Bessler et al. |
| 5,413,267 A | 5/1995 | Solyntjes et al. |
| 5,431,323 A | 7/1995 | Smith et al. |
| 5,464,144 A | 11/1995 | Guy et al. |
| 5,467,911 A | 11/1995 | Tsuruta et al. |
| 5,478,344 A | 12/1995 | Stone et al. |
| 5,482,100 A | 1/1996 | Kuhar |
| 5,485,947 A | 1/1996 | Olson et al. |
| 5,487,499 A | 1/1996 | Sorrentino et al. |
| 5,497,933 A | 3/1996 | DeFonzo et al. |
| 5,500,000 A | 3/1996 | Feagin et al. |
| 5,503,320 A | 4/1996 | Webster et al. |
| 5,507,743 A | 4/1996 | Edwards et al. |
| 5,518,163 A | 5/1996 | Hooven |
| 5,518,164 A | 5/1996 | Hooven |
| 5,526,822 A | 6/1996 | Burbank et al. |
| 5,529,235 A * | 6/1996 | Boiarski ............... A61B 90/98 227/175.1 |
| 5,531,744 A | 7/1996 | Nardella et al. |
| 5,533,661 A | 7/1996 | Main et al. |
| 5,535,934 A | 7/1996 | Boiarski et al. |
| 5,535,937 A | 7/1996 | Boiarski et al. |
| 5,558,671 A | 9/1996 | Fates |
| 5,560,532 A | 10/1996 | DeFonzo et al. |
| 5,562,239 A | 10/1996 | Boiarski et al. |
| 5,571,285 A | 11/1996 | Chow et al. |
| 5,575,799 A | 11/1996 | Bolanos et al. |
| 5,582,611 A | 12/1996 | Tsuruta et al. |
| 5,584,835 A | 12/1996 | Greenfield |
| 5,601,224 A | 2/1997 | Bishop et al. |
| 5,601,558 A | 2/1997 | Torrie et al. |
| 5,607,095 A | 3/1997 | Smith et al. |
| 5,609,285 A | 3/1997 | Grant et al. |
| 5,609,560 A | 3/1997 | Ichikawa et al. |
| 5,624,452 A | 4/1997 | Yates |
| 5,632,433 A | 5/1997 | Grant et al. |
| 5,634,926 A | 6/1997 | Jobe |
| 5,642,848 A | 7/1997 | Ludwig et al. |
| 5,653,374 A | 8/1997 | Young et al. |
| 5,658,300 A | 8/1997 | Bito et al. |
| 5,658,312 A | 8/1997 | Green et al. |
| 5,662,662 A | 9/1997 | Bishop et al. |
| 5,665,085 A | 9/1997 | Nardella |
| 5,667,513 A | 9/1997 | Torrie et al. |
| 5,667,517 A | 9/1997 | Hooven |
| 5,667,527 A | 9/1997 | Cook |
| 5,669,544 A | 9/1997 | Schulze et al. |
| 5,673,841 A | 10/1997 | Schulze et al. |
| 5,676,674 A | 10/1997 | Bolanos et al. |
| 5,680,981 A | 10/1997 | Mililli et al. |
| 5,680,982 A | 10/1997 | Schulze et al. |
| 5,692,668 A | 12/1997 | Schulze et al. |
| 5,695,506 A | 12/1997 | Pike et al. |
| 5,695,524 A | 12/1997 | Kelley et al. |
| 5,702,447 A | 12/1997 | Walch et al. |
| 5,704,534 A | 1/1998 | Huitema et al. |
| 5,713,505 A | 2/1998 | Huitema |
| 5,713,896 A | 2/1998 | Nardella |

(56) References Cited

U.S. PATENT DOCUMENTS

| | | |
|---|---|---|
| 5,715,987 A | 2/1998 | Kelley et al. |
| 5,716,366 A | 2/1998 | Yates |
| 5,720,753 A | 2/1998 | Sander et al. |
| 5,725,529 A | 3/1998 | Nicholson et al. |
| 5,728,110 A | 3/1998 | Vidal et al. |
| 5,728,116 A | 3/1998 | Rosenman |
| 5,730,757 A | 3/1998 | Benetti et al. |
| 5,735,848 A | 4/1998 | Yates et al. |
| 5,738,474 A | 4/1998 | Blewett |
| 5,755,726 A | 5/1998 | Pratt et al. |
| 5,759,171 A | 6/1998 | Coelho et al. |
| 5,779,130 A | 7/1998 | Alesi et al. |
| 5,782,397 A | 7/1998 | Koukline |
| 5,785,713 A | 7/1998 | Jobe |
| 5,788,698 A | 8/1998 | Savornin |
| 5,810,811 A | 9/1998 | Yates et al. |
| 5,823,066 A | 10/1998 | Huitema et al. |
| 5,829,662 A | 11/1998 | Allen et al. |
| 5,830,121 A | 11/1998 | Enomoto et al. |
| 5,849,023 A | 12/1998 | Mericle |
| 5,849,028 A | 12/1998 | Chen |
| 5,855,311 A | 1/1999 | Hamblin et al. |
| 5,861,005 A | 1/1999 | Kontos |
| 5,865,361 A | 2/1999 | Milliman et al. |
| 5,876,401 A | 3/1999 | Schulze et al. |
| 5,891,156 A | 4/1999 | Gessner et al. |
| 5,893,813 A | 4/1999 | Yamamoto |
| 5,895,396 A | 4/1999 | Day et al. |
| 5,906,607 A | 5/1999 | Taylor et al. |
| 5,911,721 A | 6/1999 | Nicholson et al. |
| 5,918,791 A | 7/1999 | Sorrentino et al. |
| 5,928,222 A | 7/1999 | Kleinerman |
| 5,944,717 A | 8/1999 | Lee et al. |
| 5,944,736 A | 8/1999 | Taylor et al. |
| 5,954,259 A | 9/1999 | Viola et al. |
| 5,961,521 A | 10/1999 | Roger |
| 5,964,394 A | 10/1999 | Robertson |
| 5,968,044 A | 10/1999 | Nicholson et al. |
| 5,976,171 A | 11/1999 | Taylor |
| 5,980,518 A | 11/1999 | Carr et al. |
| 5,980,548 A | 11/1999 | Evans et al. |
| 5,991,355 A | 11/1999 | Dahlke |
| 5,991,650 A | 11/1999 | Swanson et al. |
| 5,992,724 A | 11/1999 | Snyder |
| 5,997,552 A | 12/1999 | Person et al. |
| 6,004,335 A | 12/1999 | Vaitekunas et al. |
| 6,007,550 A | 12/1999 | Wang et al. |
| 6,010,054 A | 1/2000 | Johnson et al. |
| 6,013,077 A | 1/2000 | Harwin |
| 6,015,417 A | 1/2000 | Reynolds, Jr. |
| 6,017,354 A | 1/2000 | Culp et al. |
| 6,030,410 A | 2/2000 | Zurbrugg |
| 6,032,849 A | 3/2000 | Mastri et al. |
| 6,039,731 A | 3/2000 | Taylor et al. |
| 6,051,007 A | 4/2000 | Hogendijk et al. |
| 6,063,078 A | 5/2000 | Wittkampf |
| 6,063,095 A | 5/2000 | Wang et al. |
| 6,077,246 A | 6/2000 | Kullas et al. |
| 6,079,606 A | 6/2000 | Milliman et al. |
| 6,080,150 A | 6/2000 | Gough |
| 6,083,242 A | 7/2000 | Cook |
| 6,090,123 A | 7/2000 | Culp et al. |
| 6,092,422 A | 7/2000 | Binnig et al. |
| 6,109,500 A * | 8/2000 | Alli ............... A61B 17/07207 227/175.2 |
| 6,113,592 A | 9/2000 | Taylor |
| 6,123,702 A | 9/2000 | Swanson et al. |
| H1904 H | 10/2000 | Yates et al. |
| 6,126,058 A | 10/2000 | Adams et al. |
| 6,126,651 A | 10/2000 | Mayer |
| 6,127,811 A | 10/2000 | Shenoy et al. |
| 6,132,425 A | 10/2000 | Gough |
| 6,165,169 A | 12/2000 | Panescu et al. |
| 6,166,538 A | 12/2000 | D'Alfonso |
| 6,179,840 B1 | 1/2001 | Bowman |
| 6,187,009 B1 | 2/2001 | Herzog et al. |
| 6,187,019 B1 | 2/2001 | Stefanchik et al. |
| 6,190,401 B1 | 2/2001 | Green et al. |
| 6,193,501 B1 | 2/2001 | Masel et al. |
| 6,202,914 B1 | 3/2001 | Geiste et al. |
| 6,217,573 B1 | 4/2001 | Webster |
| 6,228,534 B1 | 5/2001 | Takeuchi et al. |
| 6,231,565 B1 | 5/2001 | Tovey et al. |
| 6,236,874 B1 | 5/2001 | Devlin et al. |
| 6,237,604 B1 | 5/2001 | Burnside et al. |
| 6,241,139 B1 | 6/2001 | Milliman et al. |
| 6,245,065 B1 | 6/2001 | Panescu et al. |
| 6,248,117 B1 | 6/2001 | Blatter |
| 6,250,532 B1 | 6/2001 | Green et al. |
| 6,258,111 B1 | 7/2001 | Ross et al. |
| 6,264,086 B1 | 7/2001 | McGuckin, Jr. |
| 6,264,087 B1 | 7/2001 | Whitman |
| 6,264,653 B1 | 7/2001 | Falwell |
| 6,281,471 B1 | 8/2001 | Smart |
| 6,288,534 B1 | 9/2001 | Starkweather et al. |
| 6,290,701 B1 | 9/2001 | Enayati |
| 6,293,943 B1 | 9/2001 | Panescu et al. |
| 6,295,330 B1 | 9/2001 | Skog et al. |
| 6,315,184 B1 | 11/2001 | Whitman |
| 6,329,778 B1 | 12/2001 | Culp et al. |
| 6,330,965 B1 | 12/2001 | Milliman et al. |
| 6,346,104 B2 | 2/2002 | Daly et al. |
| 6,355,066 B1 | 3/2002 | Kim |
| 6,364,884 B1 | 4/2002 | Bowman et al. |
| 6,387,092 B1 | 5/2002 | Burnside et al. |
| 6,388,240 B2 | 5/2002 | Schulz et al. |
| 6,402,766 B2 | 6/2002 | Bowman et al. |
| H2037 H | 7/2002 | Yates et al. |
| 6,412,279 B1 | 7/2002 | Coleman et al. |
| 6,425,903 B1 | 7/2002 | Voegele |
| 6,436,097 B1 | 8/2002 | Nardella |
| 6,436,107 B1 | 8/2002 | Wang et al. |
| 6,436,110 B2 | 8/2002 | Bowman et al. |
| 6,443,973 B1 | 9/2002 | Whitman |
| 6,447,517 B1 | 9/2002 | Bowman |
| 6,461,372 B1 | 10/2002 | Jensen et al. |
| 6,478,210 B2 | 11/2002 | Adams et al. |
| 6,497,707 B1 | 12/2002 | Bowman et al. |
| 6,505,768 B2 | 1/2003 | Whitman |
| 6,515,273 B2 | 2/2003 | Al-Ali |
| 6,524,316 B1 | 2/2003 | Nicholson et al. |
| 6,533,157 B1 | 3/2003 | Whitman |
| 6,540,751 B2 | 4/2003 | Enayati |
| 6,544,273 B1 | 4/2003 | Harari et al. |
| 6,554,852 B1 | 4/2003 | Oberlander |
| 6,562,071 B2 | 5/2003 | Jarvinen |
| 6,578,579 B2 | 6/2003 | Burnside et al. |
| 6,601,748 B1 | 8/2003 | Fung et al. |
| 6,601,749 B2 | 8/2003 | Sullivan et al. |
| 6,602,252 B2 | 8/2003 | Mollenauer |
| 6,611,793 B1 | 8/2003 | Burnside et al. |
| 6,616,821 B2 | 9/2003 | Broadley et al. |
| 6,629,986 B1 | 10/2003 | Ross et al. |
| 6,651,669 B1 | 11/2003 | Burnside |
| 6,656,177 B2 | 12/2003 | Truckai et al. |
| 6,669,073 B2 | 12/2003 | Milliman et al. |
| 6,669,705 B2 | 12/2003 | Westhaver et al. |
| 6,696,008 B2 | 2/2004 | Brandinger |
| 6,698,643 B2 | 3/2004 | Whitman |
| 6,699,177 B1 | 3/2004 | Wang et al. |
| 6,716,233 B1 | 4/2004 | Whitman |
| 6,736,085 B2 | 5/2004 | Esnouf |
| 6,792,390 B1 | 9/2004 | Burnside et al. |
| 6,793,652 B1 | 9/2004 | Whitman et al. |
| 6,817,508 B1 | 11/2004 | Racenet et al. |
| 6,830,174 B2 | 12/2004 | Hillstead et al. |
| 6,843,403 B2 | 1/2005 | Whitman |
| 6,846,307 B2 | 1/2005 | Whitman et al. |
| 6,846,308 B2 | 1/2005 | Whitman et al. |
| 6,846,309 B2 | 1/2005 | Whitman et al. |
| 6,849,071 B2 | 2/2005 | Whitman et al. |
| 6,861,639 B2 | 3/2005 | Al-Ali |
| 6,872,214 B2 | 3/2005 | Sonnenschein et al. |
| 6,899,538 B2 | 5/2005 | Matoba |

(56) References Cited

U.S. PATENT DOCUMENTS

| | | |
|---|---|---|
| 6,900,004 B2 | 5/2005 | Satake |
| 6,905,057 B2 | 6/2005 | Swayze et al. |
| 6,926,636 B2 | 8/2005 | Luper |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,979,328 B2 | 12/2005 | Baerveldt et al. |
| 6,981,628 B2 | 1/2006 | Wales |
| 6,981,941 B2 | 1/2006 | Whitman et al. |
| 6,988,649 B2 | 1/2006 | Shelton, IV et al. |
| 7,000,819 B2 | 2/2006 | Swayze et al. |
| 7,032,798 B2 | 4/2006 | Whitman et al. |
| 7,044,353 B2 | 5/2006 | Mastri et al. |
| 7,048,687 B1 | 5/2006 | Reuss et al. |
| 7,055,731 B2 | 6/2006 | Shelton, IV et al. |
| 7,059,508 B2 | 6/2006 | Shelton, IV et al. |
| 7,077,856 B2 | 7/2006 | Whitman |
| 7,083,075 B2 | 8/2006 | Swayze et al. |
| 7,097,089 B2 | 8/2006 | Marczyk |
| 7,111,769 B2 | 9/2006 | Wales et al. |
| 7,118,564 B2 | 10/2006 | Ritchie et al. |
| 7,122,029 B2 | 10/2006 | Koop et al. |
| 7,128,253 B2 | 10/2006 | Mastri et al. |
| 7,128,254 B2 | 10/2006 | Shelton, IV et al. |
| 7,140,528 B2 | 11/2006 | Shelton, IV |
| 7,143,924 B2 | 12/2006 | Scirica et al. |
| 7,143,925 B2 | 12/2006 | Shelton, IV et al. |
| 7,143,926 B2 | 12/2006 | Shelton, IV et al. |
| 7,147,138 B2 | 12/2006 | Shelton, IV |
| 7,186,966 B2 | 3/2007 | Al-Ali |
| 7,193,519 B2 | 3/2007 | Root et al. |
| 7,213,736 B2 * | 5/2007 | Wales ............ A61B 17/07207 227/180.1 |
| 7,217,269 B2 | 5/2007 | El-Galley et al. |
| 7,220,232 B2 | 5/2007 | Suorsa et al. |
| 7,240,817 B2 | 7/2007 | Higuchi |
| 7,241,270 B2 | 7/2007 | Horzewski et al. |
| 7,246,734 B2 | 7/2007 | Shelton, IV |
| 7,303,108 B2 | 12/2007 | Shelton, IV |
| 7,328,828 B2 | 2/2008 | Ortiz et al. |
| 7,335,169 B2 | 2/2008 | Thompson et al. |
| 7,364,061 B2 | 4/2008 | Swayze et al. |
| 7,380,695 B2 | 6/2008 | Doll et al. |
| 7,380,696 B2 | 6/2008 | Shelton, IV et al. |
| 7,404,508 B2 | 7/2008 | Smith et al. |
| 7,416,101 B2 | 8/2008 | Shelton, IV et al. |
| 7,419,080 B2 | 9/2008 | Smith et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,431,189 B2 | 10/2008 | Shelton, IV et al. |
| 7,434,715 B2 | 10/2008 | Shelton, IV et al. |
| 7,441,684 B2 | 10/2008 | Shelton, IV et al. |
| 7,448,525 B2 | 11/2008 | Shelton, IV et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,481,348 B2 | 1/2009 | Marczyk |
| 7,487,899 B2 | 2/2009 | Shelton, IV et al. |
| 7,543,730 B1 | 6/2009 | Marczyk |
| 7,549,563 B2 | 6/2009 | Mather et al. |
| 7,552,854 B2 | 6/2009 | Wixey et al. |
| 7,556,185 B2 | 7/2009 | Viola |
| 7,568,603 B2 | 8/2009 | Shelton, IV et al. |
| 7,637,409 B2 | 12/2009 | Marczyk |
| 7,641,093 B2 | 1/2010 | Doll et al. |
| 7,644,848 B2 | 1/2010 | Swayze et al. |
| 7,648,055 B2 | 1/2010 | Marczyk |
| 7,654,431 B2 * | 2/2010 | Hueil ............ A61B 17/07207 227/175.1 |
| 7,670,334 B2 | 3/2010 | Hueil et al. |
| 7,694,809 B2 | 4/2010 | Garbini et al. |
| 7,721,931 B2 | 5/2010 | Shelton, IV et al. |
| 7,740,159 B2 | 6/2010 | Shelton, IV et al. |
| 7,753,248 B2 | 7/2010 | Viola |
| 7,757,925 B2 | 7/2010 | Viola et al. |
| 7,766,207 B2 | 8/2010 | Mather et al. |
| 7,766,210 B2 | 8/2010 | Shelton, IV et al. |
| 7,770,775 B2 | 8/2010 | Shelton, IV et al. |
| 7,784,663 B2 | 8/2010 | Shelton, IV |
| 7,815,090 B2 | 10/2010 | Marczyk |
| 7,823,760 B2 | 11/2010 | Zemlok et al. |
| 7,845,534 B2 | 12/2010 | Viola et al. |
| 7,870,989 B2 | 1/2011 | Viola et al. |
| 7,886,953 B2 | 2/2011 | Schwemberger et al. |
| 7,887,530 B2 | 2/2011 | Zemlok et al. |
| 7,905,897 B2 | 3/2011 | Whitman et al. |
| 7,909,221 B2 | 3/2011 | Viola et al. |
| 7,922,063 B2 | 4/2011 | Zemlok et al. |
| 7,931,660 B2 | 4/2011 | Aranyi et al. |
| 7,950,560 B2 | 5/2011 | Zemlok et al. |
| 7,955,352 B2 | 6/2011 | McEwen et al. |
| 8,006,885 B2 | 8/2011 | Marczyk |
| 8,006,887 B2 | 8/2011 | Marczyk |
| 8,011,551 B2 | 9/2011 | Marczyk et al. |
| 8,020,742 B2 | 9/2011 | Marczyk |
| 8,025,199 B2 | 9/2011 | Whitman et al. |
| 8,038,044 B2 | 10/2011 | Viola |
| 8,052,024 B2 | 11/2011 | Viola et al. |
| 8,066,721 B2 | 11/2011 | Kortenbach et al. |
| 8,074,858 B2 | 12/2011 | Marczyk |
| 8,092,493 B2 | 1/2012 | Marczyk |
| 8,128,645 B2 | 3/2012 | Sonnenschein et al. |
| 8,132,705 B2 | 3/2012 | Viola et al. |
| 8,157,150 B2 | 4/2012 | Viola et al. |
| 8,157,151 B2 * | 4/2012 | Ingmanson .......... A61B 17/072 227/176.1 |
| 8,186,555 B2 | 5/2012 | Shelton, IV et al. |
| 8,201,721 B2 | 6/2012 | Zemlok et al. |
| 8,210,412 B2 | 7/2012 | Marczyk |
| 8,240,536 B2 | 8/2012 | Marczyk |
| 8,240,537 B2 | 8/2012 | Marczyk |
| 8,267,924 B2 | 9/2012 | Zemlok et al. |
| 8,328,823 B2 | 12/2012 | Aranyi et al. |
| 8,348,125 B2 | 1/2013 | Viola et al. |
| 8,403,196 B2 * | 3/2013 | Beardsley ............ A61B 17/068 227/175.1 |
| 8,685,004 B2 | 4/2014 | Zemlock et al. |
| 8,864,010 B2 * | 10/2014 | Williams .......... A61B 17/07207 227/175.1 |
| 8,899,462 B2 | 12/2014 | Kostrzewski et al. |
| 9,016,539 B2 | 4/2015 | Kostrzewski et al. |
| 9,192,381 B2 | 11/2015 | Marczyk |
| 9,364,222 B2 | 6/2016 | Zemlok et al. |
| 9,370,360 B2 | 6/2016 | Marczyk |
| 9,370,361 B2 | 6/2016 | Viola et al. |
| 9,433,415 B2 | 9/2016 | Marczyk et al. |
| 9,480,492 B2 | 11/2016 | Aranyi et al. |
| 9,585,659 B2 | 3/2017 | Viola et al. |
| 9,724,094 B2 * | 8/2017 | Baber ..................... H02J 1/001 |
| 9,775,610 B2 | 10/2017 | Nicholas et al. |
| 9,943,309 B2 * | 4/2018 | Shelton, IV .......... A61B 17/105 |
| 10,130,367 B2 * | 11/2018 | Cappola ................ A61B 90/90 |
| 2002/0103489 A1 | 8/2002 | Ku |
| 2002/0111641 A1 | 8/2002 | Peterson et al. |
| 2002/0165541 A1 | 11/2002 | Whitman |
| 2003/0090201 A1 | 5/2003 | Peng |
| 2003/0114851 A1 | 6/2003 | Truckai et al. |
| 2003/0120306 A1 | 6/2003 | Burbank et al. |
| 2004/0232201 A1 | 11/2004 | Wenchell et al. |
| 2005/0010235 A1 | 1/2005 | VanDusseldorp |
| 2005/0131390 A1 | 6/2005 | Heinrich et al. |
| 2005/0139636 A1 | 6/2005 | Schwemberger et al. |
| 2005/0165415 A1 | 7/2005 | Wales |
| 2005/0177176 A1 | 8/2005 | Gerbi et al. |
| 2005/0192609 A1 | 9/2005 | Whitman et al. |
| 2005/0247753 A1 | 11/2005 | Kelly et al. |
| 2006/0000867 A1 | 1/2006 | Shelton et al. |
| 2006/0016853 A1 * | 1/2006 | Racenet ............ A61B 17/068 227/176.1 |
| 2007/0023477 A1 | 2/2007 | Whitman et al. |
| 2007/0029363 A1 | 2/2007 | Popov |
| 2007/0084897 A1 | 4/2007 | Shelton et al. |

(56) References Cited

U.S. PATENT DOCUMENTS

| | | |
|---|---|---|
| 2007/0102472 A1 | 5/2007 | Shelton |
| 2007/0175949 A1 | 8/2007 | Shelton et al. |
| 2007/0175950 A1 | 8/2007 | Shelton et al. |
| 2007/0175951 A1 | 8/2007 | Shelton et al. |
| 2007/0175955 A1 | 8/2007 | Shelton et al. |
| 2007/0219563 A1 | 9/2007 | Voegele |
| 2008/0029570 A1 | 2/2008 | Shelton et al. |
| 2008/0029573 A1 | 2/2008 | Shelton et al. |
| 2008/0029574 A1 | 2/2008 | Shelton et al. |
| 2008/0029575 A1 | 2/2008 | Shelton et al. |
| 2008/0135600 A1 | 6/2008 | Hiranuma et al. |
| 2008/0169329 A1 | 7/2008 | Shelton et al. |
| 2008/0185419 A1 | 8/2008 | Smith et al. |
| 2008/0197167 A1 | 8/2008 | Viola et al. |
| 2008/0255413 A1 | 10/2008 | Zemlok et al. |
| 2008/0255607 A1 | 10/2008 | Zemlok |
| 2009/0018624 A1 | 1/2009 | Levinson et al. |
| 2009/0090201 A1 | 4/2009 | Viola |
| 2009/0090763 A1 | 4/2009 | Zemlok et al. |
| 2010/0200636 A1 | 8/2010 | Zemlok et al. |
| 2010/0312257 A1 | 12/2010 | Aranyi |
| 2010/0320254 A1 | 12/2010 | Zemlok et al. |
| 2011/0034910 A1 | 2/2011 | Ross et al. |
| 2011/0062211 A1 | 3/2011 | Ross et al. |
| 2011/0121049 A1 | 5/2011 | Malinouskas et al. |
| 2011/0168757 A1 | 7/2011 | Viola et al. |
| 2011/0172681 A1 | 7/2011 | Aranyi et al. |
| 2011/0190738 A1 | 8/2011 | Zemlok et al. |
| 2011/0301579 A1 | 12/2011 | Marczyk et al. |
| 2011/0303735 A1 | 12/2011 | Marczyk |
| 2012/0055972 A1 | 3/2012 | Marczyk |
| 2012/0074197 A1 | 3/2012 | Marczyk |
| 2012/0175400 A1 | 7/2012 | Viola et al. |
| 2012/0193393 A1 | 8/2012 | Viola et al. |
| 2012/0198288 A1 | 8/2012 | Njo et al. |
| 2012/0220989 A1 | 8/2012 | Zemlok et al. |
| 2012/0223121 A1 | 9/2012 | Viola et al. |
| 2012/0241494 A1 | 9/2012 | Marczyk |
| 2012/0277790 A1 | 11/2012 | Zemlok et al. |
| 2012/0298718 A1 | 11/2012 | Marczyk |
| 2012/0298720 A1 | 11/2012 | Marczyk |
| 2014/0012289 A1 | 1/2014 | Snow et al. |
| 2014/0110455 A1* | 4/2014 | Ingmanson ...... A61B 17/07207 227/176.1 |
| 2014/0110456 A1* | 4/2014 | Taylor ................. A61B 17/072 227/176.1 |
| 2014/0171923 A1 | 6/2014 | Aranyi |
| 2015/0366560 A1* | 12/2015 | Chen ....................... A61B 90/92 227/176.1 |
| 2016/0100839 A1 | 4/2016 | Marczyk et al. |
| 2016/0310134 A1* | 10/2016 | Contini ............. A61B 17/0686 |
| 2017/0189023 A1 | 7/2017 | Yan |
| 2017/0224339 A1* | 8/2017 | Huang ................. A61B 17/295 |
| 2018/0168623 A1* | 6/2018 | Simms ................. A61B 17/072 |
| 2018/0235611 A1* | 8/2018 | Harris ................. A61B 17/072 |

FOREIGN PATENT DOCUMENTS

| | | |
|---|---|---|
| EP | 0537570 A2 | 4/1993 |
| EP | 0647431 A2 | 4/1995 |
| EP | 0738501 A1 | 10/1996 |
| EP | 0770354 A1 | 5/1997 |
| EP | 1070487 A2 | 1/2001 |
| EP | 1201196 A1 | 5/2002 |
| EP | 1658817 A1 | 5/2006 |
| EP | 1813203 A2 | 8/2007 |
| EP | 2586378 A2 | 5/2013 |
| EP | 2722010 A1 | 4/2014 |
| EP | 2942016 A1 | 11/2015 |
| EP | 2944274 A2 | 11/2015 |
| EP | 3034017 A2 | 6/2016 |
| EP | 3037045 A1 | 6/2016 |
| EP | 3106099 A1 | 12/2016 |
| EP | 3409215 A1 | 12/2018 |
| FR | 2 849 589 A1 | 7/2004 |
| WO | 9414129 A1 | 6/1994 |
| WO | 9729694 A1 | 8/1997 |
| WO | 9740760 A1 | 11/1997 |
| WO | 9837825 A1 | 9/1998 |
| WO | 1999/52489 A1 | 10/1999 |
| WO | 0051486 A1 | 9/2000 |
| WO | 0234140 A2 | 5/2002 |
| WO | 03026511 A1 | 4/2003 |
| WO | 03030743 A2 | 4/2003 |
| WO | 2004/032760 A2 | 4/2004 |
| WO | 2007030753 A2 | 3/2007 |
| WO | 2007/114868 A2 | 10/2007 |
| WO | 2007118179 A2 | 10/2007 |
| WO | 2009039506 A1 | 3/2009 |
| WO | 2007014355 A3 | 4/2009 |
| WO | 2009143092 A1 | 11/2009 |
| WO | 2013063525 A1 | 5/2013 |

OTHER PUBLICATIONS

Extended European Search Report issued in corresponding European Application No. 19202762.1 dated Jan. 28, 2020, 7 pages.

Partial European Search Report issued in European Application No. 18203222.7 dated Mar. 6, 2019, 16 pages.

Detemple, P., "Microtechnology in Modern Health Care", Med Device Technol. 9(9):18-25 (1998).

Abridged Data Sheet, "DeepCover Secure Authenticator with 1-Wire SHA-256 and 512-Bit User EEPROM", Maxim Integrated Products, Inc. pp. 1-4; 42; Dec. 2012.

Data Sheet "DS28E15-1—Sire SHA-256 Secure Authenticator with 512-Bit User EEPROM"; IC-ON-LINE, Electronic Component Manufacturers, pp. 1-2; Aug. 2013.

* cited by examiner

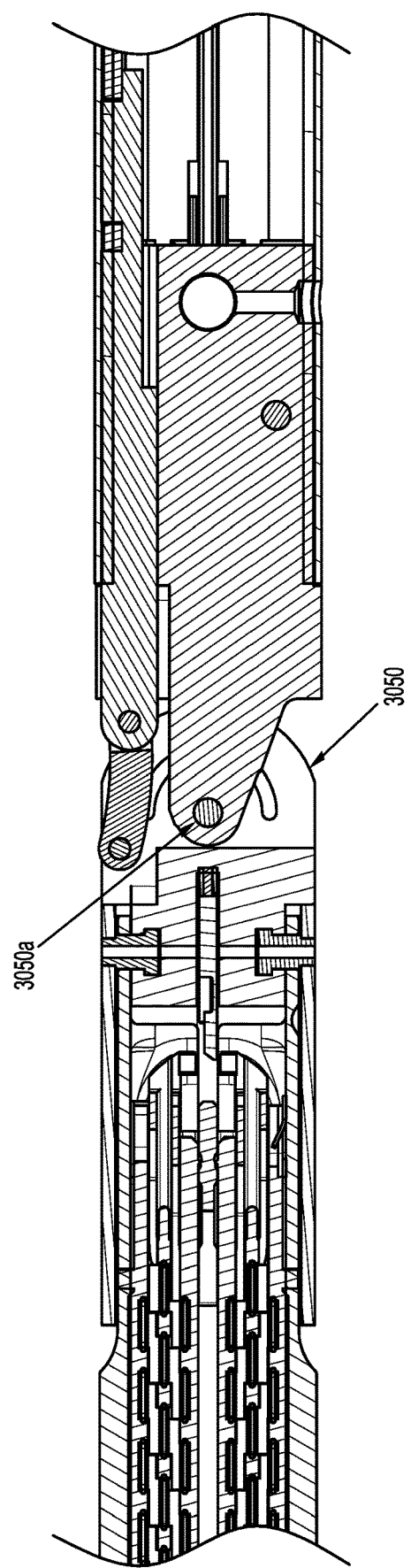

APPARATUS FOR ENDOSCOPIC PROCEDURES

CROSS REFERENCE TO RELATED APPLICATIONS

This application claims the benefit of U.S. Provisional Patent Application Ser. No. 62/578,673, filed Oct. 30, 2017, the entire contents of which are incorporated by reference herein.

TECHNICAL FIELD

The present disclosure relates to surgical apparatus, devices and/or systems for performing endoscopic surgical procedures and methods of use thereof. More specifically, the present disclosure relates to manual, electromechanical, robotic and/or hand-held surgical apparatus, devices and/or systems configured for use with removable disposable loading units and/or single use loading units for clamping, cutting and/or stapling tissue.

BACKGROUND

A number of surgical device manufacturers have developed product lines with proprietary drive systems for operating and/or manipulating electromechanical surgical devices. In many instances the electromechanical surgical devices include a handle assembly, which is reusable, and disposable loading units and/or single use loading units or the like that are selectively connected to the handle assembly prior to use and then disconnected from the handle assembly following use in order to be disposed of or in some instances sterilized for re-use.

Various electromechanical linkages are utilized to transmit power from the reusable handle assemblies, which include one or more motors, to the disposable loading unit to effect rotation, pivoting, clamping, fastener ejection, etc. Due to the complex structure and operation of the power transmission mechanisms inadvertent actuation of these mechanisms may result in unintended operation of the disposable loading unit, which may result in damage to the surgical device and/or injury to the patient. Robotic systems for performing minimally invasive surgery are also known. For example, International Application Publication WO 2000/051486 discloses a system having remotely-controlled surgical instruments.

Many of these electromechanical surgical devices are relatively expensive to manufacture, purchase and/or operate. There is a constant desire by manufacturers and end users to develop electromechanical surgical devices that are relatively inexpensive to manufacture, purchase and/or operate that still provide a large degree of operability with prerequisite safety features. Accordingly, a need exists for electromechanical surgical apparatus, devices and/or systems that include effective electromechanical transmission system for actuating the disposable units as well as safety lockout assemblies.

SUMMARY

In a first aspect of the present disclosure, a surgical stapling instrument comprises a reload including a staple cartridge assembly and an anvil assembly moveable with respect to one another. An adapter assembly has an elongate shaft and an articulating distal end, a mounting member being disposed at the distal end and being pivotably attached to the elongate shaft, the mounting member having a connection feature for attaching the reload to the adapter assembly. A drive mechanism is in the adapter, the drive mechanism including a bar extending through the mounting member and having a beam at a distal end of the bar, the bar being flexible and supported by a pair of bar guides, one of the bar guides alongside a first side of the bar, and the other of the bar guides being alongside a second side of the bar, the bar being further supported by a pair of blowout plates, one of the blowout plates being alongside the first side of the bar, and the other of the blowout plates being alongside the second side of the bar, the pair of blowout plates being distal to the pair of bar guides, the bar being further supported by a support block having an opening, the bar and the pair of blowout plates being disposed in the opening of the support block, the bar, the pair of bar guides, the pair of blowout plates, and the support block being pivotable from a central position in the adapter assembly to an off-center position in the adapter assembly.

The support block can be curved. The mounting member can have a curved slot, the support block can be disposed in the curved slot, so that the support block is movable in the curved slot.

An articulation link extends inside the elongate shaft, and a second link pivotably connected to the articulation link and to the mounting member. The second link can be curved.

The bar can have a plurality of layers stacked together. The beam can have an upper flange and a lower flange. The bar can be attached to a threaded drive member. The threaded drive member may be disposed inside an inner tube having an interior thread. The connection feature can define a keyway. The reload may define a tab that is received in the keyway.

In another aspect, a surgical stapling system comprises: a hand-held instrument handle having a battery, a motor and computer and memory components; a removable and replaceable adapter assembly; a first linear surgical stapling reload having a first end effector, the first linear surgical stapling reload being removably and replaceably attachable to the adapter assembly; and a second linear surgical stapling reload having a second end effector and being removably and replaceably attachable to the adapter assembly, the second linear surgical stapling reload having a feature and the first linear stapling reload not having the feature, each of the first linear surgical stapling reload and the second linear surgical stapling reload having a staple cartridge assembly and an anvil assembly.

The adapter assembly corresponds to the first linear surgical stapling reload and the second linear surgical stapling reload. The feature can be a dissecting tip on a distal end of the anvil assembly of the second linear surgical stapling reload.

The feature can be a stapling buttress on each of the anvil assembly and the staple cartridge assembly of the second linear surgical stapling reload.

The handle can be sterilizable and re-used for a prescribed number of procedures.

Further details and aspects of exemplary embodiments of the present invention are described in more detail below with reference to the appended figures.

BRIEF DESCRIPTION OF THE DRAWINGS

Embodiments of the present disclosure are described herein with reference to the accompanying drawings, wherein:

FIG. 45 is a perspective view of the articulation mechanism in the distal end of the adapter assembly;

DETAILED DESCRIPTION OF EMBODIMENTS

Figure 1:
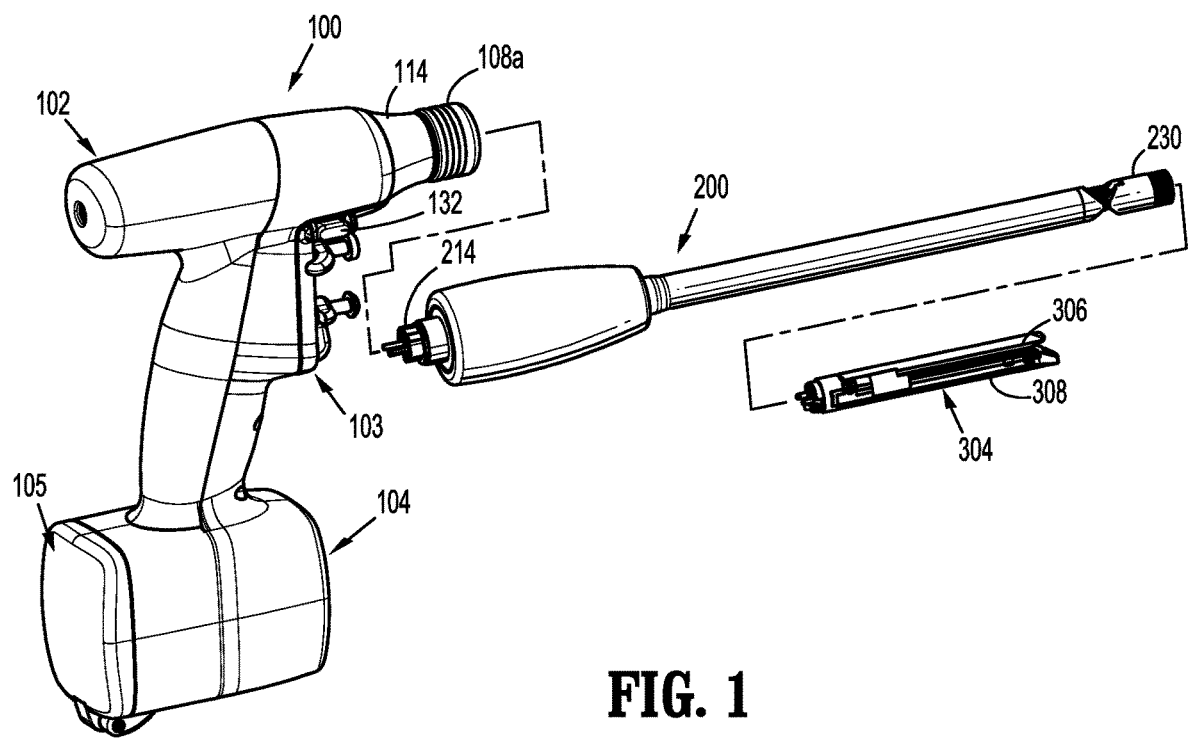
FIG. 1 is a perspective, disassembled view of an electromechanical surgical system including a surgical instrument, an adapter assembly, and an end effector, according to the present disclosure.

Embodiments of the presently disclosed electromechanical surgical system, apparatus and/or device are described in detail with reference to the drawings, in which like reference numerals designate identical or corresponding elements in each of the several views. As used herein the term "distal" refers to that portion of the electromechanical surgical system, apparatus and/or device, or component thereof, that are farther from the user, while the term "proximal" refers to that portion of the electromechanical surgical system, apparatus and/or device, or component thereof, that are closer to the user. The terms "left" and "right" refer to that portion of the electromechanical surgical system, apparatus and/or device, or component thereof, that are on the left and right sides, respectively, from the perspective of the user facing the distal end of the electromechanical surgical system, apparatus and/or device from the proximal end while the surgical system, apparatus and/or device is oriented in non-rotational configuration.

Reference may be made to International Application Publication No. WO 2009/039506, U.S. Pat. No. 9,775,610, and U.S. Patent Application Publication US 2011/0121049, the entire contents of each of which are incorporated by reference herein, for a detailed description of the construction and operation of exemplary electromechanical, hand-held, powered surgical instrument 100.

Referring initially to FIGS. 1-8, an electromechanical, hand-held, powered surgical system, in accordance with an embodiment of the present disclosure is shown and generally designated 10. Electromechanical surgical system 10 includes a surgical apparatus or device in the form of an electromechanical, hand-held, powered surgical instrument 100 that is configured for selective attachment thereto of a plurality of different end effectors 300, via an adapter assembly (e.g., elongated body) 200. The end effector 300 and the adapter assembly 200 are configured for actuation and manipulation by the electromechanical, hand-held, powered surgical instrument 100. In particular, the surgical instrument 100, the adapter assembly 200, and the end effector 300 are separable from each other such that the surgical instrument 100 is configured for selective connection with adapter assembly 200, and, in turn, adapter assembly 200 is configured for selective connection with any one of a plurality of different end effectors 300.

The end effector and/or adapter can be configured as an integral unit in any of the embodiments disclosed herein. The end effector and/or adapter can be configured for use with a powered handle, console, and/or surgical robot, in any of the embodiments disclosed herein.

Figure 2:
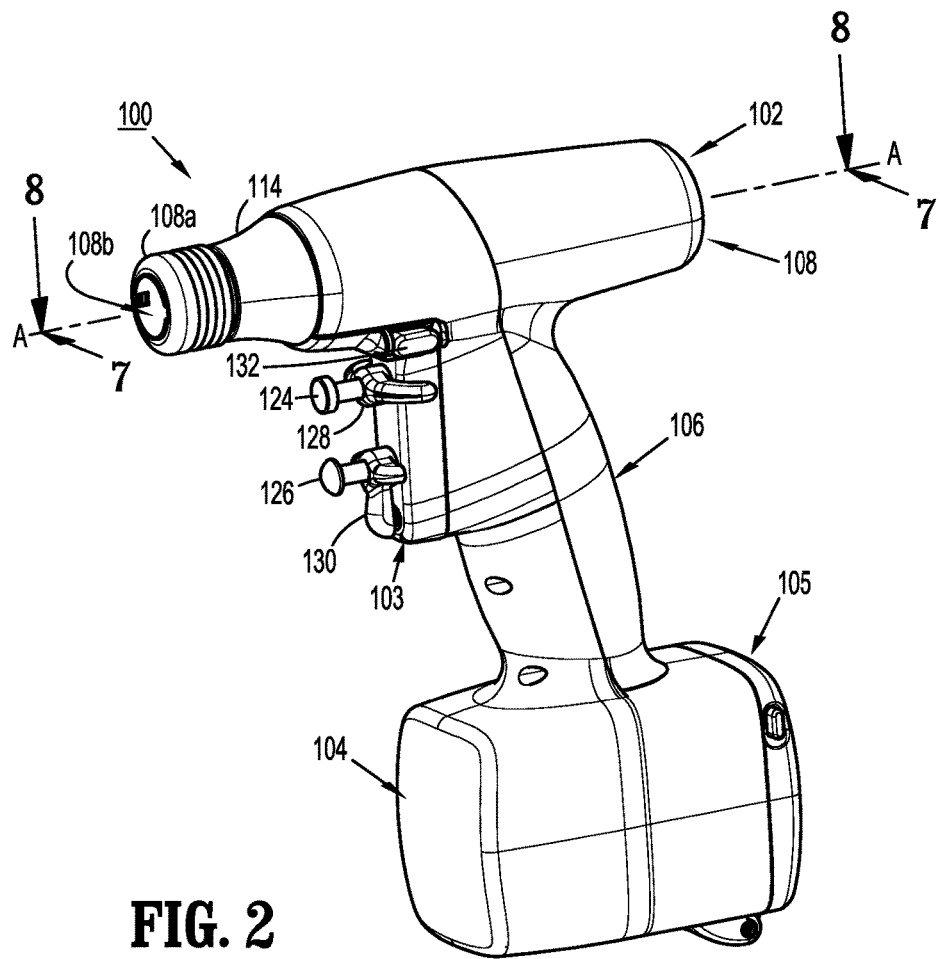
FIG. 2 is a perspective view of the surgical instrument of FIG. 1, according to the present disclosure.
Figure 3:
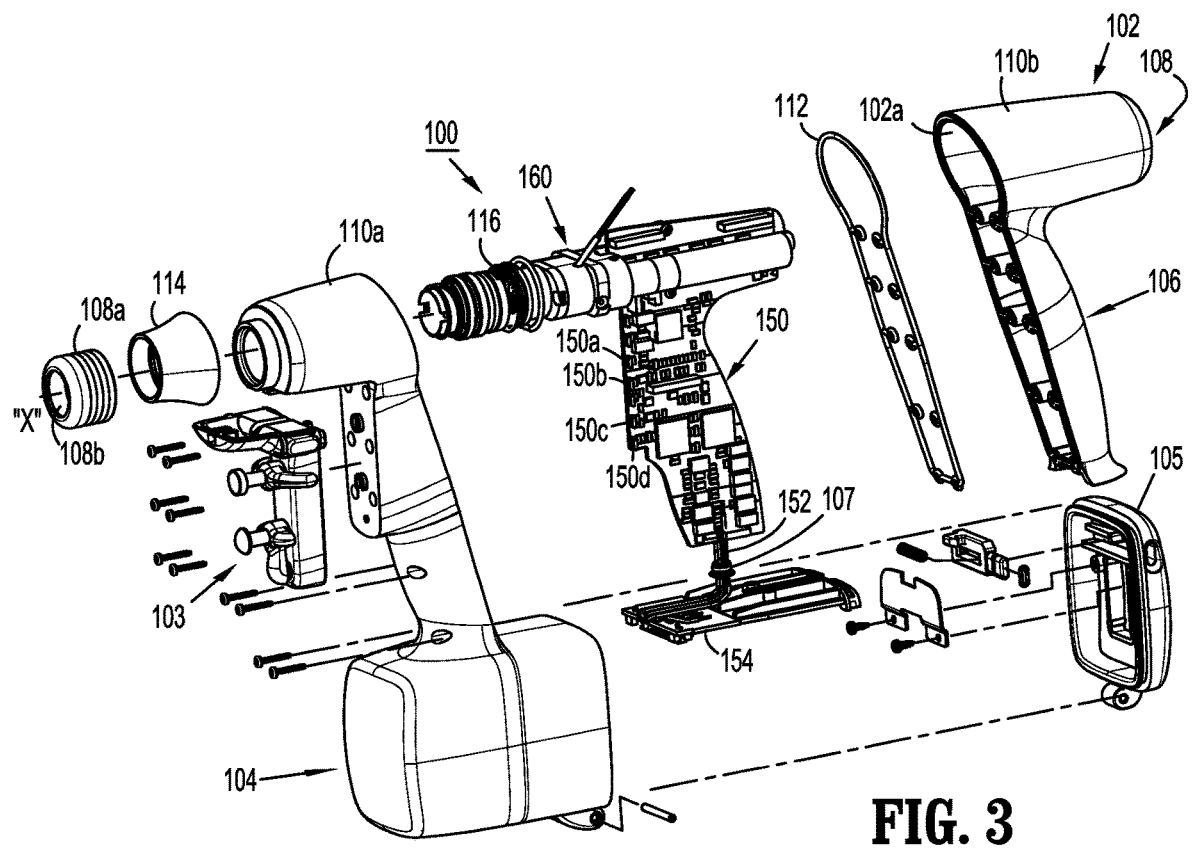
FIG. 3 is perspective, disassembled view of the surgical instrument of FIG. 1, according to the present disclosure.

As illustrated in FIGS. 1-3, the hand-held surgical instrument 100 includes a handle housing 102 having a lower housing portion 104, an intermediate housing portion 106 extending from and/or supported on lower housing portion 104, and an upper housing portion 108 extending from and/or supported on intermediate housing portion 106. Intermediate housing portion 106 and upper housing portion 108 are separated into a distal half-section 110a that is integrally formed with and extending from the lower portion 104, and a proximal half-section 110b connectable to distal half-section 110a by a plurality of fasteners. When joined, distal and proximal half-sections 110a, 110b define a handle housing 102 having a cavity 102a therein in which a circuit board 150 and a drive mechanism 160 are situated.

With reference to FIGS. 2 and 3, distal and proximal half-sections 110a, 110b are divided along a vertical plane that traverses a longitudinal axis "A-A" of upper housing portion 108 (FIG. 2). Handle housing 102 includes a gasket 112 extending completely around a rim of distal half-section and/or proximal half-section 110a, 110b and being interposed between distal half-section 110a and proximal half-section 110b. Gasket 112 seals the perimeter of distal half-section 110a and proximal half-section 110b. Gasket 112 functions to establish an air-tight seal between distal half-section 110a and proximal half-section 110b such that circuit board 150 and drive mechanism 160 are protected from sterilization and/or cleaning procedures.

In this manner, the cavity 102a of handle housing 102 is sealed along the perimeter of distal half-section 110a and proximal half-section 110b yet is configured to enable easier, more efficient assembly of circuit board 150 and a drive mechanism 160 in handle housing 102.

Intermediate housing portion 106 of handle housing 102 provides a housing in which circuit board 150 is situated. Circuit board 150 is configured to control the various operations of surgical instrument 100, as will be set forth in additional detail below.

Figure 4:
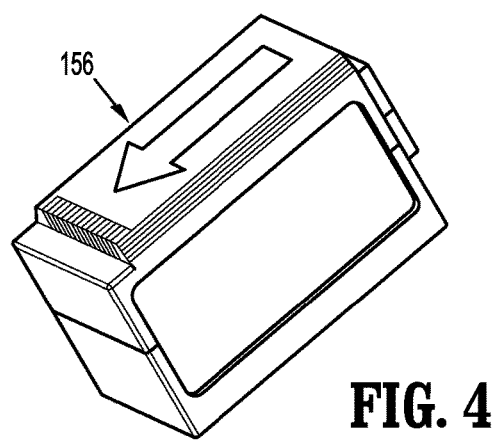
FIG. 4 is a perspective view of a battery of the surgical instrument of FIG. 1, according to the present disclosure.

Lower housing portion 104 of surgical instrument 100 defines an aperture (not shown) formed in an upper surface thereof and which is located beneath or within intermediate housing portion 106. As shown in FIGS. 3 and 4, the aperture of lower housing portion 104 provides a passage through which wires 152 pass to electrically interconnect electrical components situated in lower housing portion 104, e.g., a battery 156 and a circuit board 154, with electrical components situated in intermediate housing portion 106 and/or upper housing portion 108, e.g., circuit board 150, drive mechanism 160, etc.

Handle housing 102 includes a gasket 107 disposed within the aperture of lower housing portion 104 thereby plugging or sealing the aperture of lower housing portion 104 while allowing wires 152 to pass therethrough (see FIG. 3). Gasket 107 functions to establish an air-tight seal between lower housing portion 106 and intermediate housing portion 108 such that circuit board 150 and drive mechanism 160 are protected from sterilization and/or cleaning procedures.

With continued reference to FIGS. 3 and 4, lower housing portion 104 of handle housing 102 provides a housing in which the battery 156 is removably disposed therein. The battery 156 may be a rechargeable battery (e.g., lead-based, nickel-based, lithium-ion based, etc.). It is also envisioned that the battery 156 may be a single-use, non-rechargeable battery. Battery 156 is configured to supply power to any of the electrical components of surgical instrument 100. Lower housing portion 104 defines a cavity (not shown) into which battery 156 is inserted. Lower housing portion 104 includes a door 105 pivotally connected thereto for closing cavity of lower housing portion 104 and retaining battery 156 therein.

Figure 5:
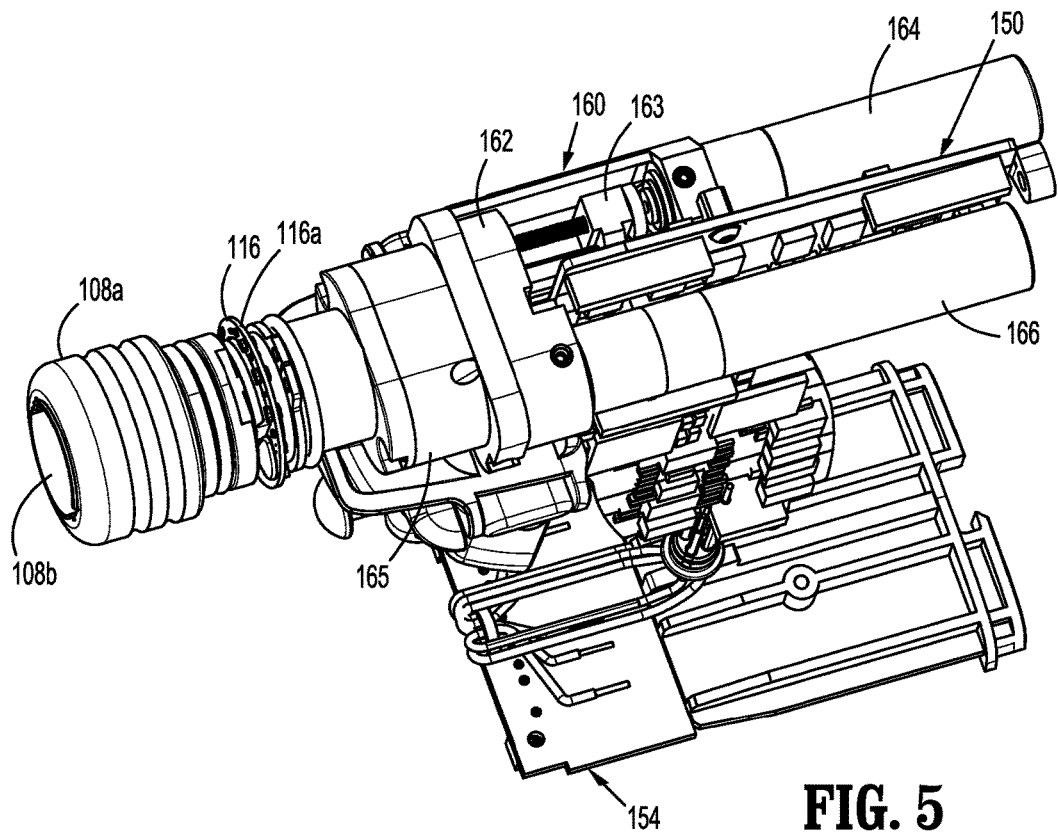
FIG. 5 is a top, partially-disassembled view of the surgical instrument of FIG. 1, according to the present disclosure.

With continued reference to FIGS. 3 and 5, distal half-section 110a of upper housing portion 108 defines a nose or connecting portion 108a. A nose cone 114 is supported on nose portion 108a of upper housing portion 108. Nose cone 114 is fabricated from a transparent, light-transmissive material. An illumination member 116 is disposed within nose cone 114 such that illumination member 116 is visible therethrough. The nose cone 114 may be tinted, such that the illumination member 116 is visible when it is activated.

With reference to FIG. 5, the illumination member 116 may include a plurality of any suitable light emitting devices, such as light emitting diodes (LEDs), disposed on printed circuit board (LED PCB) 116a which is disposed in a vertical plane transverse to the longitudinal axis "A-A." The illumination member 116 is configured to illuminate in multiple colors with a specific color pattern being associated with a unique discrete event. In embodiments, the LEDs may be single-color or multi-color LEDs.

Upper housing portion 108 of handle housing 102 provides a housing in which drive mechanism 160 is situated. As illustrated in FIG. 5, drive mechanism 160 is configured to drive shafts and/or gear components in order to perform the various operations of surgical instrument 100. In particular, drive mechanism 160 is configured to drive shafts and/or gear components in order to selectively move tool assembly 304 of end effector 300 relative to the adapter assembly, to rotate end effector 300 about the longitudinal axis "A-A" (FIG. 2) relative to handle housing 102, to move anvil assembly 306 relative to cartridge assembly 308 of end effector 300, and/or to fire a stapling and cutting cartridge within cartridge assembly 308 of end effector 300.

The drive mechanism 160 includes a selector gearbox assembly 162 that is located immediately proximal relative to adapter assembly 200. Proximal to the selector gearbox assembly 162 is a function selection module 163 having a first (e.g., selector) motor 164 that functions to selectively move gear elements within the selector gearbox assembly 162 into engagement with an input drive component 165 having a second (e.g., drive) motor 166.

As illustrated in FIGS. 1-4, distal half-section 110a of upper housing portion 108 defines a connecting portion 108a configured to accept a corresponding shaft coupling assembly 214 of adapter assembly 200.

Figure 6:
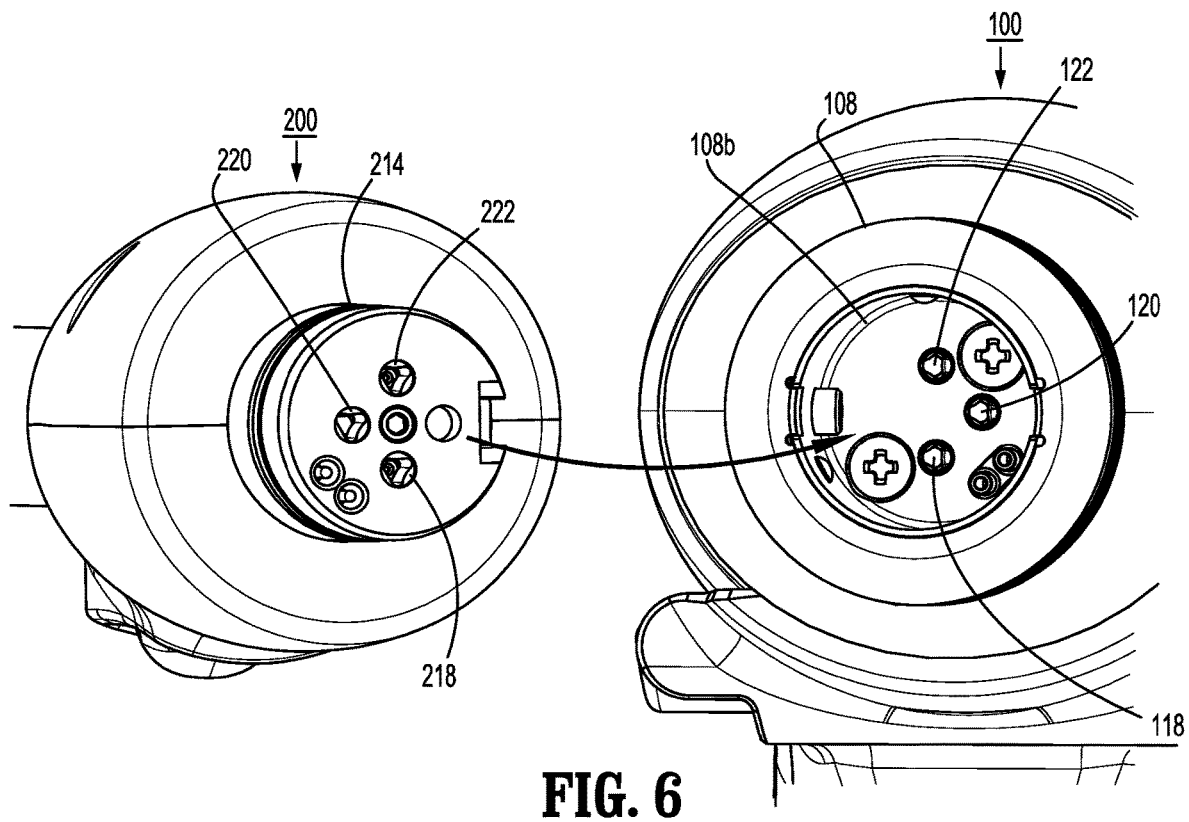
FIG. 6 is a front, perspective view of the surgical instrument of FIG. 1 with the elongated member separated therefrom, according to the present disclosure.
Figure 7:
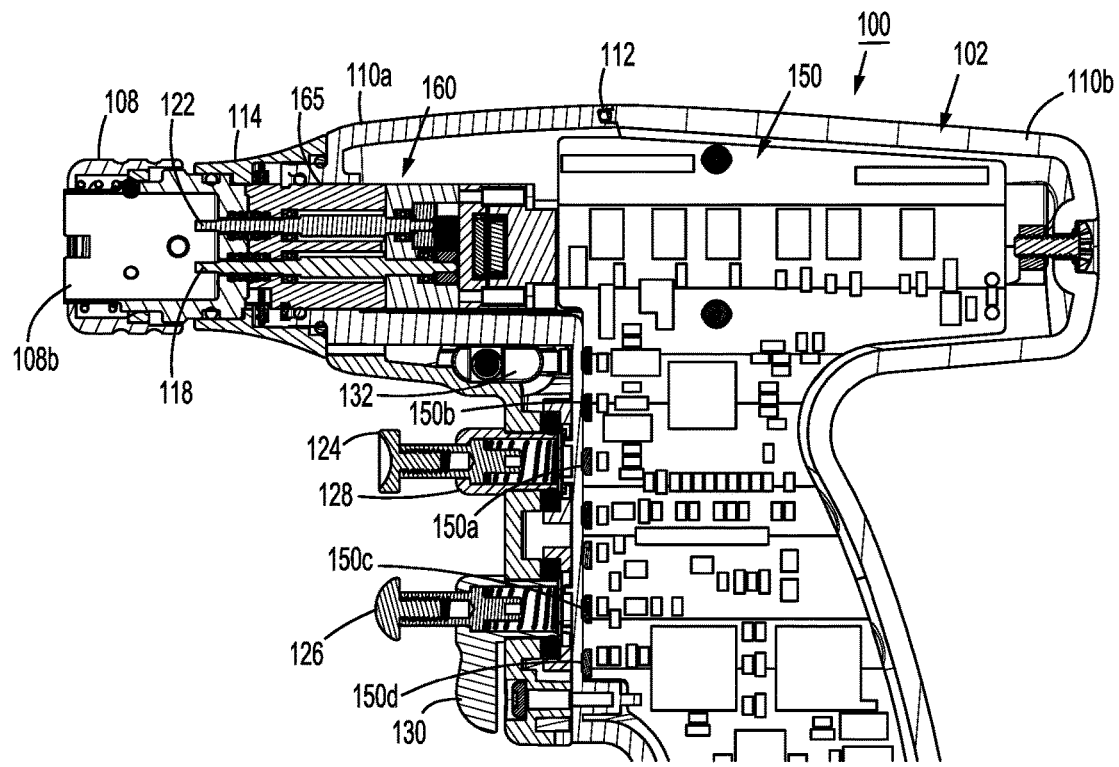
FIG. 7 is a cross-sectional side view of the surgical instrument of FIG. 1, as taken through 7-7 of FIG. 1, according to the present disclosure.
Figure 8:
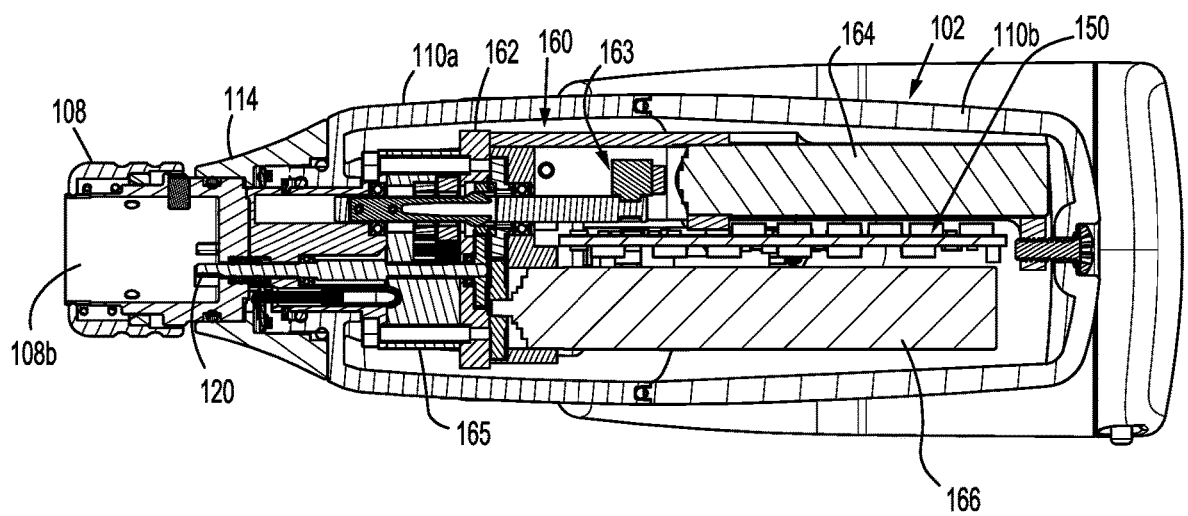
FIG. 8 is a top, cross-sectional view of the surgical instrument of FIG. 1, as taken through 8-8 of FIG. 1, according to the present disclosure.
Figure 9:
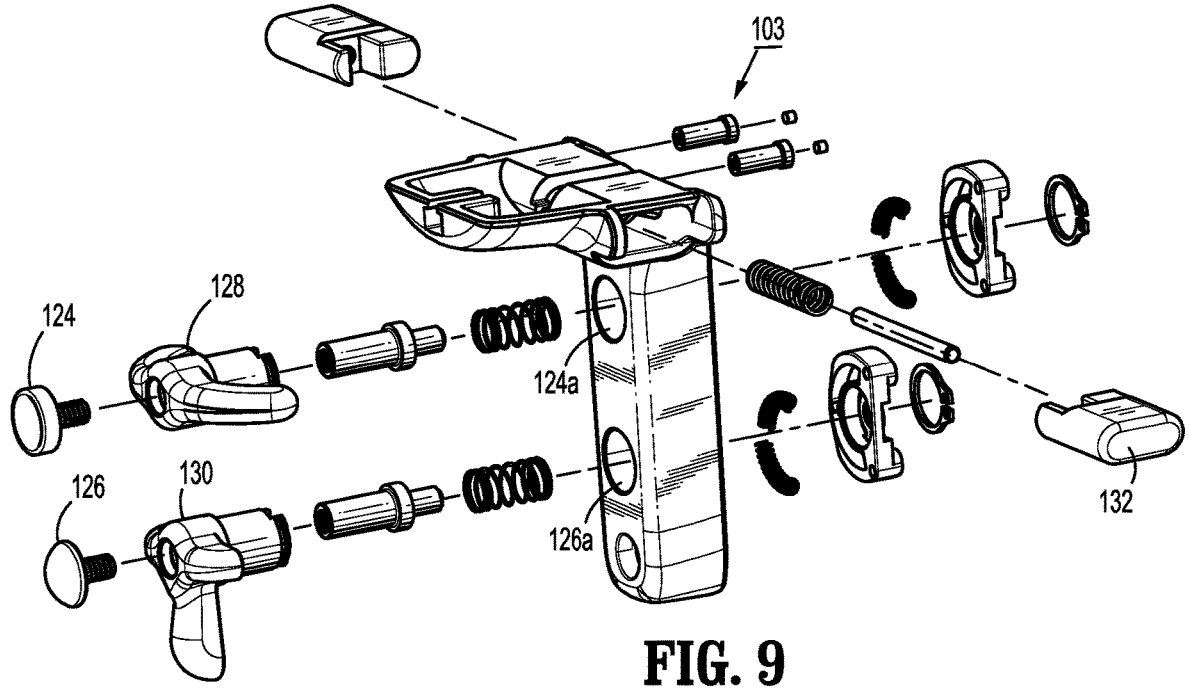
FIG. 9 is a perspective, disassembled view of a control assembly of the surgical instrument of FIG. 1, according to the present disclosure.

As illustrated in FIGS. 6-8, connecting portion 108a of surgical instrument 100 has a cylindrical recess 108b that receives the adapter assembly 200 when adapter assembly 200 is mated to surgical instrument 100. Connecting portion 108a houses three rotatable drive connectors 118, 120, 122.

With reference to FIG. 6, when adapter assembly 200 is mated to surgical instrument 100, each of rotatable drive connectors 118, 120, 122 of surgical instrument 100 couples with a corresponding rotatable connector sleeve 218, 220, 222 of adapter assembly 200. In this regard, the interface between corresponding first drive connector 118 and first connector sleeve 218, the interface between corresponding second drive connector 120 and second connector sleeve 220, and the interface between corresponding third drive connector 122 and third connector sleeve 222 are keyed such that rotation of each of drive connectors 118, 120, 122 of surgical instrument 100 causes a corresponding rotation of the corresponding connector sleeve 218, 220, 222 of adapter assembly 200.

In the above-described embodiments, the hand-held surgical instrument 100 may include a first (e.g., selector) motor 164 that functions to selectively move the selector gearbox assembly 162 gears into engagement with an input drive component having a second (e.g., drive) motor. In embodiments, other motor arrangements may be used, such as a different motor may be used for driving each of the connector sleeves. In further embodiments, other driving mechanisms for actuating the connector sleeves may be used, including, but not limited to, pneumatic and/or hydraulic drivers, solenoids, biasing members, and combinations thereof.

The mating of drive connectors 118, 120, 122 of surgical instrument 100 with connector sleeves 218, 220, 222 of adapter assembly 200 allows rotational forces to be independently transmitted via each of the three respective connector interfaces. The drive connectors 118, 120, 122 of surgical instrument 100 are configured to be independently rotated by drive mechanism 160. In this regard, the function selection module 163 of drive mechanism 160 selects which drive connector or connectors 118, 120, 122 of surgical instrument 100 is to be driven by the input drive component 165 of drive mechanism 160. The selector gearbox assembly 162 and the function selection module 163 are disclosed in more detail in a commonly-owned U.S. patent application Ser. No. 13/280,898, the entire contents of which is hereby incorporated by reference herein.

Since each of drive connectors 118, 120, 122 of surgical instrument 100 has a keyed and/or substantially non-rotatable interface with respective connector sleeves 218, 220, 222 of adapter assembly 200, when adapter assembly 200 is coupled to surgical instrument 100, rotational force(s) are selectively transferred from drive mechanism 160 of surgical instrument 100 to adapter assembly 200.

Figure 12:
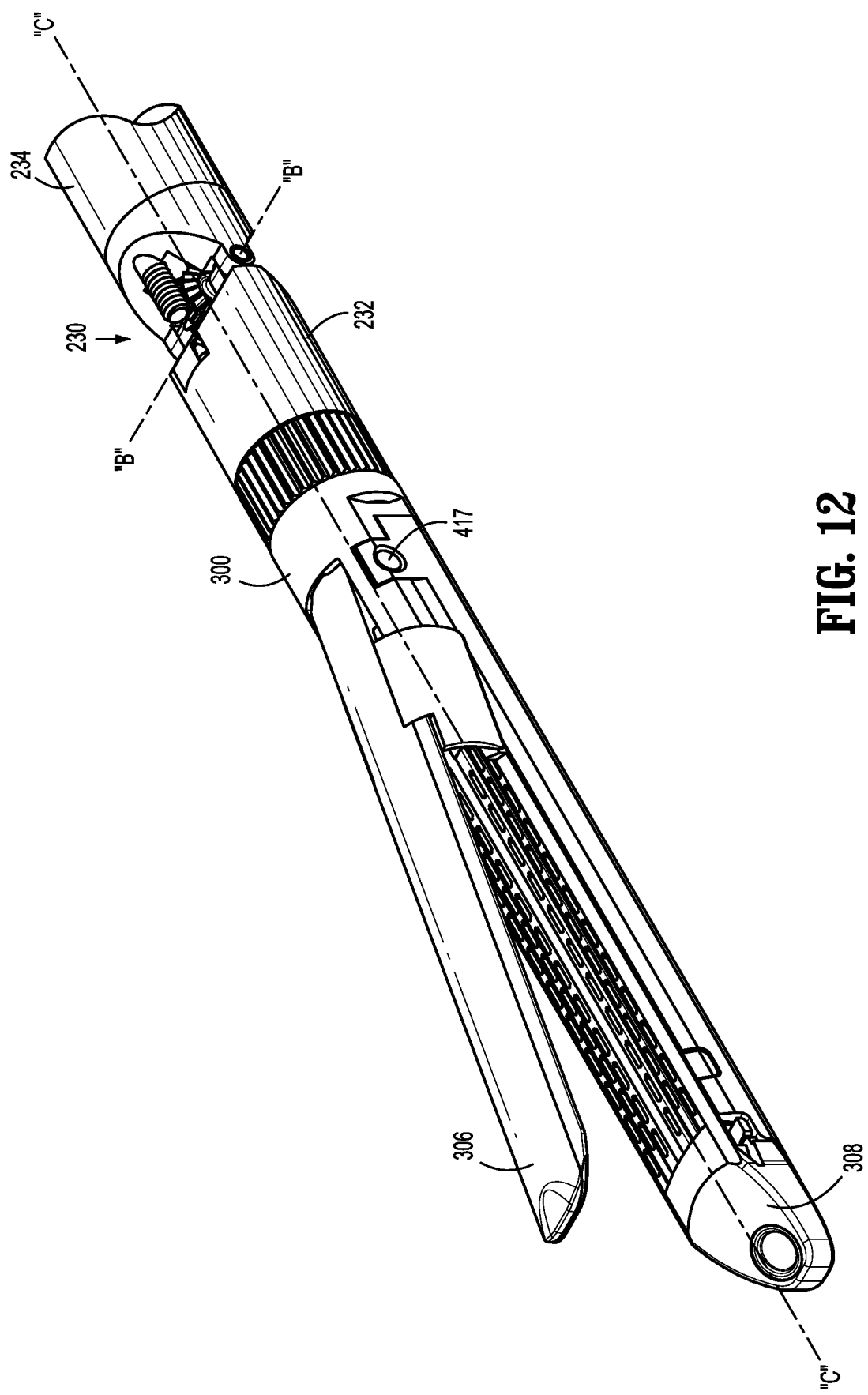
FIG. 12 is a perspective view of an end effector connected to a distal end of the adapter assembly of FIG. 1, oriented in a linear, non-articulated orientation, according to the present disclosure.

The selective rotation of drive connector(s) 118, 120 and/or 122 of surgical instrument 100 allows surgical instrument 100 to selectively actuate different functions of end effector 300. As discussed in greater detail below, selective and independent rotation of first drive connector 118 of surgical instrument 100 corresponds to the selective and independent opening and closing of tool assembly 304 of end effector 300, and driving of a stapling/cutting component of tool assembly 304 of end effector 300. Also, the selective and independent rotation of second drive connector 120 of surgical instrument 100 corresponds to the selective and independent articulation of tool assembly 304 of end effector 300 about an articulation axis "B-B" defined by a pin 505 (FIG. 12) that is transverse to longitudinal axis "A-A" (FIG. 2). In particular, the end effector 300 defines a second longitudinal axis "C-C" and is movable from a first position in which the second longitudinal axis "C-C" (FIG. 12) is substantially aligned with the first longitudinal axis "A-A" to at least a second position in which the second longitudinal axis "C-C" is disposed at a non-zero angle with respect to the first longitudinal axis "A-A." Additionally, the selective and independent rotation of third drive connector 122 of surgical instrument 100 corresponds to the selective and independent rotation of end effector 300 about longitudinal axis "A-A" relative to handle housing 102 of surgical instrument 100.

As illustrated in FIGS. 5 and 8, drive mechanism 160 includes a selector gearbox assembly 162; a function selection module 163, located proximal to the selector gearbox assembly 162, that functions to selectively move gear elements within the selector gearbox assembly 162 into engagement with second motor 166. Thus, drive mechanism 160 selectively drives one of drive connectors 118, 120, 122 of surgical instrument 100 at a given time.

As illustrated in FIGS. 1-3 and FIG. 9, handle housing 102 supports a control assembly 103 on a distal surface or side of intermediate housing portion 108. Control assembly 103, in cooperation with intermediate housing portion 108, supports a pair of finger-actuated control buttons 124, 126 and rocker devices 128, 130. In particular, control assembly 103 defines an upper aperture 124a for slidably receiving a first control button 124, and a lower aperture 126b for slidably receiving a second control button 126.

Each one of the control buttons 124, 126 and rocker devices 128, 130 includes a respective magnet (not shown) that is moved by the actuation of an operator. In addition, circuit board 150 includes, for each one of the control buttons 124, 126 and rocker devices 128, 130, respective Hall-effect switches 150a-150d that are actuated by the movement of the magnets in the control buttons 124, 126 and rocker devices 128, 130. In particular, located immediately proximal to the control button 124 is a first Hall-effect switch 150a (FIGS. 3 and 7) that is actuated upon the movement of a magnet within the control button 124 upon the operator actuating control button 124. The actuation of first Hall-effect switch 150a, corresponding to control button 124, causes circuit board 150 to provide appropriate signals to function selection module 163 and input drive component 165 of the drive mechanism 160 to close a tool assembly 304 of end effector 300 and/or to fire a stapling/cutting cartridge within tool assembly 304 of end effector 300.

Also, located immediately proximal to rocker device 128 is a second Hall-effect switch 150b (FIGS. 3 and 7) that is actuated upon the movement of a magnet (not shown) within rocker device 128 upon the operator actuating rocker device 128. The actuation of second Hall-effect switch 150b, corresponding to rocker device 128, causes circuit board 150 to provide appropriate signals to function selection module 163 and input drive component 165 of drive mechanism 160 to articulate tool assembly 304 relative to the adapter assembly 200. Advantageously, movement of rocker device 128 in a first direction causes tool assembly 304 to articulate relative to the adapter assembly 200 in a first direction, while movement of rocker device 128 in an opposite, e.g., second, direction causes tool assembly 304 to articulate relative to the adapter assembly 200 in an opposite, e.g., second, direction.

Furthermore, located immediately proximal to control button 126 is a third Hall-effect switch 150c (FIGS. 3 and 7) that is actuated upon the movement of a magnet (not shown) within control button 126 upon the operator actuating control button 126. The actuation of third Hall-effect switch 150c, corresponding to control button 126, causes circuit board 150 to provide appropriate signals to function selection module 163 and input drive component 165 of drive mechanism 160 to open tool assembly 304 of end effector 300.

In addition, located immediately proximal to rocker device 130 is a fourth Hall-effect switch 150d (FIGS. 3 and 7) that is actuated upon the movement of a magnet (not shown) within rocker device 130 upon the operator actuating rocker device 130. The actuation of fourth Hall-effect switch 150d, corresponding to rocker device 130, causes circuit board 150 to provide appropriate signals to function selection module 163 and input drive component 165 of drive mechanism 160 to rotate end effector 300 relative to handle housing 102 surgical instrument 100. Specifically, movement of rocker device 130 in a first direction causes end effector 300 to rotate relative to handle housing 102 in a first direction, while movement of rocker device 130 in an opposite, e.g., second, direction causes end effector 300 to rotate relative to handle housing 102 in an opposite, e.g., second, direction.

Figure 10:
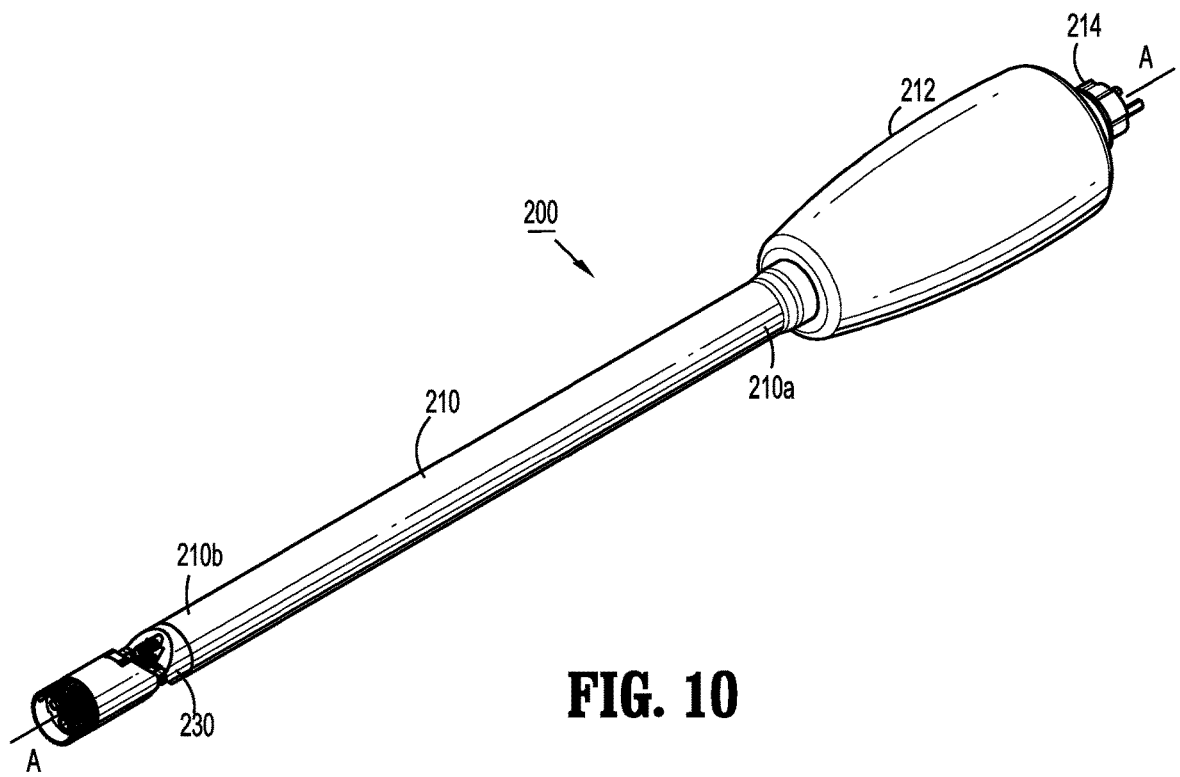
FIG. 10 is a perspective view of the adapter assembly of FIG. 1 having an articulating neck assembly, according to the present disclosure.

Turning now to FIGS. 1 and 10, adapter assembly 200 will be shown in detail and described. Adapter assembly 200 is configured to communicate the rotational forces of first, second and third rotatable drive connectors 118, 120, and 122 of surgical instrument 100 to end effector 300. As mentioned above, adapter assembly 200 is configured for selective connection to surgical instrument 100.

As seen in FIGS. 1, 6, 10, and 11 adapter assembly 200 includes an elongate, substantially rigid, elongate body portion 210 having a proximal end 210a and a distal end 210b; a transmission housing 212 connected to proximal end 210a of elongate body portion 210 and being configured for selective connection to surgical instrument 100. The adapter assembly 200 also includes an articulating assembly 230 disposed at the distal end 210b for coupling to the end effector 300.

In embodiments, the transmission housing 212 may include one or more gear train systems therein for varying a speed/force of rotation (e.g., increase or decrease) of first, second and/or third rotatable drive connectors 118, 120, and/or 122 of surgical instrument 100 before transmission of such rotational speed/force to end effector 300.

Transmission housing 212 of adapter assembly 200 is configured and adapted to connect to connecting portion 108a of upper housing portion 108 of surgical instrument 100. As seen in FIGS. 1 and 6, transmission housing 212 of adapter assembly 200 includes a shaft coupling assembly 214 supported at the proximal end 210a.

Adapter assembly 200 may include a first gear train system and a second gear train system, each disposed within transmission housing 212 and elongate body portion 210. Each gear train system is configured and adapted to vary a speed/force of rotation (e.g., increase or decrease) of first and second rotatable drive connectors 118 and 120 of surgical instrument 100 before transmission of such rotational speed/force to end effector 300. An adapter assembly having multiple gear trains is disclosed in more detail in a commonly-owned U.S. patent application Ser. No. 13/280, 898, the entire contents of which is hereby incorporated by reference herein.

Figure 11:
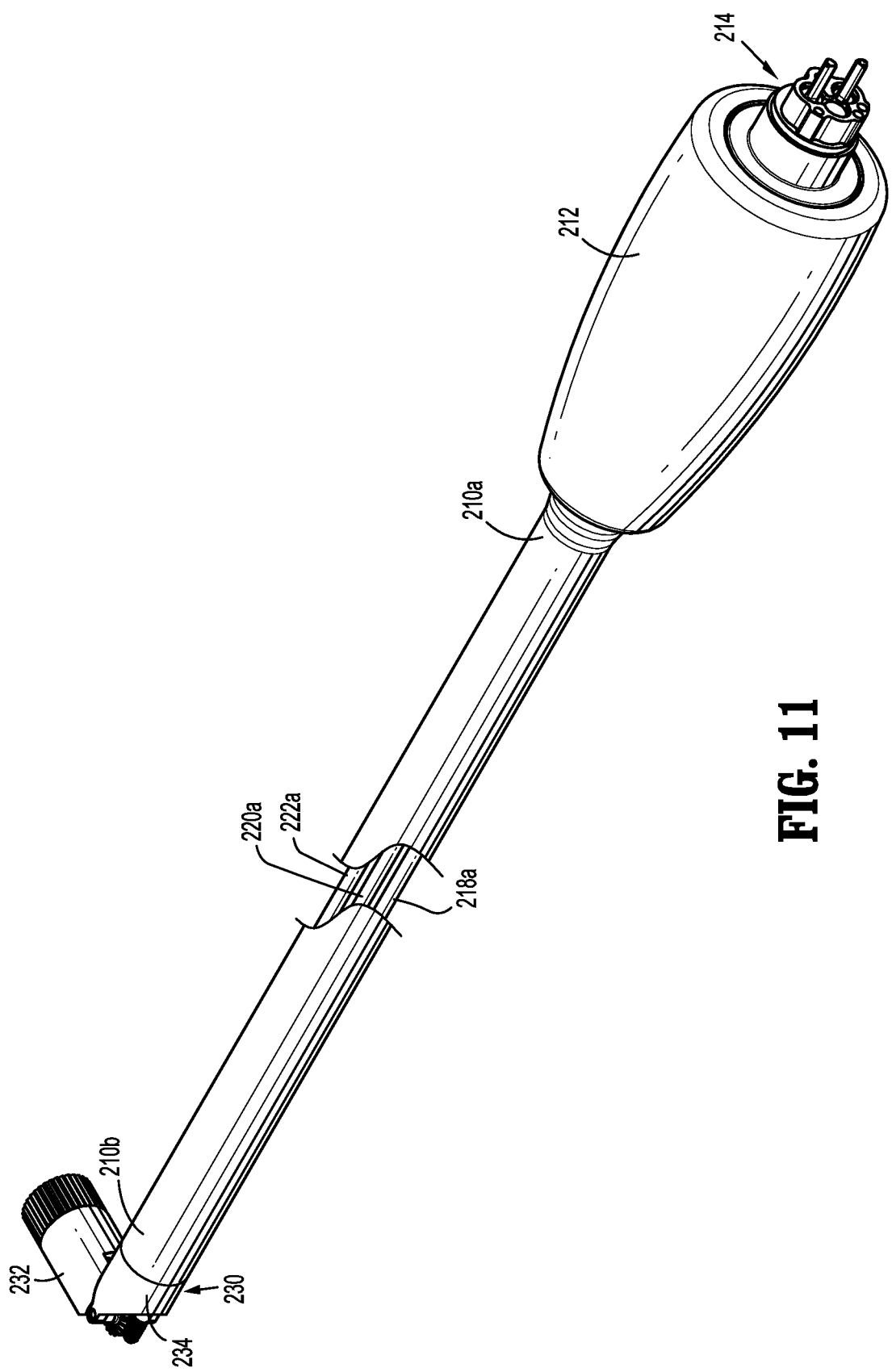
FIG. 11 is a perspective, partial cross-sectional view of the adapter assembly of FIG. 1, according to the present disclosure.

As seen in FIG. 11, adapter assembly 200 may rotatably support first, second, and third drive shafts 218a, 220a, 222a, which include a proximal end connected to transmission housing 212, namely, corresponding rotatable connector sleeve 218, 220, 222. Each of the drive shafts 218a, 220a, 222a also include a distal end extending to and operatively connected to the articulating assembly 230, as will be discussed in greater detail below. The elongate body portion 210 of adapter assembly 200 includes at least three longitudinally extending channels through body portion 210. The channels are configured and dimensioned to rotatably receive and support the drive shafts 218a, 220a, 222a, which may be connected to respective gear systems (not shown). Each of the drive shafts 218a, 220a, 222a are elongate and sufficiently rigid to transmit rotational forces from transmission housing 212 to articulating assembly 230, which are used to drive the end effector 300 as described in further detail below.

FIGS. 12-16 illustrate components and operation of the end effector 300. End effector 300 includes a pair of jaw members, which include a cartridge assembly 308 and an anvil 306. Cartridge assembly 308 houses one or more fasteners 433 (FIG. 13) that are disposed therewithin and is configured to deploy the fasteners 433 upon firing of instrument 100. The anvil 306 is movably (e.g., pivotally) mounted to the end effector 300 and is movable between an open position, spaced apart from cartridge assembly 308, and a closed position wherein anvil 306 is in close cooperative alignment with cartridge assembly 308, to thereby clamp tissue.

Figure 13:
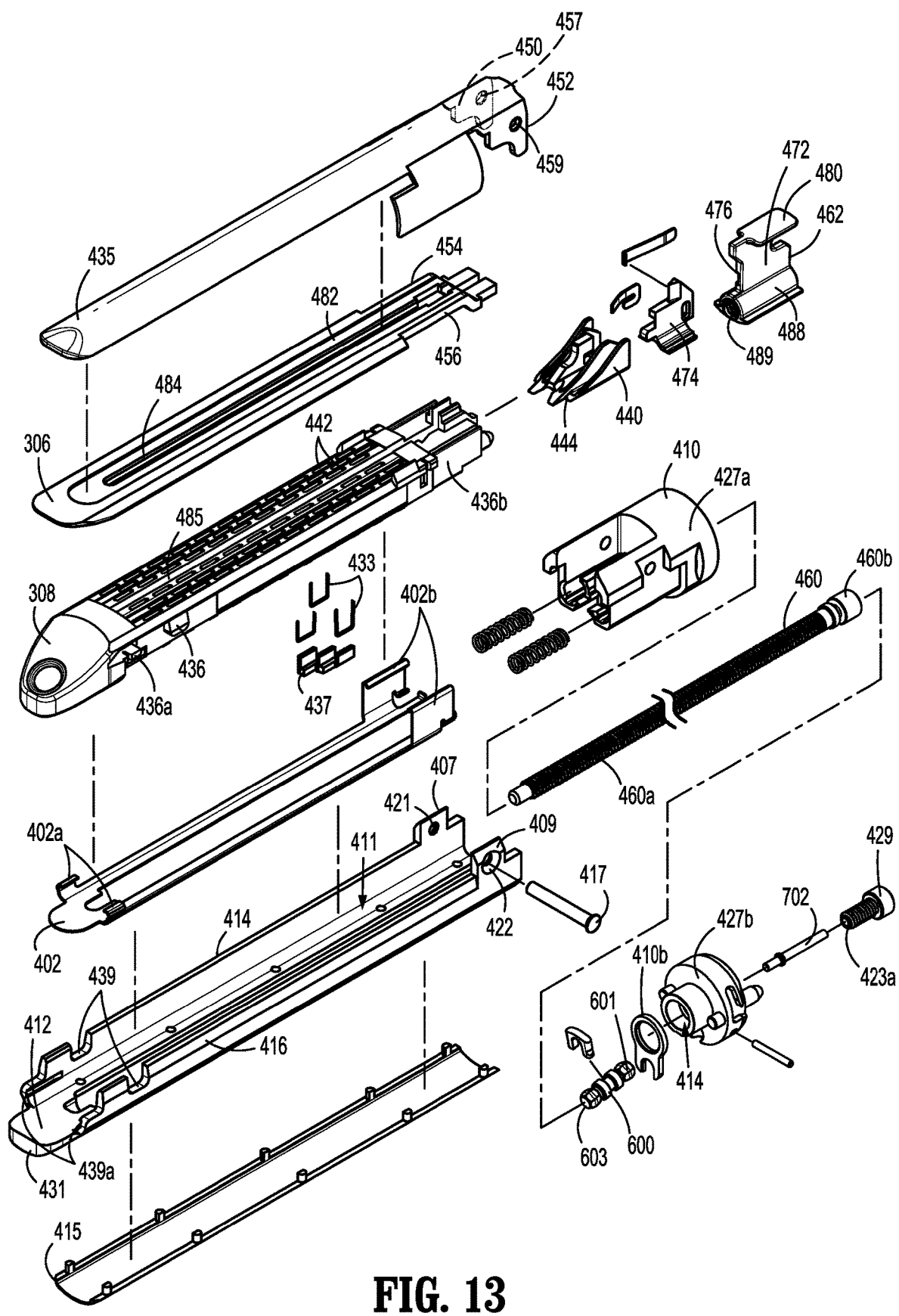
FIG. 13 is a disassembled view of the end effector of FIG. 12, according to the present disclosure.

Referring to FIG. 13, a disassembled view of the end effector 300 is shown. The end effector 300 also includes a carrier 431 having an elongate channel 411, a base 412 and two parallel upstanding walls 414 and 416 which include several mounting structures, such as notches 439, for supporting the cartridge assembly 308 and the anvil 306. A longitudinal slot 413 extends through the elongate channel 411.

The carrier 431 also includes a plate cover 415 disposed on a bottom surface thereof. The plate cover 415 is configured to frictionally engage with channel 411 of the carrier 431 and functions to protect tissue from moving parts along the exterior of carrier 431. The carrier 431 also includes a pair of tabs 407 and 409 disposed at a proximal end of respective walls 414, 416, and being configured for coupling to a housing portion 410 of end effector 300.

The carrier 431 also includes a holder plate 402 disposed on a top surface thereof. The holder plate 402 is configured to frictionally engage the carrier 431 and the cartridge assembly 308 to secure the fasteners 433 and pushers 437 therein. The holder plate 402 includes a pair of distal wings 402a and a pair of proximal wings 402b configured to engage distal tabs 436a and proximal tabs 436b of the cartridge assembly 308, respectively. The distal wings 402a of the holder plate 402 are also configured and dimensioned to engage slots 439a disposed at a distal end of the carrier 431 thereby securing the cartridge assembly 308 to the carrier 431.

With continuing reference to FIG. 13, the distal portion of channel 411 supports the cartridge assembly 308 which contains the plurality of surgical fasteners 433 and a plurality of corresponding ejectors or pushers 437. End effector 300 includes an actuation sled 440 having upstanding cam wedges 444 configured to exert a fastener driving force on the pushers 437, which drive the fasteners 433 from cartridge assembly 308, as described in more detail below. Cartridge assembly 308 is maintained within channel 411 by lateral struts 436 which frictionally engage corresponding notches 439 formed in the upper surfaces of channel walls 414 and 416. These structures serve to restrict lateral, longitudinal, and elevational movement of the cartridge assembly 308 within channel 411. In any of the embodiments disclosed herein, the cartridge assembly 308 can be removable and replaceable so that the end effector 300 can be reused within a particular surgery allowing for multiple firings of a single end effector 300.

A plurality of spaced apart longitudinal slots (not shown) extend through cartridge assembly 308 and accommodate the upstanding cam wedges 444 of actuation sled 440. The slots communicate with a plurality of pockets 442 within which the plurality of fasteners 433 and pushers 437 are respectively supported. The pushers 437 are secured by a pusher retainer (not shown) disposed below the cartridge assembly 308, which supports and aligns the pushers 437 prior to engagement thereof by the actuation sled 440.

During operation, as actuation sled 440 translates through cartridge assembly 308, the angled leading edges of cam wedges 444 sequentially contact pushers 437 causing the pushers to translate vertically within slots 446, urging the fasteners 306 therefrom. The cartridge assembly 308 also includes a longitudinal slot 485 to allow for a knife blade 474 to travel therethrough, as described in more detail below.

Figure 14:
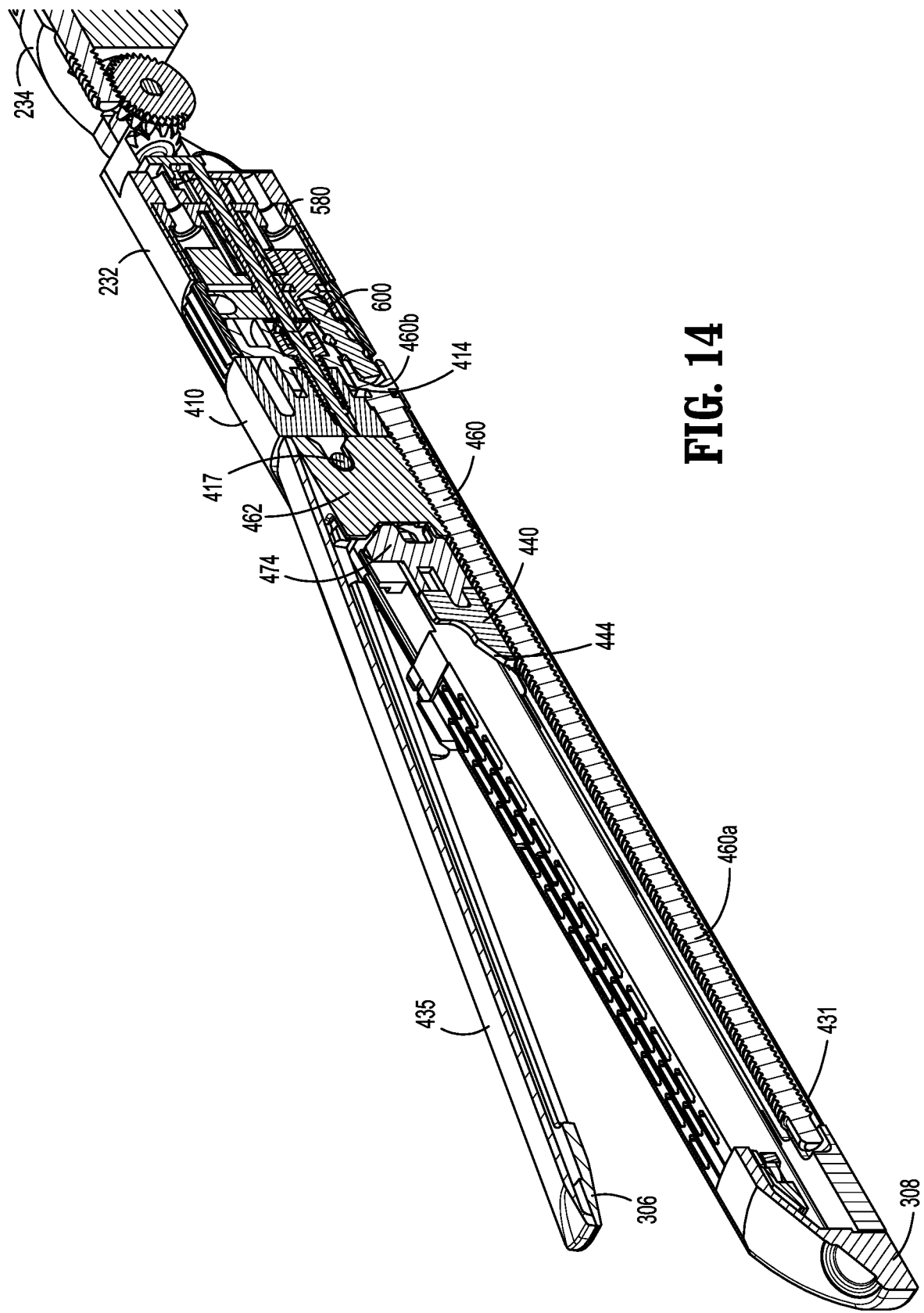
FIG. 14 is a perspective, cross-sectional view of the end effector of FIG. 12, according to the present disclosure.

With continuing reference to FIGS. 13 and 14, the end effector 300 includes an anvil cover 435 disposed over the anvil 306. The anvil cover 435 protects tissue from moving parts along the exterior of anvil 306. The anvil cover 435 includes opposed mounting wings 450 and 452 which are dimensioned and configured to engage detents 454 and 456 of the anvil 306, respectively. The mounting wings 450 and 452 function to align the anvil 306 with the cartridge assembly 308 during closure. The anvil 306 and the cover 435 are configured to remain in an open configuration until closed, as described in more detail below.

The anvil 306 is pivotally coupled to the carrier 431. The carrier 431 includes a pair of openings 421 and 422 formed in respective tabs 407, 409. The anvil cover 435 also includes a pair of opposed openings 457 and 459 found therein. A pivot pin 417, or a pair of pins, passes through the openings 421, 422, 457, and 459 allowing for pivotal coupling of the anvil 306 to the carrier 431 and the cartridge assembly 308.

As seen in FIGS. 13 and 14, end effector 300 further includes an axial drive screw 460 for transmitting the rotational drive forces exerted by the second drive shaft 220a, as described in further detail below, to actuation sled 440 during a stapling procedure. Drive screw 460 is rotatably supported in carrier 431 and includes a threaded portion 460a and a proximal engagement portion 460b. The drive screw 460 is rotatably secured by a thrust plate 410b within the distal housing member 410 such that the drive screw 460 may be rotated relative to the carrier 431. Distal housing member 410 of the end effector 300 is coupled to the proximal end of the carrier 431 via pivot pin 417. The housing member 410 includes a bore 414 (FIG. 14) defined therethrough that houses the engagement portion 460b therein. The distal tip of the drive screw 460 rests in a recess defined in the channel 411 of the carrier 431.

Figure 15:
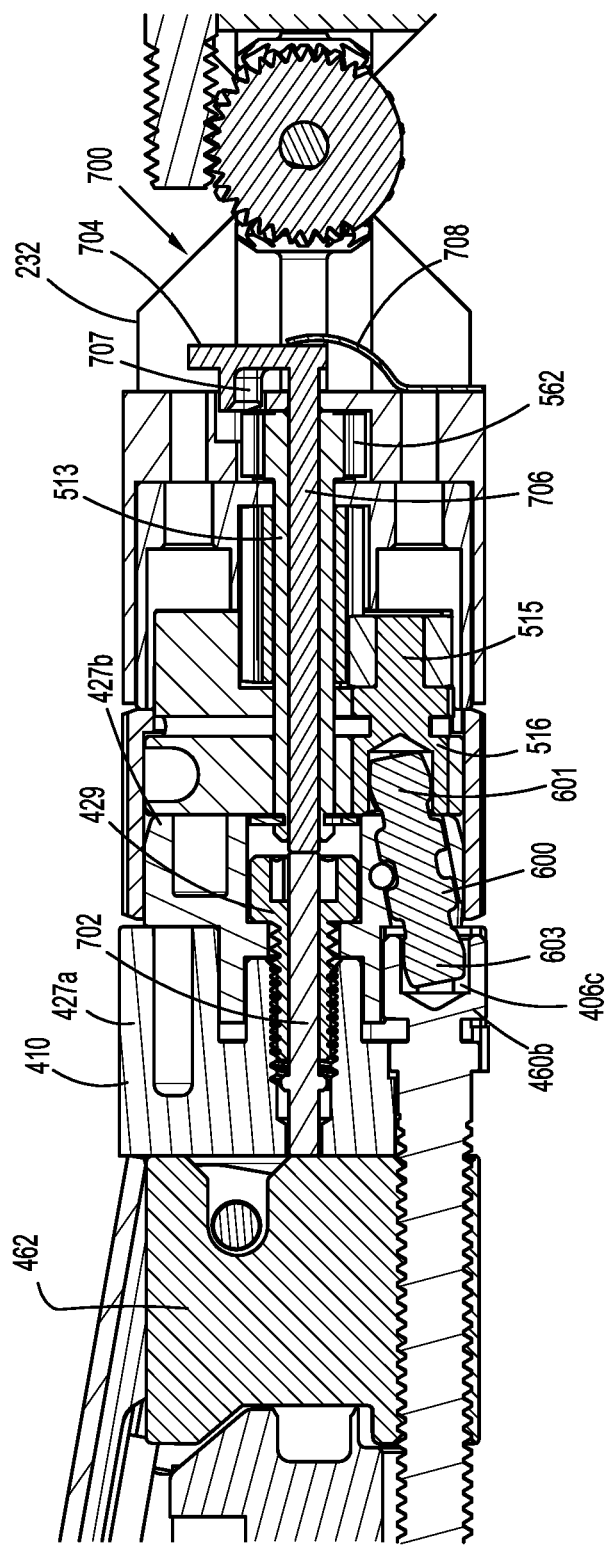
FIG. 15 is an enlarged, cross-sectional side view of the end effector of FIG. 12, according to the present disclosure.

As shown in FIGS. 13-15, the drive screw 460 is coupled to a drive linkage 600, which mechanically engages the second drive shaft 220a, as described in further detail below, and the drive screw 460 of end effector 300. The drive linkage 600, disposed within the housing portion 410, is off-axis with respect to the drive screw 460. In particular, the longitudinal axis defined by the drive linkage 600 is at a non-parallel (e.g., non-zero angle) angle with respect to a longitudinal axis defined by the drive screw 460. In embodiments, the drive linkage 600 may be disposed along the same longitudinal axis as the drive screw 460.

With reference to FIG. 15, the drive linkage 600 includes a proximal engagement portion 601 and a distal engagement portion 603. The proximal engagement portion 601 is configured to be engaged by a coupling member 515, and the distal engagement portion 603 is dimensioned and configured to engage the proximal engagement portion 460b of drive screw 460. In particular, the engagement portion 601 includes a faceted surface, which is configured and dimensioned to interface with a socket 516 of the coupling member 515, which has a corresponding faceted surface. The engagement portion 603 also includes a faceted surface, which is configured and dimensioned to interface with a socket 460c of the engagement portion 460b, which has a corresponding faceted surface. The mechanical coupling of the engagement portions 601 and 603 with the sockets 516 and 460c, respectively, occurs via abutment of the male faceted surfaces of the engagement portions 601 and 603 with corresponding female faceted socket 516 and 460c, which allows for transfer of rotational motion of the coupling member 515 to the drive linkage 600 and, in turn, to the drive screw 460. In embodiments, the drive linkage 600 may mechanically interface with the drive screw 460 and the coupling member 515 using any other suitable mechanical coupling, e.g., pinned.

With reference to FIGS. 13 and 14, end effector 300 further includes a drive beam 462 disposed within carrier 431. The drive beam 462 includes a vertical support strut 472 and an abutment surface 476, which engages the knife blade 474, which in turn, engages the actuation sled 440. The drive beam 462 also includes a cam member 480 disposed on top of the vertical support strut 472. Cam member 480 is dimensioned and configured to engage and translate with respect to an exterior camming surface 482 of anvil 306 to progressively clamp the anvil 306 against body tissue during firing.

A longitudinal slot 484 extends through the anvil 306 to accommodate the translation of the vertical strut 472. This allows the cam member 480 to travel in between the cover 435 and anvil 306 during firing. In embodiments, the anvil cover 435 may also include a corresponding longitudinal slot (not shown) formed on an underside thereof and is secured to an upper surface of anvil 306 to form a channel therebetween.

The drive beam 462 includes a retention portion 488 having a threaded bore 489 defined therethrough. The drive screw 460 is threadably coupled to the retention portion 480 through the bore 489, such that as the drive screw 460 is rotated, the drive beam 462 travels in a longitudinal direction along the longitudinal axis defined by the drive screw 460.

In use, as the drive screw 460 is rotated in a clock-wise direction, the drive beam 462 travels in a distal direction closing the anvil 306 as the cam member 480 pushes down on the camming surface 482 thereof. The drive beam 462 also pushes the sled 440 in the distal direction, which then engages the pushers 437 via the cam wedges 444 to eject the fasteners 433. The drive beam 462 may be made of any suitable first material including, but not limited to, plastics, metals, and combinations thereof. The first and second materials may be either same or different.

The knife blade 474 travels slightly behind actuation sled 440 during a stapling procedure to form an incision between the rows of fastener body tissue. As the drive beam 462 is driven in the distal direction, the abutment surface 476 of the vertical strut 472 pushes the knife blade 474, which then pushes sled 440 in the distal direction to eject the fasteners 433 and simultaneously dissect tissue with the knife blade 474. The knife blade 474 and the drive beam 462 travel through the longitudinal slots 484 and 485. The drive beam 462 closes the anvil as it is driven in the distal direction and also pushes the sled 440, which, in turn, ejects the fasteners 433 ahead of the knife blade 474. As the fasteners 433 are ejected they are deformed again the tissue-contacting (e.g., underside) surface of the anvil 306 having a plurality of anvil pockets (not shown).

With reference to FIGS. 11, 12, and 14-17A, the articulating assembly 230 is shown. The assembly 230 includes a distal joint member 232 for coupling to a proximal end of the end effector 300 and a proximal joint member 234 coupled to the distal end 210b of the body portion 210.

With reference to FIGS. 13 and 16-21 the housing portion 410 of the end effector 300 includes one or more posts 410a for insertion into one or more corresponding bores 580a within a socket 580. The socket 580 is rotationally disposed within the joint member 232. In particular, the socket 580 is disposed within a spacer 232a and includes a textured ring 232b disposed on an outer surface thereof. This allows the socket 580 to be rotated about the longitudinal axis "C-C" (FIG. 12) by a shaft 513 that is longitudinally arranged within the joint member 232, as described in further detail below.

Figure 16:
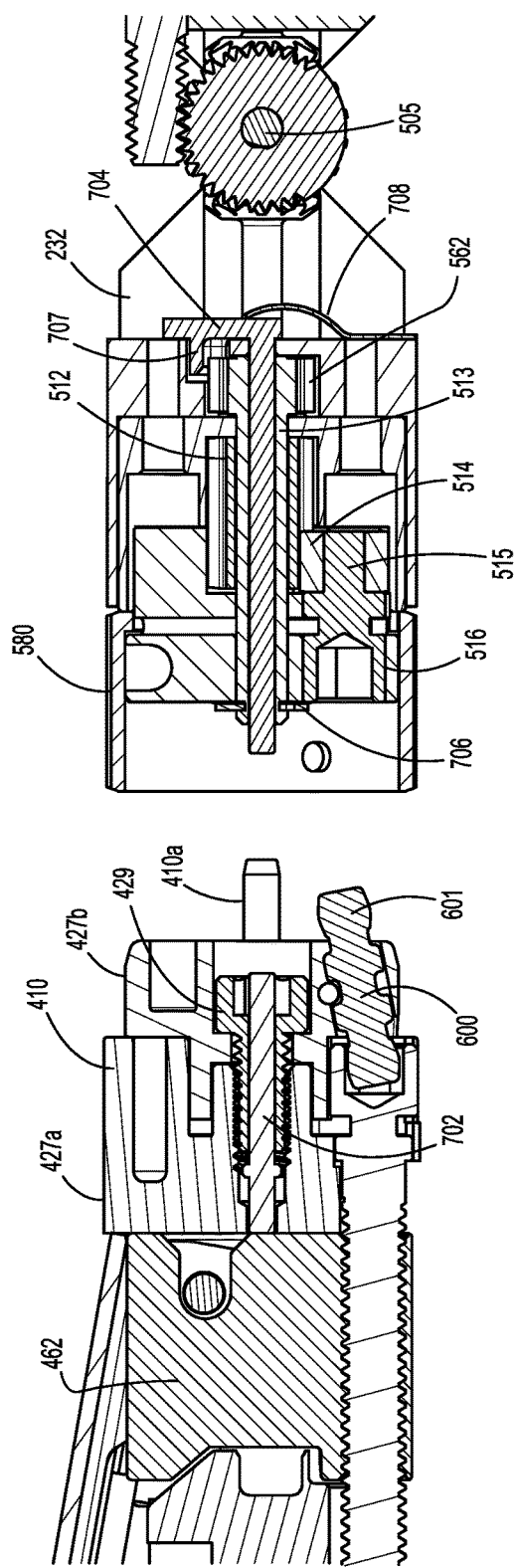
FIG. 16 is an enlarged, cross-sectional side view of the end effector of FIG. 12 disconnected from the articulating neck assembly, according to the present disclosure.

The shaft 513 includes one or more facets 513a such that the shaft 513 is keyed to a central bore 580b of the socket 580. This allows for rotation of the socket 580 along with the shaft 513. As shown in FIG. 16, during insertion the proximal engagement portion 601 of the drive linkage 600 also engages the socket 516 of the coupling member 515, which actuates the drive screw 460 as described in further detail below.

Figures 17A, 17B:
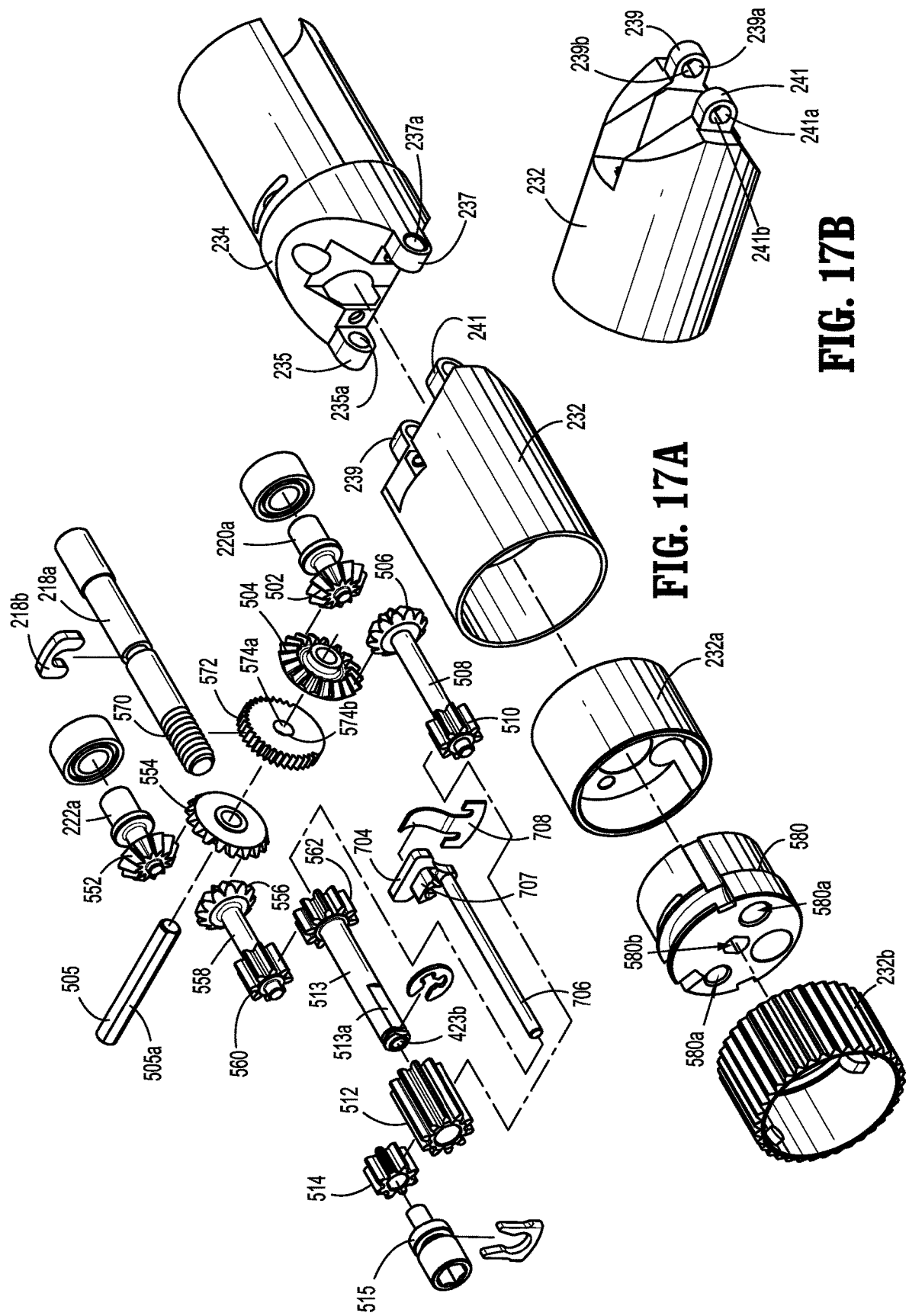
FIG. 17A is a disassembled view of the articulating neck assembly according to the present disclosure.
FIG. 17B is a perspective view of part of the articulating neck assembly according to the present disclosure.
Figure 22:
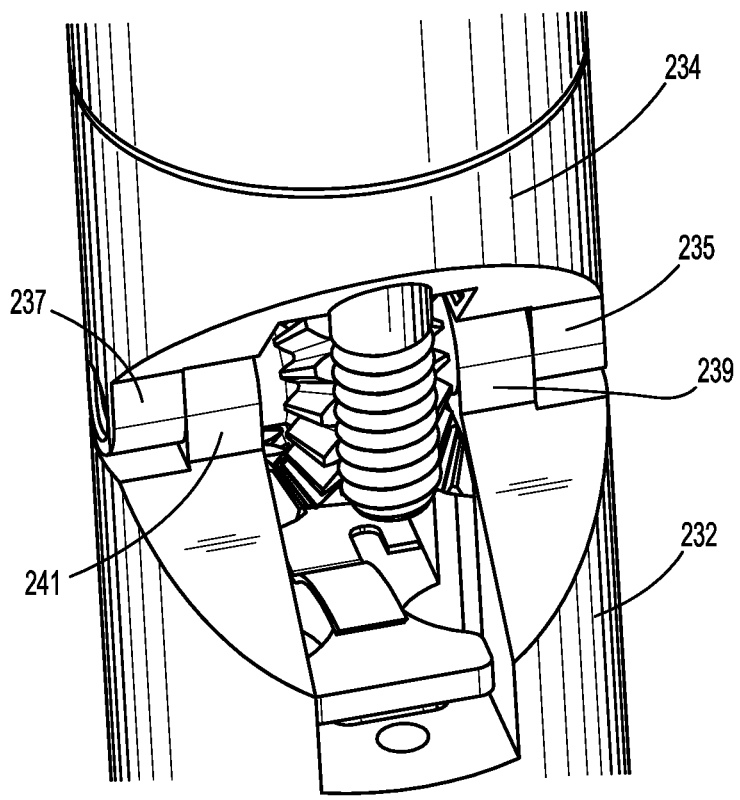
FIG. 22 is a top perspective view of the articulating neck assembly according to the present disclosure.

With reference to FIGS. 17A-19, the proximal joint member 234 and the distal joint member 232 are configured and dimensioned as a clevis to interface with a pin 505. The pin 505 includes one or more longitudinal facets 505a along at least a portion of the pin 505. The proximal joint member 234 of the neck assembly 230 includes a pair of opposing arms 235, 237 including a pair of opposing circular bores 235a, 237a, respectively, allowing the pin 505 to be rotationally coupled within the bores 235a, 237a of opposing arms 235, 237. With reference to FIGS. 17A-B, the joint member 232 of the assembly 230 also includes a pair of opposing arms 239, 241 including a pair of opposing bores 239a, 241a. With reference to FIG. 17B, each of the bores 239a, 241a includes a facet 239b, 241b, such that when the pin 505 is inserted into the bores 235a, 237a, 239b, 241b, the pin 505 can rotate freely within the bores 235a, 237a. This secures the joint member 232 to the pin 505 about the bores 239a, 241a via mating of the facet 505a of the pin 505 with the facets 239b, and 241b. Since the pin 505 is keyed to the bores 239a, 241a of the joint member 232 and is free-floating within the bores 235a, 237a of the proximal joint member 234, the joint member 232 along with the end effector 300 may be freely rotated with respect to the proximal joint member 234 about a articulation axis "B-B" (FIG. 12) defined by the pin 505 as shown in FIG. 22 and described in further detail below.

Figure 18:
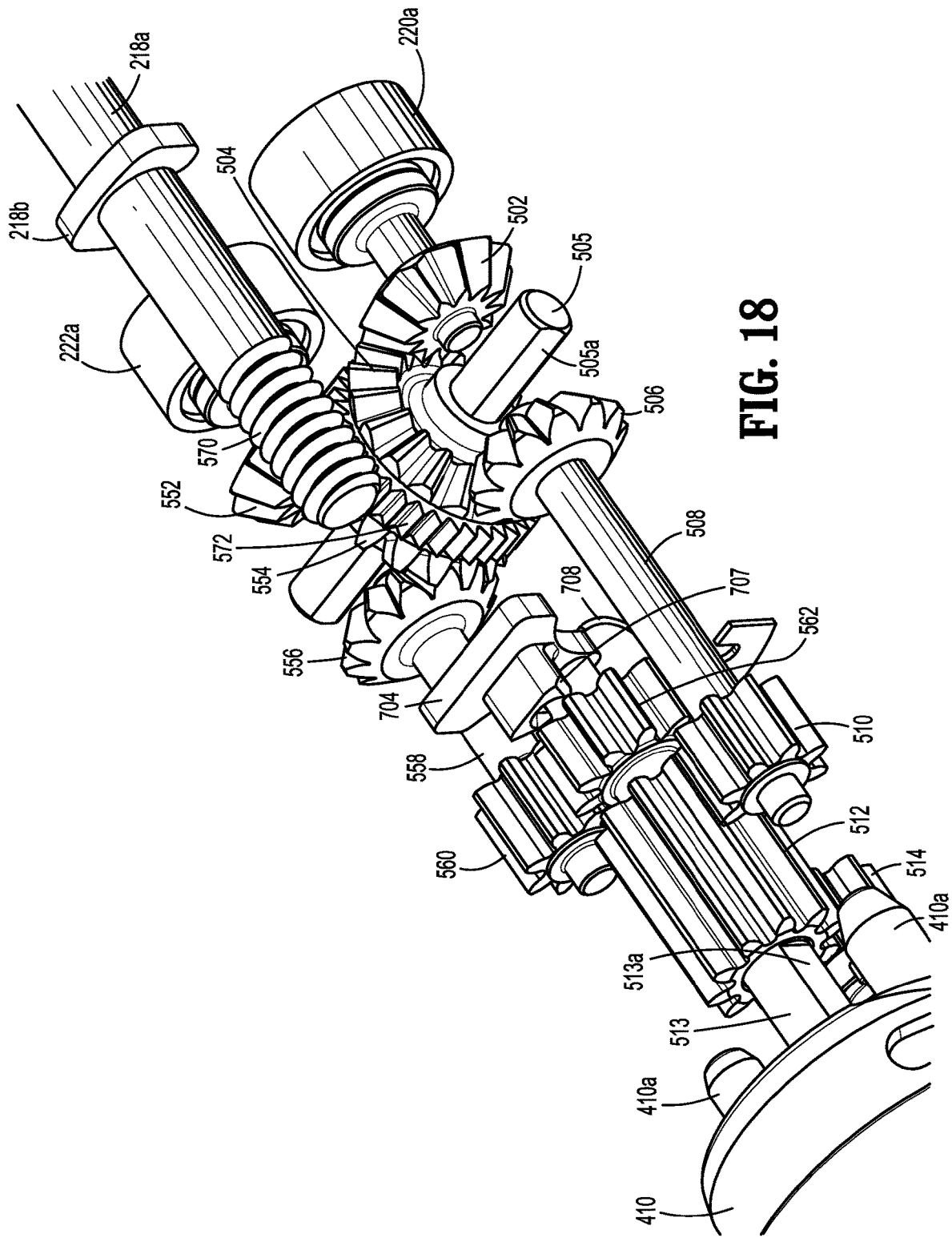
FIG. 18 is a top perspective, partially-disassembled view of the articulating neck assembly according to the present disclosure.
Figure 19:
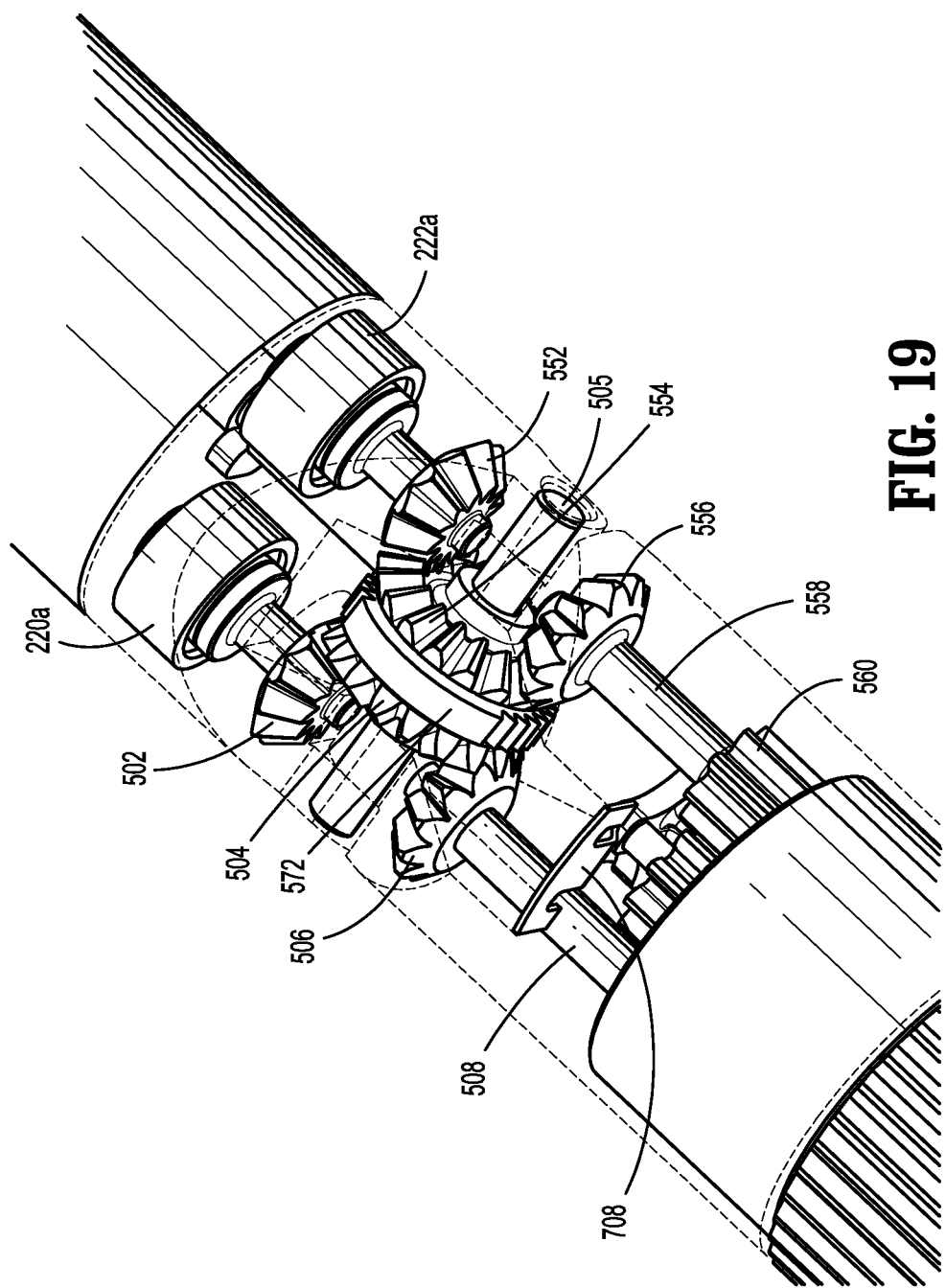
FIG. 19 is a bottom perspective, partially-disassembled view of the articulating neck assembly according to the present disclosure.
Figure 20:
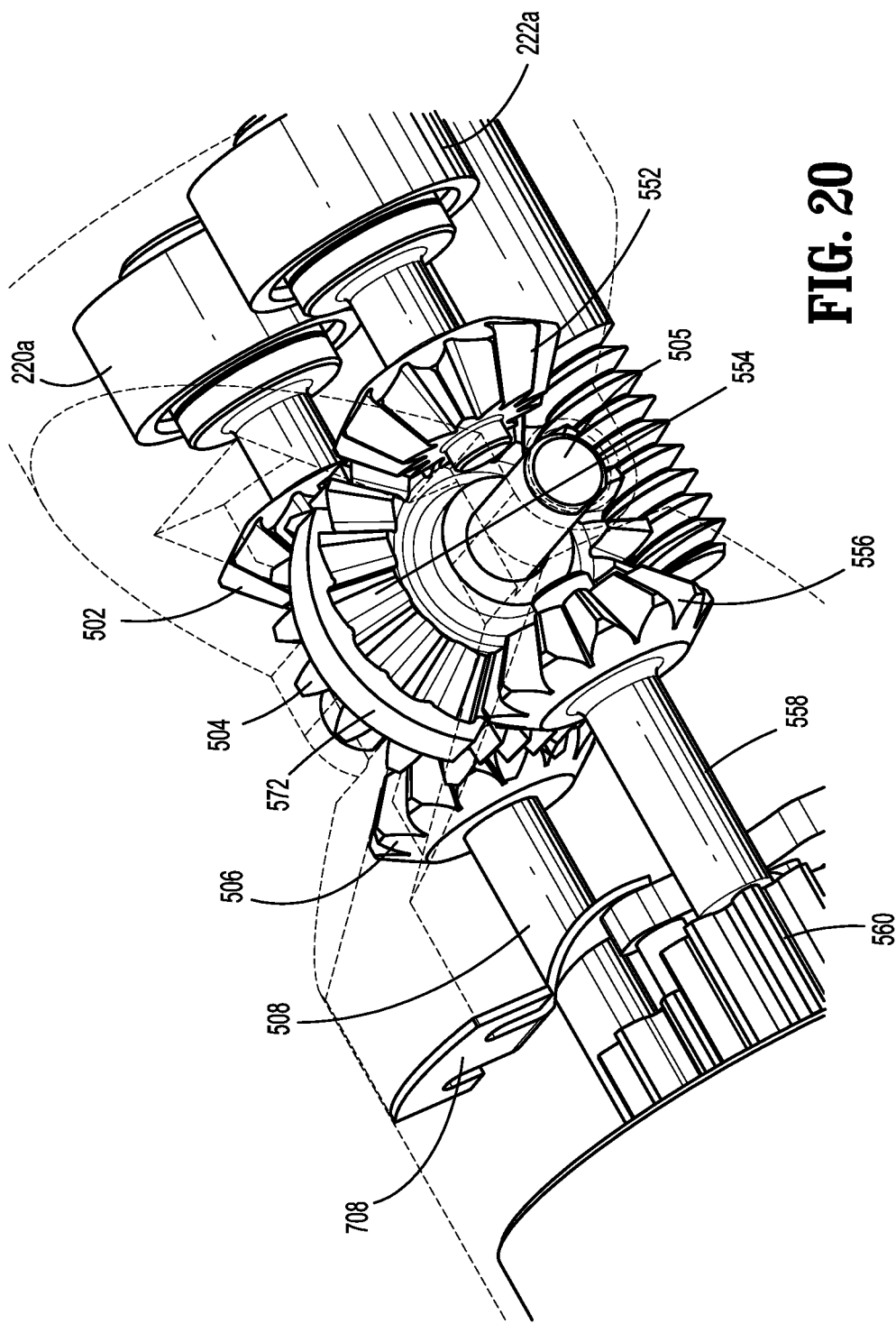
FIG. 20 is a side perspective, partially-disassembled view of the articulating neck assembly according to the present disclosure.
Figure 21:
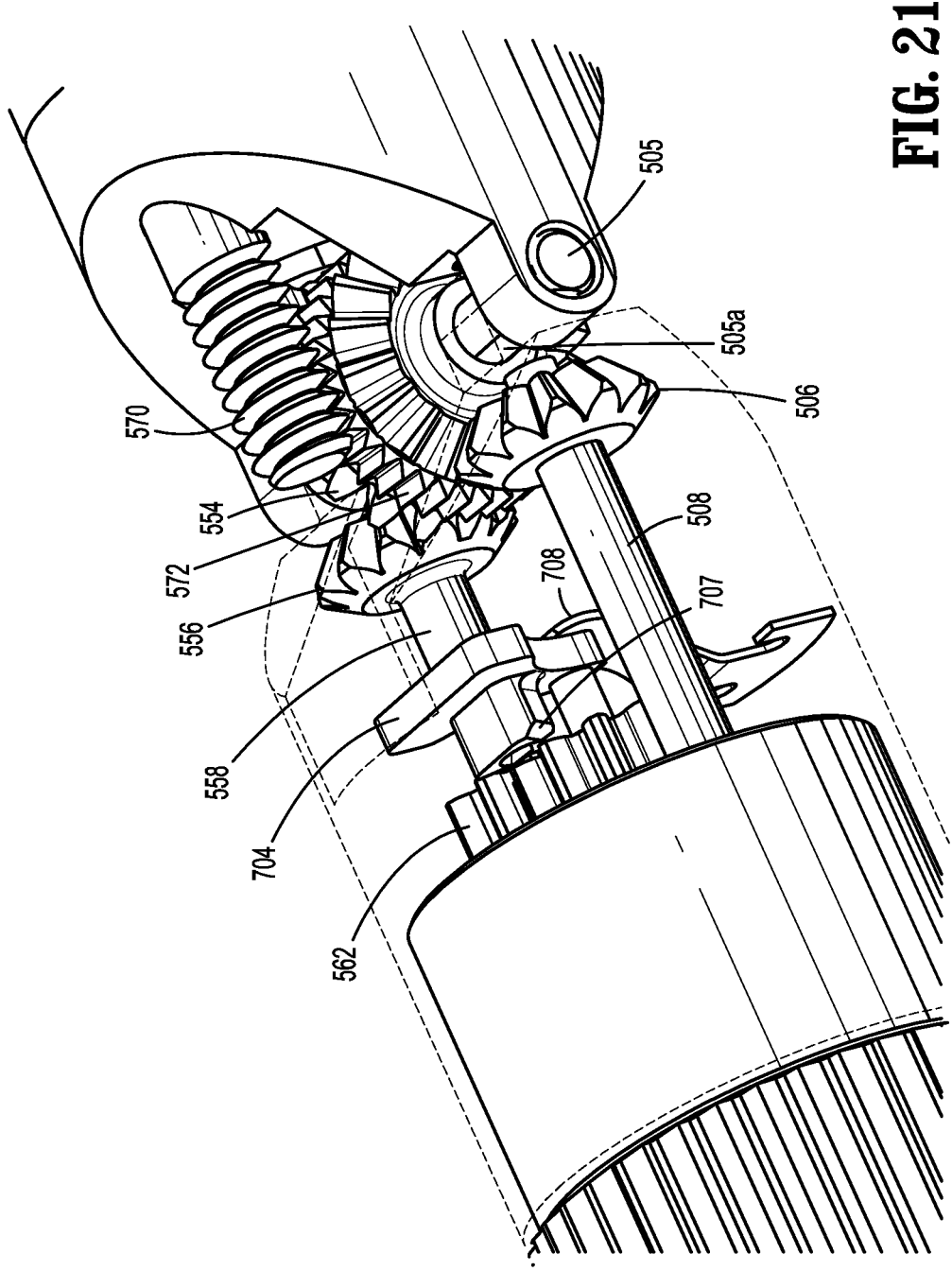
FIG. 21 is a top perspective, partially-disassembled view of the articulating neck assembly according to the present disclosure.

With reference to FIGS. 17A and 18, the assembly 230 also includes the second (e.g., actuating/firing) drive shaft 220a, which may be axially rotatable within the body portion 210. The drive shaft 220a includes a second gear element 502 coupled thereto and configured to rotate therewith about a longitudinal axis defined by the drive shaft 220a. The gear element 502 is meshingly engaged with a first transfer gear element 504. The gear element 504 is held in position by the pin 505 and is configured to rotate about the pin 505.

The gear element 504 is also meshingly engaged with a gear element 506 within the joint member 232. The gear elements 502, 504, 506 are bevel gears allowing for meshing engagement thereof even as the joint member 232 and the end effector 300 are pivoted with respect to the body portion 210. The gear element 502 rotates about a longitudinal axis parallel with the axis "A-A." The gear element 504 rotates about the axis "B-B" (FIG. 12) and the gear element 506 rotates about a longitudinal axis parallel with the axis "C-C" (FIGS. 2 and 10). The gear element 506 is connected to a gear element 510 by a shaft 508. The gear element 506, the gear element 510, and the shaft 508 rotate within the joint member 232 about a longitudinal axis defined by the central axis of the shaft 508. The gear element 510 is, in turn, meshingly engaged with a gear element 512 that rotates about the shaft 513 that is longitudinally arranged within the joint member 232. The gear element 512 is meshingly engaged with a gear element 514 of the coupling member 515. The coupling member 515 includes a shaft portion that extends distally to the socket 516, which is coupled to drive linkage 600 as described above. Rotation of the drive shaft 220a results in rotation of the gear elements 502, 504, 506, 510, 512, 514 and the socket 516, which in turn, rotates the drive screw 460 via the drive linkage 600 thereby actuating the firing process as described above.

With continued reference to FIGS. 16-21, the assembly 230 also includes the third (e.g., rotating) drive shaft 222a, which may be axially rotatable within the body portion 210. The drive shaft 222a includes a third gear element 552 coupled thereto and configured to rotate therewith about a longitudinal axis defined by the drive shaft 222a. The gear element 552 is meshingly engaged with a second transfer gear element 554. The gear element 554 is held in position by the pin 505 and is configured to rotate about the pin 505.

Figure 23:
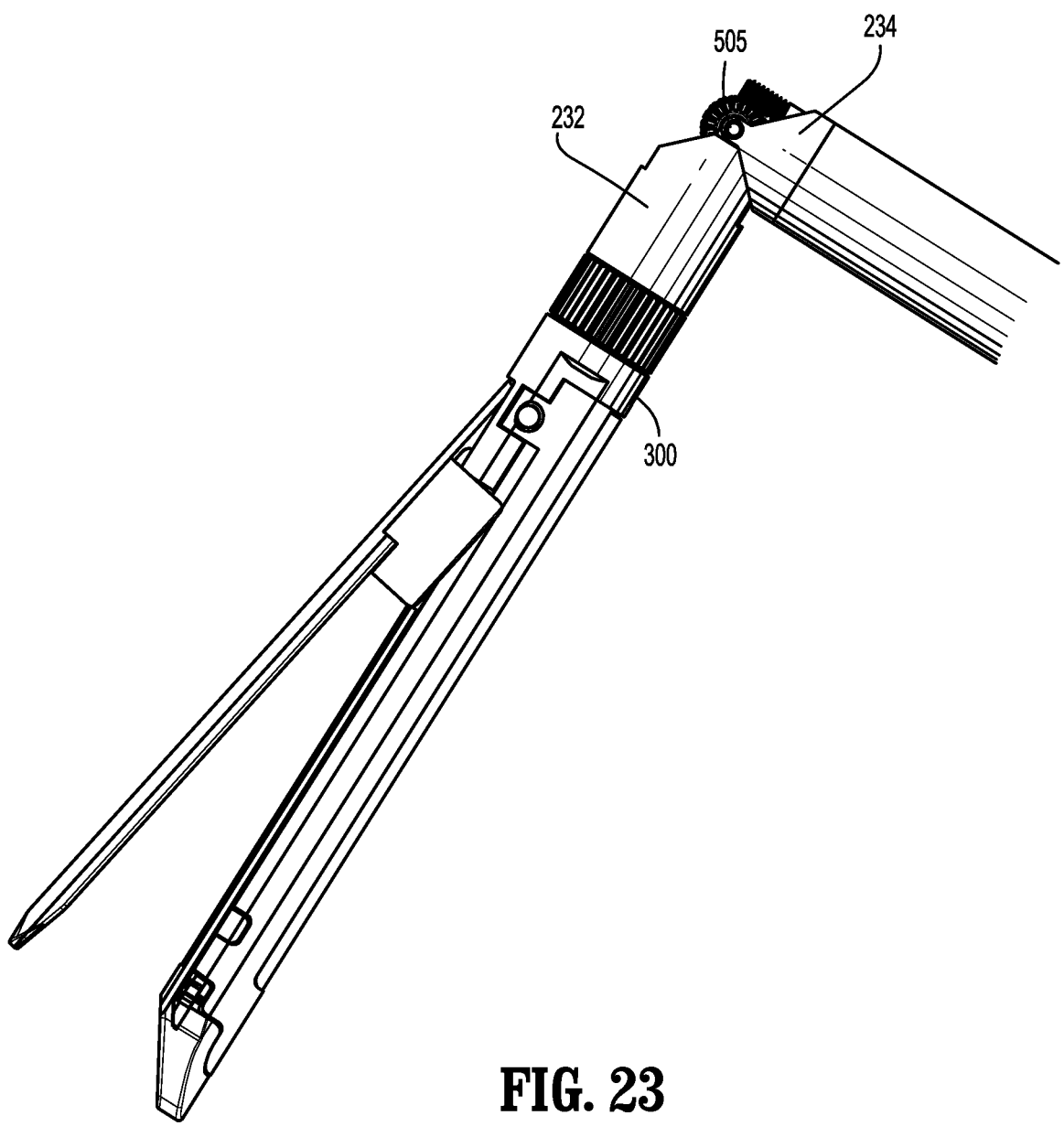
FIG. 23 is a side view of the articulating neck assembly in an articulated orientation, according to the present disclosure.

The gear element 554 is also meshingly engaged with a gear element 556 within the joint member 232. The gear elements 552, 554, 556 are bevel gears allowing for meshing engagement thereof even as the joint member 232 and the end effector 300 are pivoted with respect to the body portion 210. The gear element 552 rotates about a longitudinal axis parallel with the axis "A-A." The gear element 554 rotates about the axis "B-B" and the gear element 556 rotates about a longitudinal axis parallel with the axis "C-C." Use of the bevel gears, namely, the gear elements 502, 504, 506, 552, 554, 556, allows for tightest possible 90° bend angle of the joint member 232 during articulation with respect to the body portion 210 of the adapter assembly 200 as shown in FIG. 23, which shows the joint member 232 pivoted with respect to the joint member 234.

With continued reference to FIGS. 16-21, the gear element 556 is connected to a gear element 560 by a shaft 558. The gear element 556, the gear element 560, and the shaft 558 rotate within the joint member 232 about a longitudinal axis defined by the central axis of the shaft 558. The gear element 560 is, in turn, meshingly engaged with a gear element 562, which is fixedly coupled to the shaft 513, such that rotation of the gear element 562 results in rotation of the shaft 513. As described above, the socket 580 is securely coupled to the shaft 513, such that as the shaft 513 is rotated in either clockwise or counterclockwise direction about the longitudinal axis "C-C" the socket 580 is also rotated in the same direction. Since the end effector 300 is engaged with the socket 580 as described above, the end effector 300 is similarly rotated by the shaft 513. The end effector 300 is configured to rotate about its own longitudinal axis in this manner.

The present disclosure also provides for a rotation lockout assembly 700 for preventing rotation of the end effector 300 during firing. This allows for prevention of tissue damage due to the torque generated during the firing process which would otherwise backfeed the gears within the neck assembly 230 and inadvertently rotate the end effector.

With reference to FIGS. 13, 15, and 17A, the housing 410 may include a distal portion 427a and a proximal portion 427b interconnected by a bolt 429 with the bore 423a (FIG. 13) defined therethrough. The shaft 513 disposed within the joint member 232 includes a bore 423b (FIG. 17A) defined therethrough. The bores 423a and 423b are in longitudinal alignment.

With reference to FIGS. 15-17A, the lockout assembly 700 includes a push rod 702 disposed within the bore 423a and a locking member 704 disposed within the joint member 232. The locking member 704 includes a rod 706 disposed within the bore 423b. The distal end of the rod 706 is in contact with a proximal end of the push rod 702, such that longitudinal movement of either the push rod 702 or the locking member 704 is translated therebetween. The locking member 704 also includes one or more lock lugs 707 configured and dimensioned to meshingly engage the gear element 562. The locking mechanism 700 also includes a spring 708, which is coupled to the joint member 232 and pushes the locking member 704 in a distal direction.

With reference to FIG. 16, prior to insertion of the end effector 300 into the joint member 232, the locking member 704 is engaged with the lock lug 707 thereof preventing actuation of the coupling member 515. As shown in FIGS. 15 and 18, after insertion of the end effector 300, the drive beam 462 is in its proximal most position since it has not been fired and therefore abuts the distal end of the push rod 702. This moves the push rod 702 proximally, which also moves the locking member 704 in a proximal direction to disengage the lock lug 707 from the teeth of the gear element 562. The disengagement of the locking member 704 allows for rotation of the shaft 513, the socket 580, and in turn, the end effector 300 in either clockwise or counterclockwise direction about the longitudinal axis "C-C."

Figure 24:
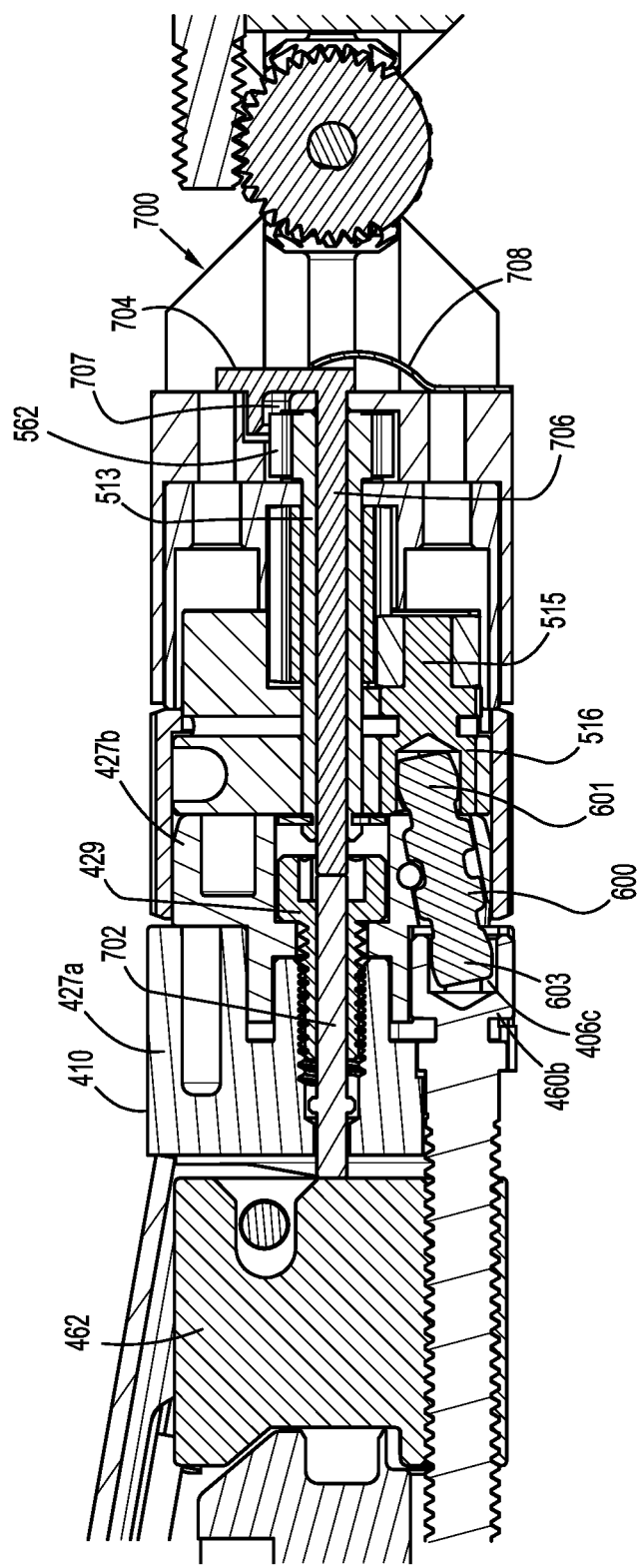
FIG. 24 is an enlarged, cross-sectional side view of the end effector of FIG. 12 connected to the articulating neck assembly, according to the present disclosure.

Once the desired rotational position is achieved firing may be commenced as described above. Firing moves the drive beam 462 distally, which allows the push rod 702 along with the locking member 704 to travel distally due to the biasing forces of the spring 708 as shown in FIG. 24. This moves the lock lug 707 of the locking member 704 into engagement with the gear element 562 preventing rotation of the end effector 300 during the firing process.

With reference to FIGS. 17A, 18 and 25-27, the assembly also includes the first (e.g., pivoting) drive shaft 218a, which may be axially rotatable within the body portion 210. The drive shaft 218a includes a first gear element 570 at its distal end, which is configured as a worm gear. The gear element 570 is meshingly engaged with a pivoting gear element 572, which is configured as a worm wheel drive. The gear element 572 includes a bore 574a therethrough having a facet 574b. The gear element 572 is disposed between the gear elements 504, 554 and is secured to the pin 505 about the bore 574a via mating of the facet 505a of the pin 505 with the facet 574b of bore 574a of gear element 572 in a keyed relationship. Thus, the gear element 572 is secured to the pin 505 along with the joint member 232, which allows for rotation of the joint member 232 along with the end effector 300 with respect to the body portion 210 about the articulation axis "B-B" defined by the pin 505 as described in further detail below.

Figure 25:
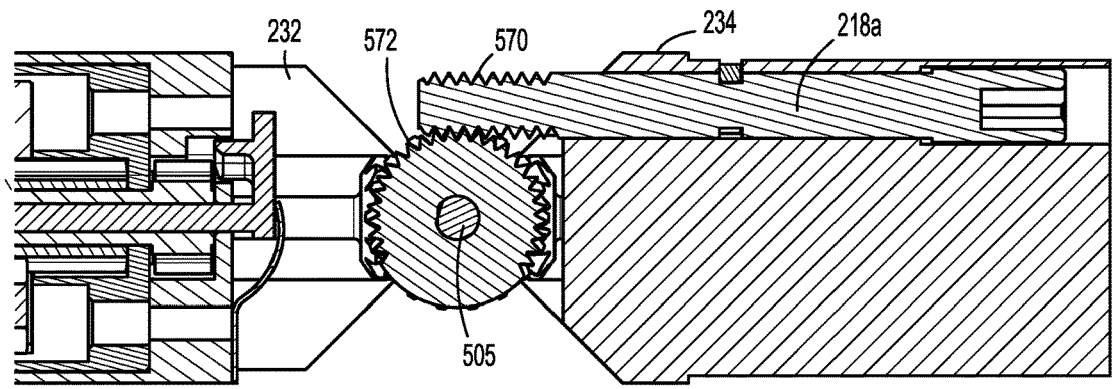
FIG. 25 is a cross-sectional side view of the end effector of FIG. 12 connected to the articulating neck assembly oriented in a linear, non-articulated orientation, according to the present disclosure.
Figure 26:
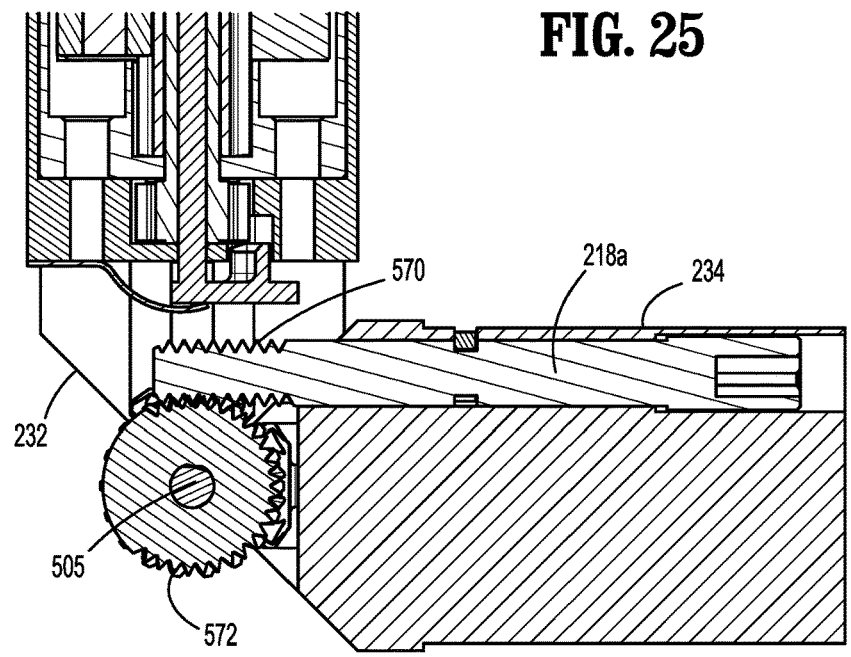
FIG. 26 is a cross-sectional side view of the end effector of FIG. 12 connected to the articulating neck assembly oriented in a first articulated orientation, according to the present disclosure.
Figure 27:
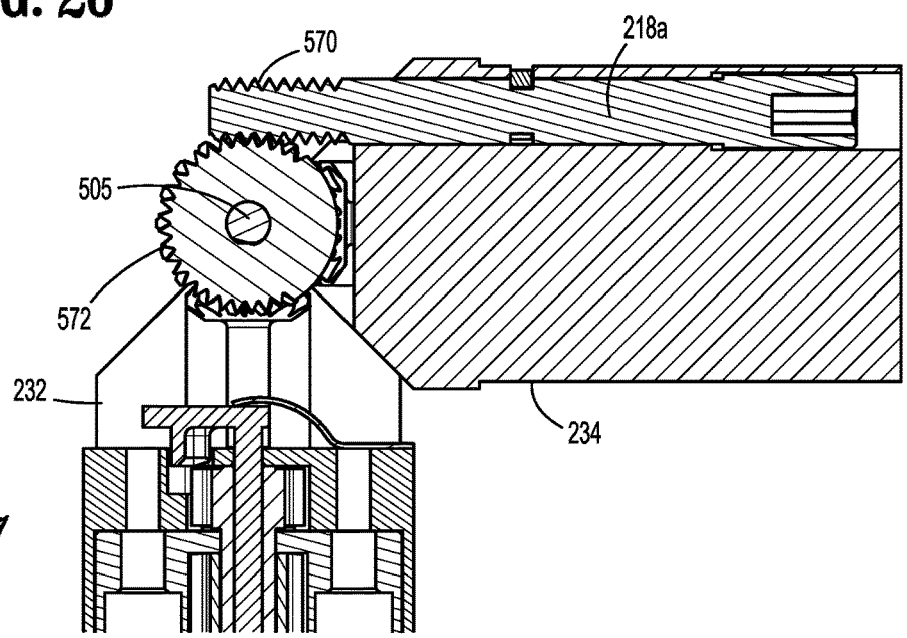
FIG. 27 is a cross-sectional side view of the end effector of FIG. 12 connected to the articulating neck assembly oriented in a second articulated orientation, according to the present disclosure.

As shown in FIGS. 25-27, articulation of the joint member 232 about the articulation axis "B-B" is imparted by rotation of the drive shaft 218a about its longitudinal axis and simultaneous longitudinal movement of the drive shaft 218a along its longitudinal axis, which in turn, rotates the gear element 572 via the gear element 570. Simultaneous rotational and longitudinal movement of the drive shaft 218a may be accomplished via a complementary worm gear mechanism at its proximal end. Since the gear element 572 is securely coupled to the pin 505, rotation of the gear element 572 rotates the pin 505 and the joint member 232, which is also securely coupled thereto as described above. The drive shaft 218a includes a thrust plate 218b that acts as a stop member preventing longitudinal movement of the drive shaft 218a beyond a certain point, which in turn, prevents rotation of the joint member 232 and the end effector 300 beyond a desired stopping point. In embodiments, the joint member 232 may be rotated about the articulation axis "B-B" up to about 300°, with about 150° in either direction from the first aligned position in which the second longitudinal axis "C-C" is substantially aligned with the first longitudinal axis "A-A." In further embodiments, the joint member 232 may be rotated about the articulation axis "B-B" up to about 180°, with about 90° in either direction from the first aligned position.

The gearing relationship between the gear elements 570 and 572 allows for precise pivoting of the end effector 300 with respect to the adapter assembly 200. In addition, the gear elements 570 and 572 provide for a gearing reduction due to a worm gear/worm wheel drive relationship, thereby obviating the need for additional gear reduction mechanisms at the proximal end of the adapter assembly 200.

Figure 28:
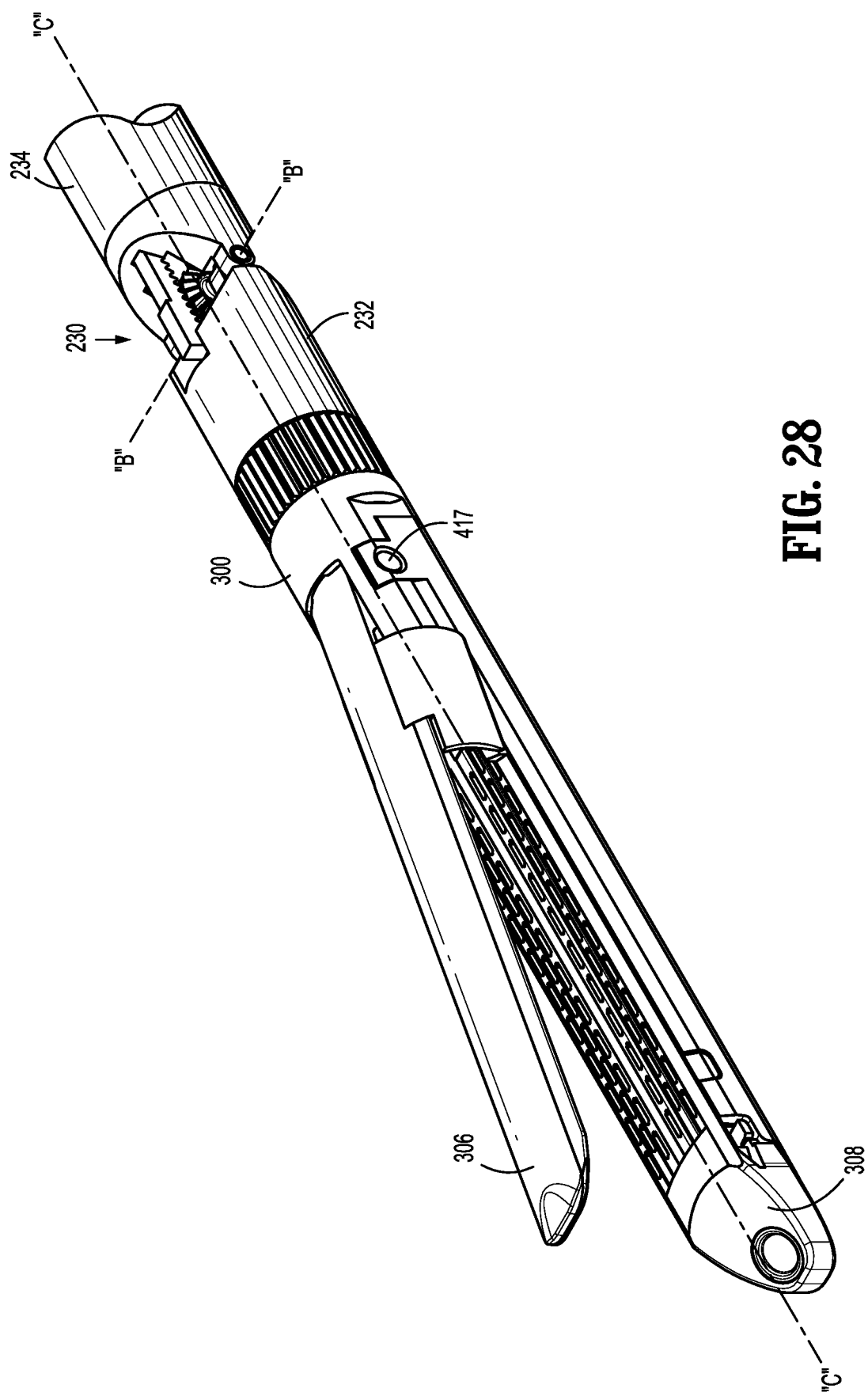
FIG. 28 is a perspective view of another embodiment of an articulating neck assembly with an end effector connected to a distal end of the adapter assembly of FIG. 1, oriented in a linear, non-articulated orientation, according to the present disclosure.
Figure 29:
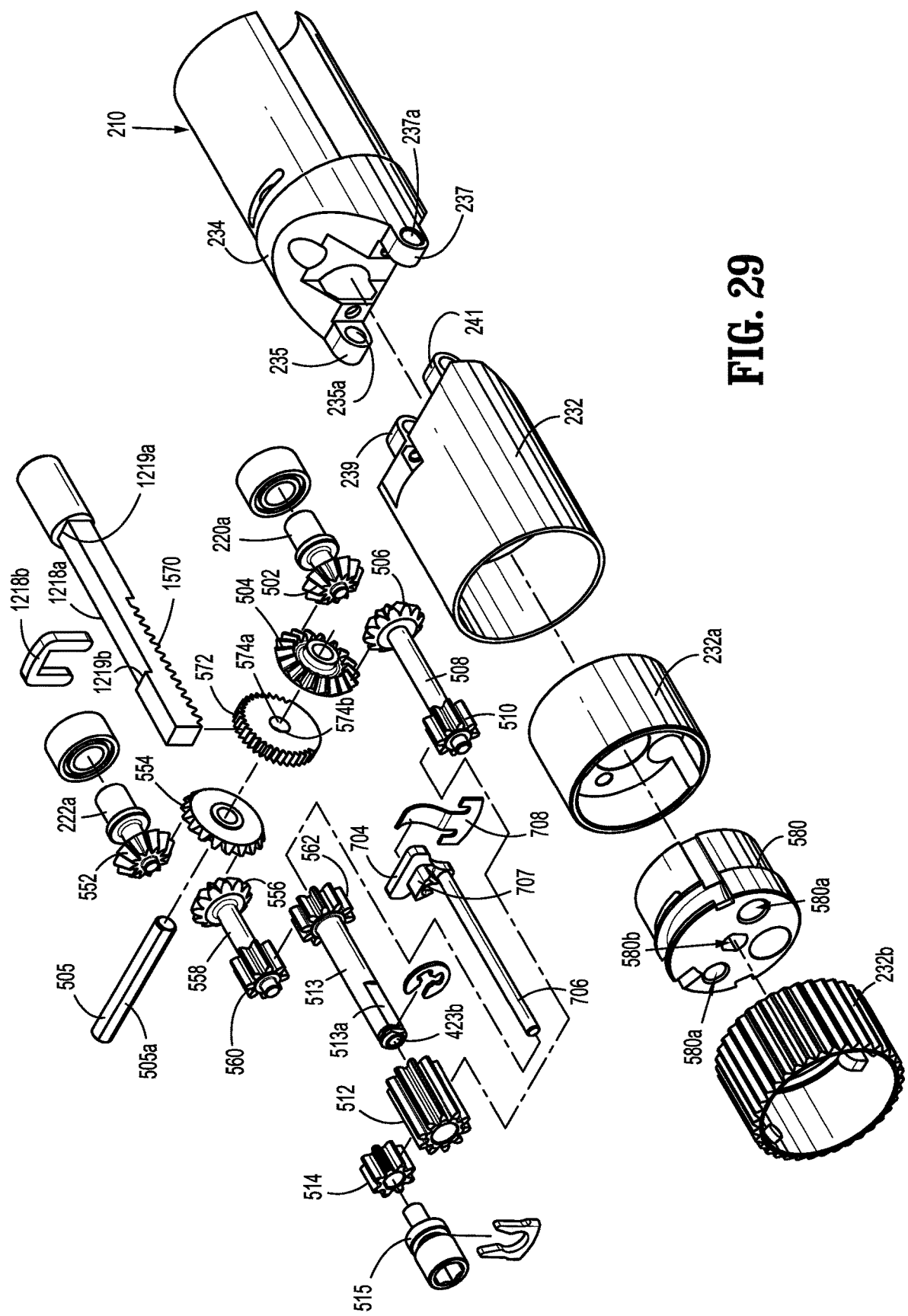
FIG. 29 is a perspective, disassembled view of the articulating neck assembly of FIG. 28 according to the present disclosure.
Figure 30:
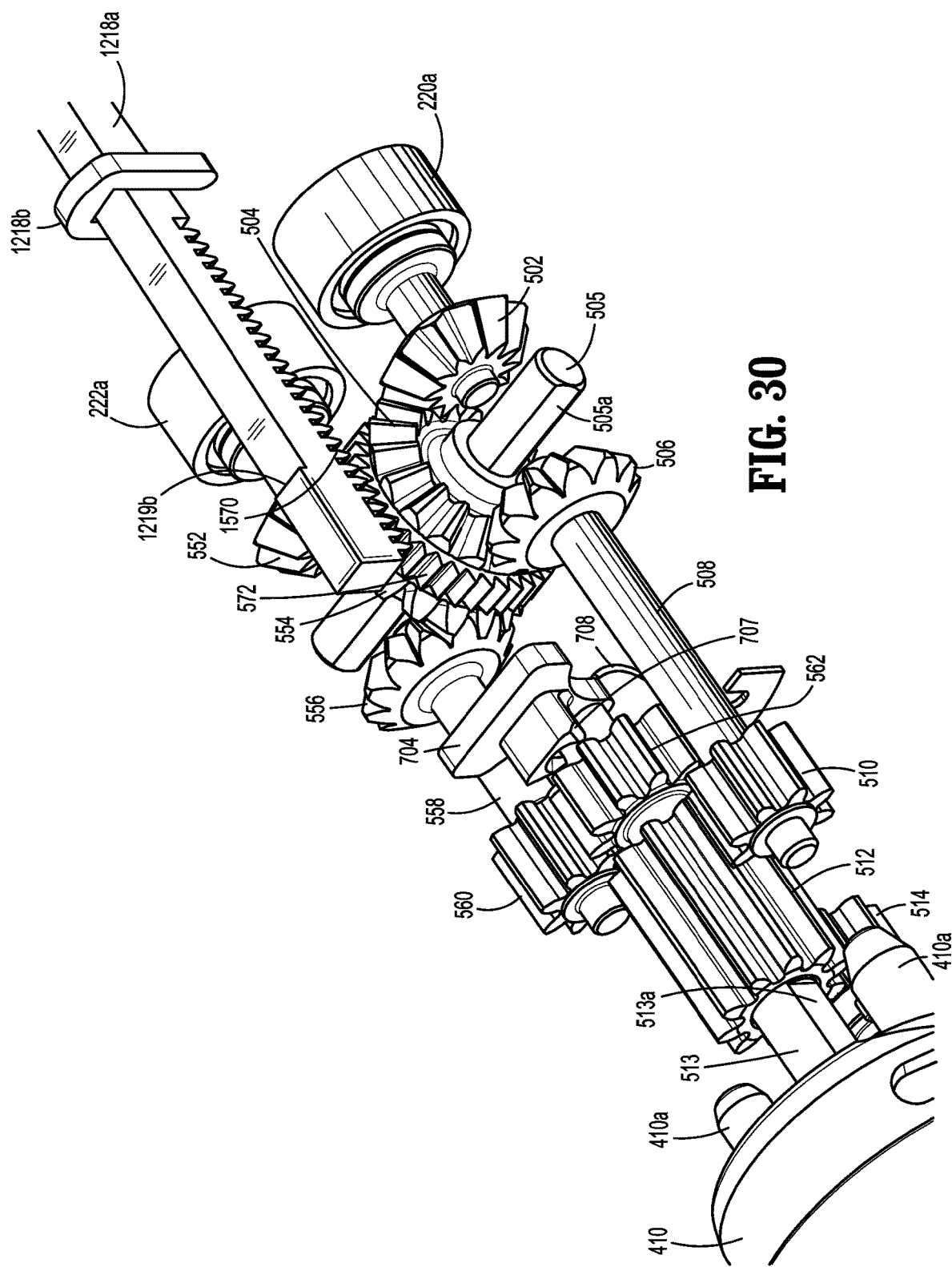
FIG. 30 is a top perspective, partially-disassembled view of the articulating neck assembly of FIG. 28 according to the present disclosure.

Referring to FIGS. 28-30, another embodiment of an articulating assembly 1230 provided in accordance with the present disclosure including a longitudinally translating drive shaft 1218a. Articulating assembly 1230 is substantially similar to articulating assembly 230 and includes most of the components of articulating assembly 230, which are not described below to avoid repetition. Drive shaft 1218a is operatively disposed within body portion 210. Drive shaft 1218a includes a first gear element 1570 that engages pivoting gear element 572. In embodiments, gear element 1570 may be configured as a toothed rack that engages pivoting gear element 572 in a rack and pinion relationship, as best illustrated in FIG. 30.

Figure 31:
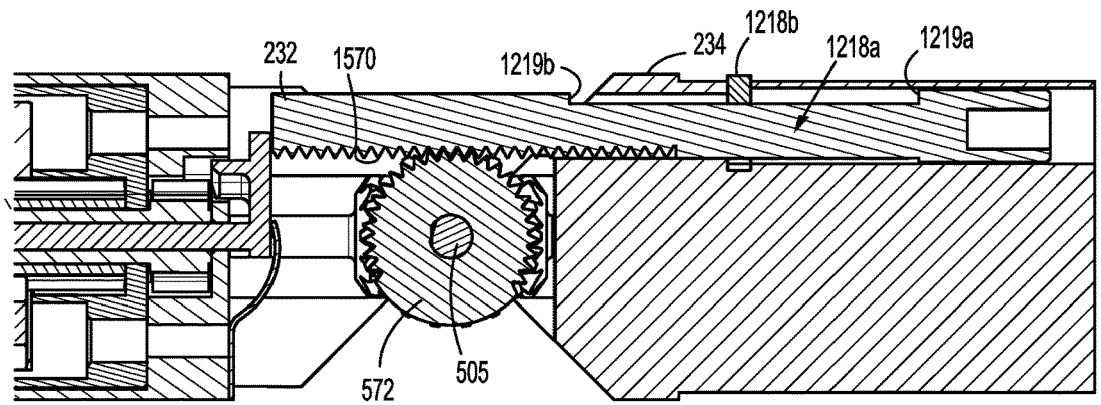
FIG. 31 is a cross-sectional, side view of the end effector connected to the articulating neck assembly of FIG. 28 oriented in a linear, non-articulated orientation, according to the present disclosure.
Figure 32:
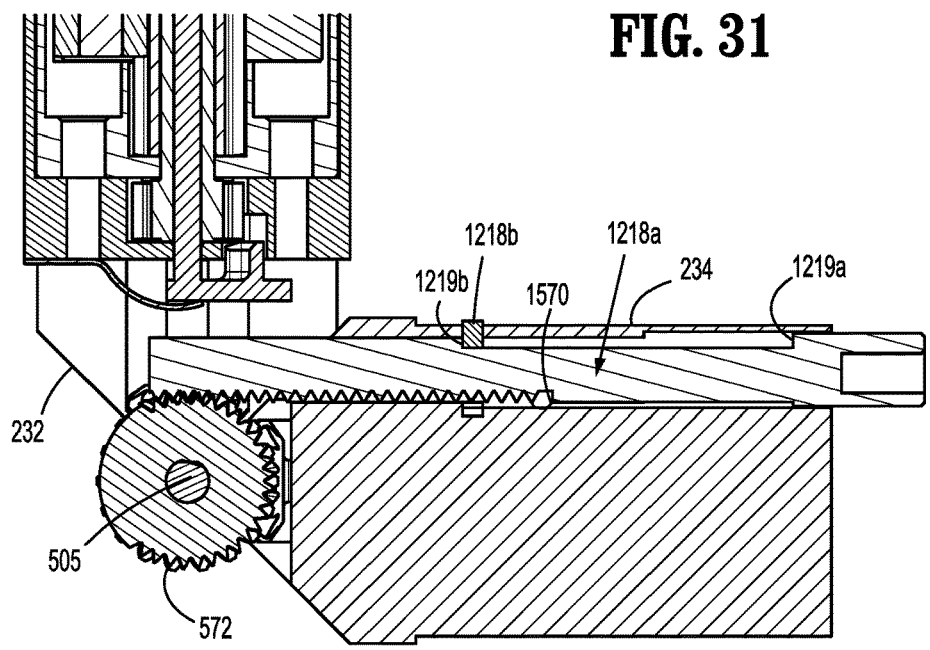
FIG. 32 is a cross-sectional, side view of the end effector connected to the articulating neck assembly of FIG. 28 oriented in a first articulated orientation, according to the present disclosure.
Figure 33:
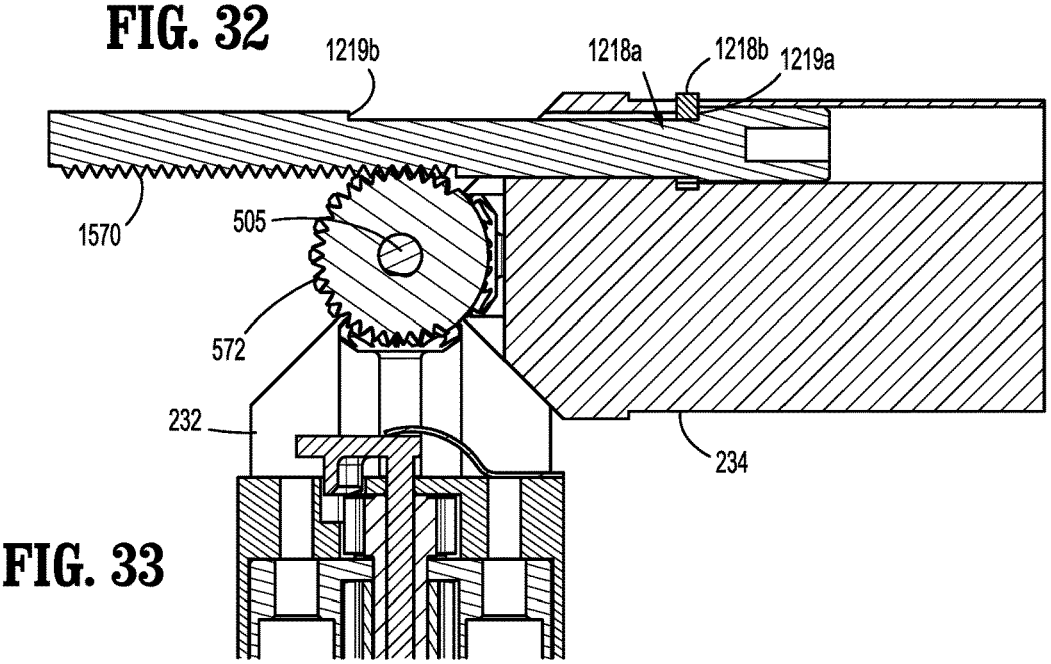
FIG. 33 is a cross-sectional, side view of the end effector connected to the articulating neck assembly of FIG. 28 oriented in a second articulated orientation, according to the present disclosure.

With reference to FIGS. 31-33, articulation of joint member 232 about articulation axis "B-B" (FIG. 28) is imparted by longitudinal translation of drive shaft 1218a along its longitudinal axis, which is parallel to the longitudinal axis "A-A" (FIG. 10). Longitudinal movement of drive shaft 1218a, in turn, rotates pivoting gear element 572 via first gear element 1570. The longitudinal translation of drive shaft 1218a may be accomplished via a drive mechanism described above with respect to drive shaft 218a. First gear element 1570 may extend along drive shaft 1218a such that a portion of first gear element 1570 is adjacent a proximal end of drive shaft 1218a. Since pivoting gear element 572 is securely coupled to pin 505, rotation of pivoting gear element 572 rotates pin 505 and joint member 232, which is also securely coupled thereto as described above.

Drive shaft 1218a also includes a thrust plate 1218b that acts as a stop member preventing longitudinal translation of drive shaft 1218a beyond certain limits (e.g., a proximal limit 1219a or a distal limit 1219b), which in turn, prevents rotation of joint member 232 and end effector 300 beyond a desired point. In embodiments, joint member 232 may be pivoted about the articulation axis "B-B" to a first and second pivoted positions in either direction from a first aligned position in which the second longitudinal axis "C-C" (FIG. 28) is substantially aligned with the first longitudinal axis "A-A" (FIG. 10). The first and second pivoted positions may be up to about 300°, with about 150° of pivot in either direction from the first aligned position. In further embodiments, joint member 232 may be pivoted about the articulation axis "B-B" up to about 180°, with about 90° of pivot in either direction from the first aligned position.

The gearing relationship between gear elements 1570 and 572 allows for precise pivoting of end effector 300 with respect to adapter assembly 200. In addition, the interaction of gear elements 1570 and 572 may provide for a back drive mechanism that permits external forces exerted on an end effector attached to articulating neck assembly 1230 about the pivot axis to back drive the motor until a solid stop is reached (i.e., thrust plate 1218b reaching proximal or distal limit 1219a, 1219b). The solid stop may correspond to the first or second rotated positions of end effector 300. The back drive mechanism may also include a force multiplier configured to reduce the force exerted on the motor by the back drive mechanism. The force multiplier may be from about 1 to about 40, in embodiments, from about 5 to about 20.

In the examples discussed above, the hand-held instrument handle housed a removable and replaceable and/or rechargeable battery, as well as a motor and computer and memory components. A removable and replaceable adapter assembly corresponds to one or more end effector configurations, the end effectors being removable and replaceable. For example, an adapter is configured for use with circular stapling reload end effectors in various sizes, and with or without various other features such as suction and irrigation, visualization, etc. Other adapters are available for use with linear surgical stapling reloads come in various sizes, configurations, possibly having other features such as dissection tips and/or pre-loaded surgical buttress material. In the examples above, the handle may be disposable, for single-procedure use, or sterilizable and re-used for a prescribed number of procedures.

Figure 34:
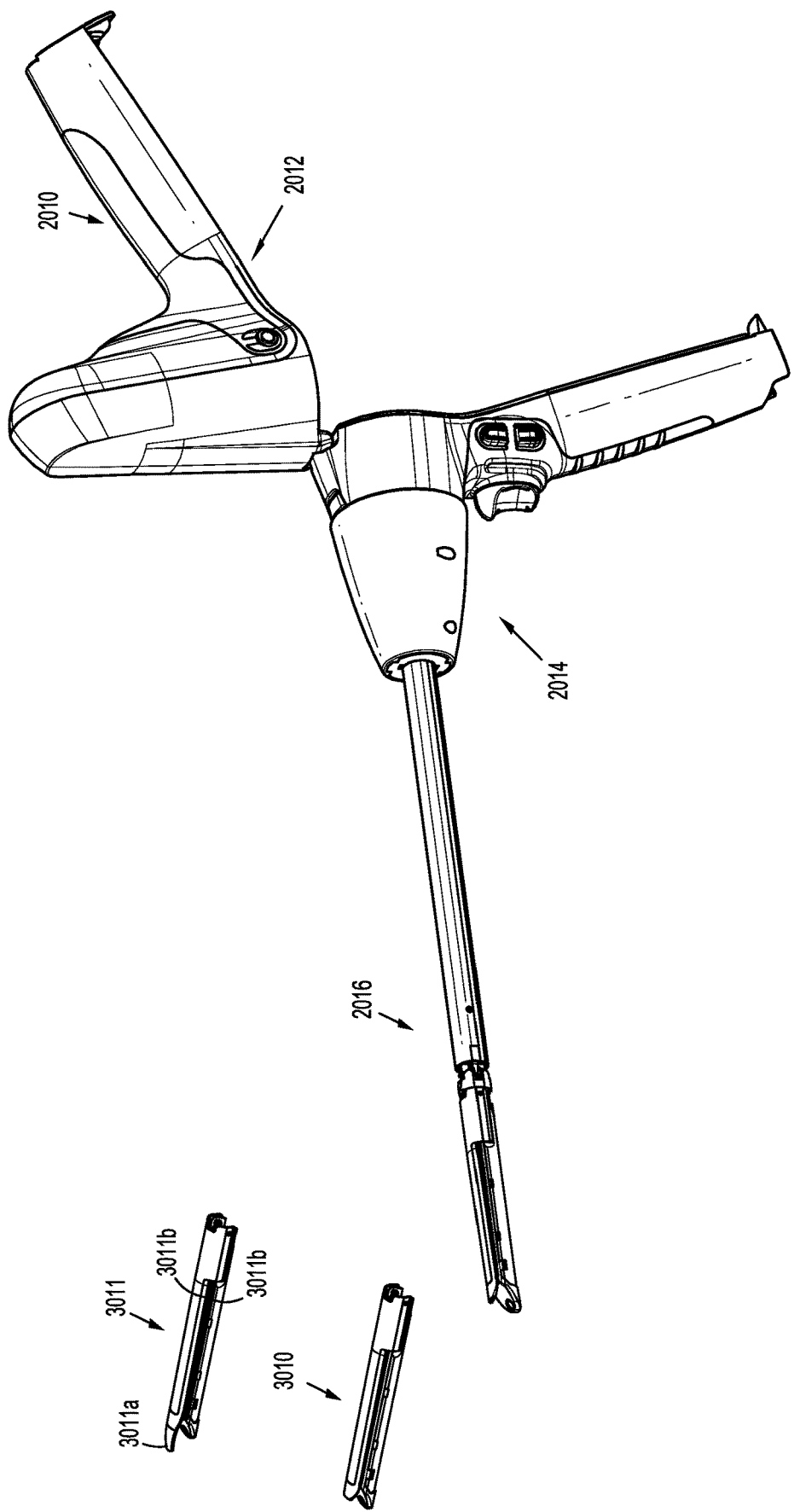
FIG. 34 is a perspective view of a surgical system including a surgical stapling instrument having an adapter assembly, an end effector reload, and a dissecting tip end effector reload according to another aspect of the present disclosure.

In another example shown in FIG. 34, a surgical stapling handle 2010 contains a removable and re-usable motor and battery (not shown), and the handle housing 2012 itself opens and closes to receive those components. This may extend the useful life of the motor, which can be housed in the handle housing in a sealed fashion, avoiding the need to sterilize the motor, the battery, etc. The handle housing 2012 is openable like a shell, as shown and is re-sterilizable. The handle housing carries a series of buttons 2014 and controls for actuating articulation, clamping of tissue, stapling of tissue and cutting of the tissue. These buttons, as well as various indicators (such as lights, screens and the like) can be as discussed above or similar thereto. The controller desirably contains a microprocessor and memory components that record information concerning the use of the instrument and can interact with sensor provided in the other components such as the end effector reload, adapter, staple cartridge assembly, etc.

Figure 34A:
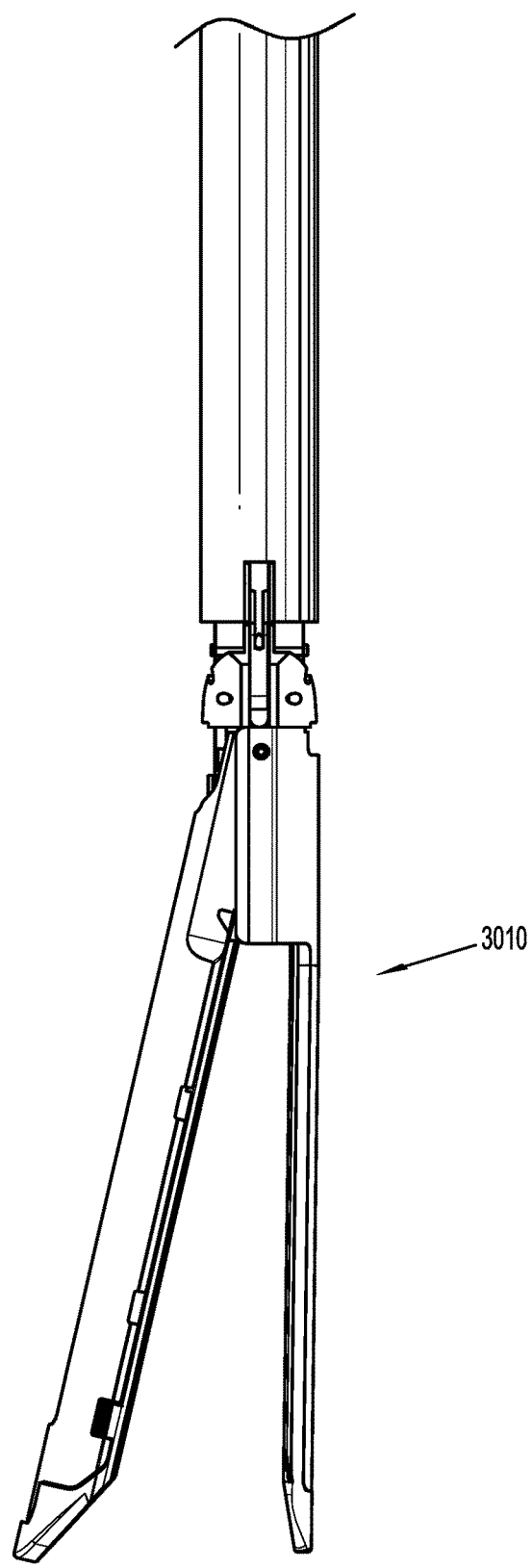
FIG. 34A is an elevation view of the end effector reload and the distal end of the adapter assembly.
Figure 35:
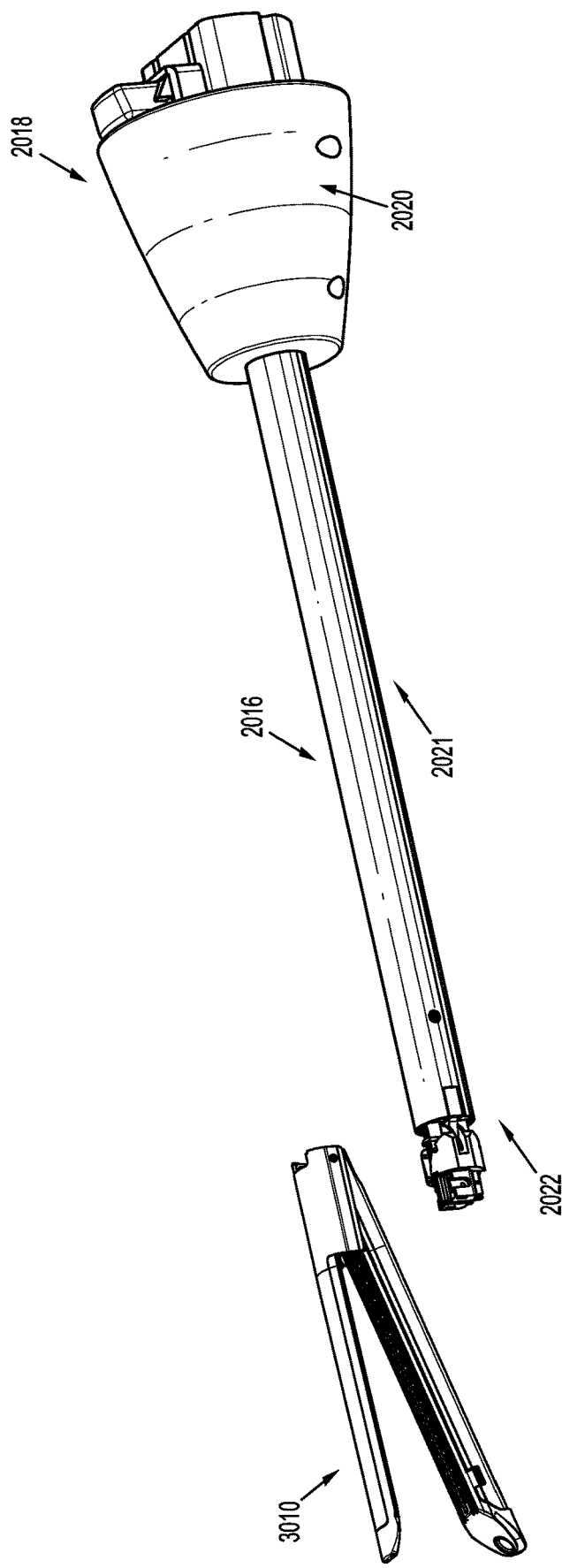
FIG. 35 is a perspective view of an adapter assembly and an end effector reload for the surgical stapling instrument.
Figure 36:
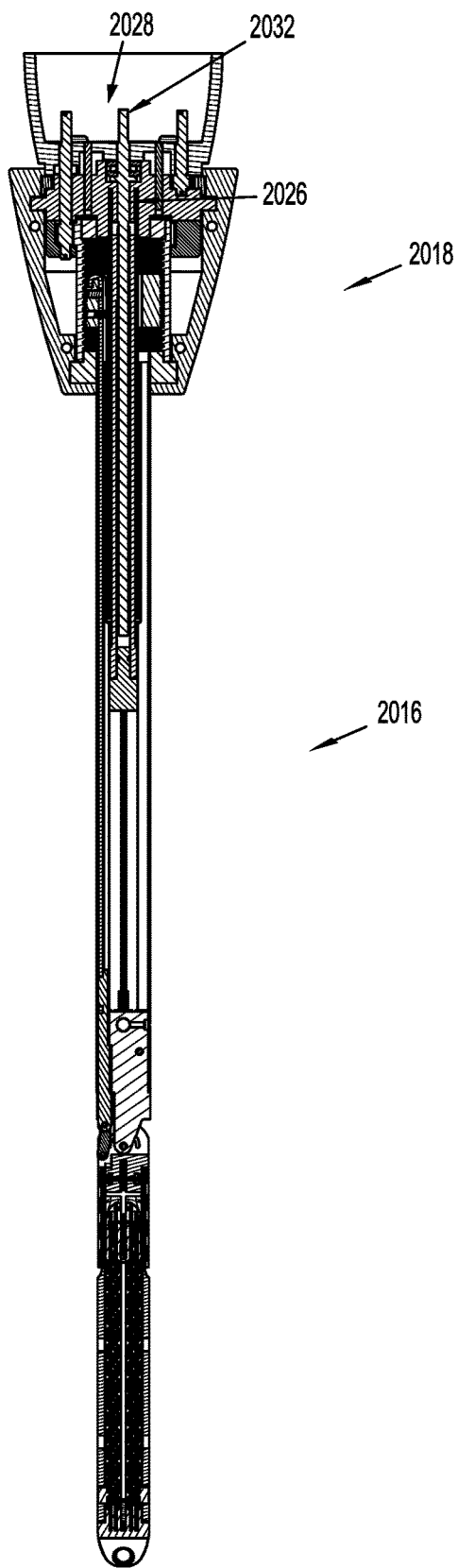
FIG. 36 is a cross-sectional view of the adapter assembly for the surgical stapling instrument of FIGS. 34-35.
Figure 37:
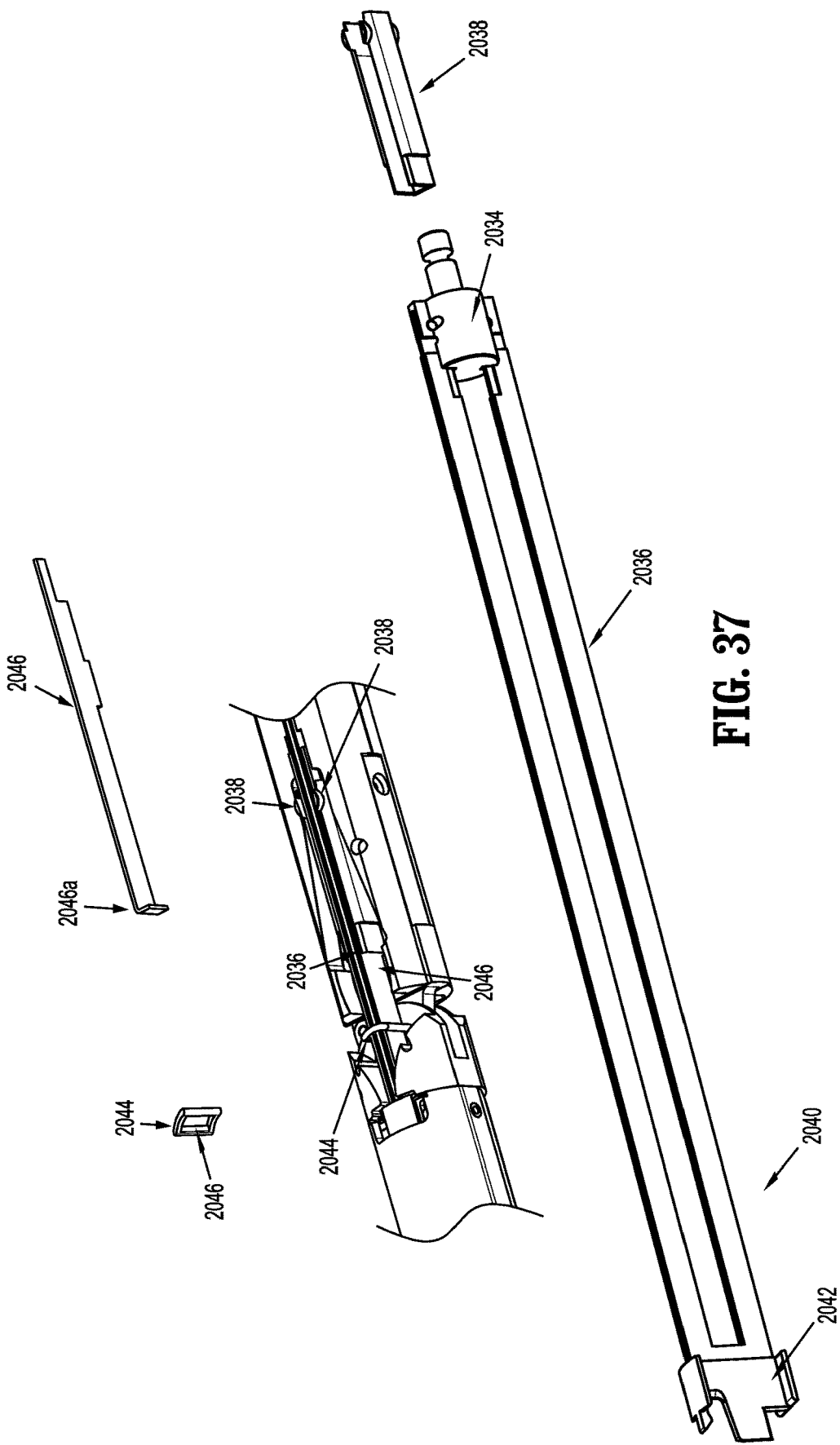
FIG. 37 is a perspective view of the articulating portion of the adapter assembly.
Figure 38:
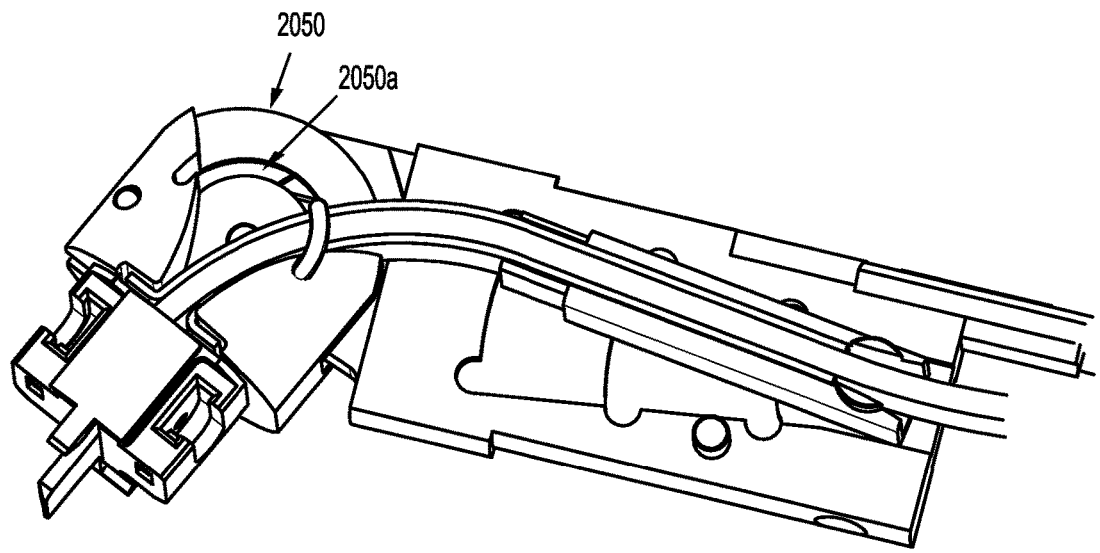
FIG. 38 is a cross-sectional view of the articulating portion of the adapter assembly.
Figure 39:
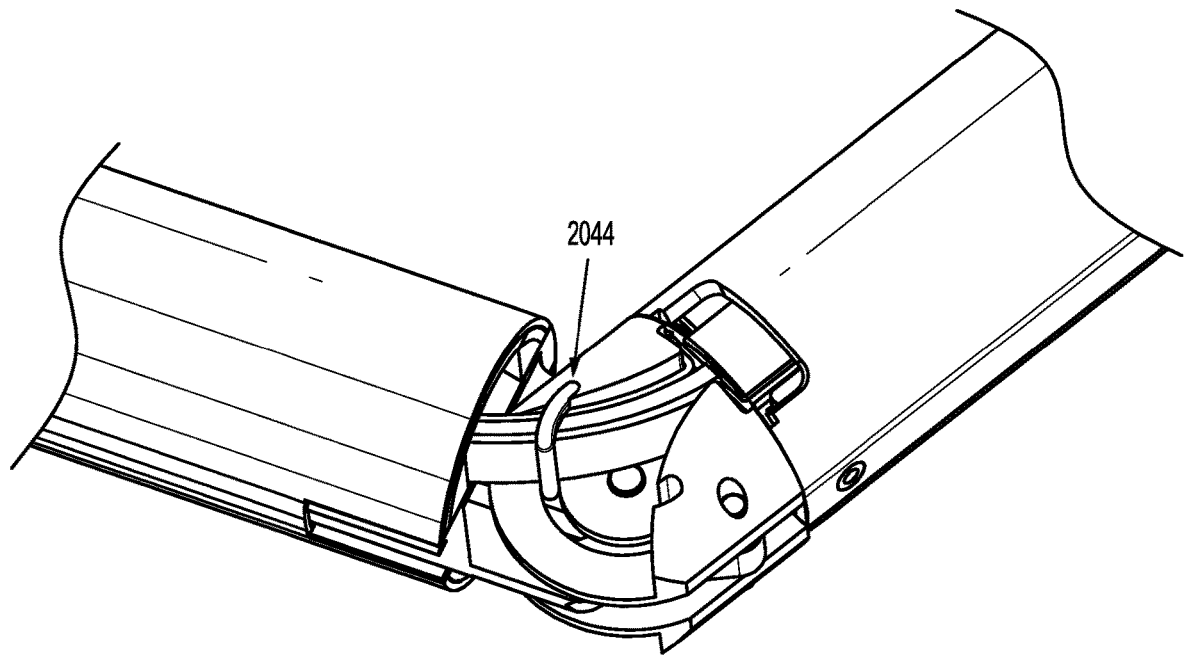
FIG. 39 is a perspective view of the articulating portion of the adapter assembly.

It is contemplated that the adapter assembly 2016 can be removable, as mentioned above, or it can be permanently attached to the handle. The adapter assembly includes a drive mechanism which has mechanical components for manipulating the end effector (FIG. 34A), such as articulation, opening and closing of jaws, etc. As shown in FIG. 35, the adapter assembly 2016 has a proximal end 2018 with a knob 2020, and a distal end 2022 that can be attached to a surgical stapling end effector reload 3010. The proximal end 2018 has a lead screw 2026 with a proximal end 2028 that is accessible at the proximal end 2018 of the adapter assembly 2016. An inner tube 2030 is threadably engaged with (i.e., it has helical grooves) the lead screw, which also has helical threads so that rotation of the lead screw 2026 will translate the inner tube 2030 in a proximal or distal direction. There is a thrust bearing 2032 (FIG. 36) at the proximal end of the lead screw so that it is mounted in the knob 2020. A pusher 2034 is attached to the distal end 2026a of the lead screw and is connected to a bar 2036 through a pin, screw, or the like. The inner tube 2030, thrust bearing 2032, and pusher 2034 can also be seen in FIGS. 39A and 39B The adapter assembly has a drive mechanism inside an elongate shaft that articulates. As shown in FIG. 37, the distal end 2022 of the adapter assembly 2016 has a pair of bar guides 2038, one each on either side of a bar 2036, and adjacent to the bar guides is a pair of blowout plates 2046 that are next to the bar guides, but distal to them. The bar itself is made of a plurality of layers, or stainless steel or equivalent material, that are stacked against one another. At a distal end 2040 of the bar, a beam is attached to the bar. The beam shown is an I-beam 2042 having an upper flange 2042a and a lower flange 2042b is attached. The bar is further supported by a support block 2044 that has an opening 2046 so that it surrounds the bar, and the blowout plates 2046. The support block is curved in shape, with the convex side of the support block facing proximally, and is made of a strong material like stainless steel. As seen in FIG. 37, the blowout plates each have a distal end 2046a that form a flange 2048 for being received in a slot in a mounting member 2050. The mounting member 2050 forms the distal end of the adapter assembly 2016 and can be attached to the end effector reload. The mounting member 2050 also has an arcuate slot 2050a for receiving and supporting the support block 2044, and also allowing the support block 2044 to move so that the assembly (the bar, blowout plates, support block) move off-center with respect to the adapter assembly when the end effector reload is articulated and pivoted with respect to the adapter (See FIG. 38). In such movement, the bar guides 2038 are moved as well. (See FIG. 39). The bar, the pair of bar guides, the pair of blowout plates, and the support block are pivotable from a central position in the adapter assembly to an off-center position in the adapter assembly.

When the device is articulated, the distal ends of the bar guides pivot off-center, supporting the blowout plates and the plurality of layers forming the bar. When the guides pivot off-center, it creates a large radius for the bar to be driven through, reducing stress on the bar, and the layers making up the bar. The bar guides are separate members, but they pivot together. The assembly works in the same way when articulated in the opposite direction.

Figure 39A:
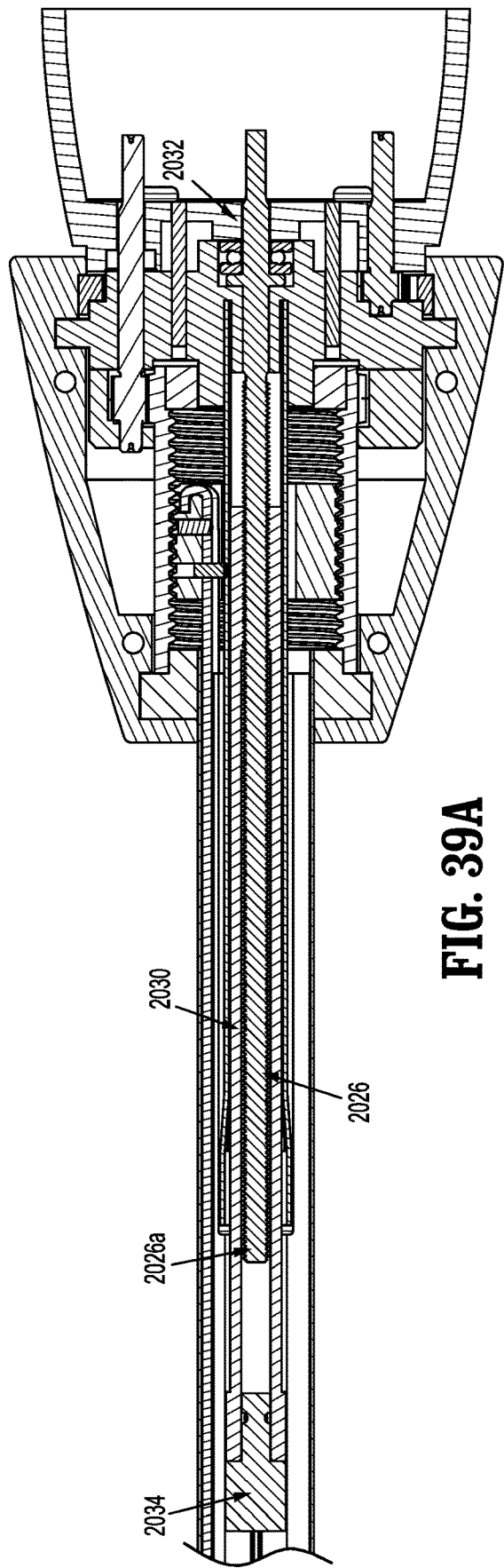
FIG. 39A is a cross-sectional view of the proximal end of the adapter assembly.
Figure 39B:
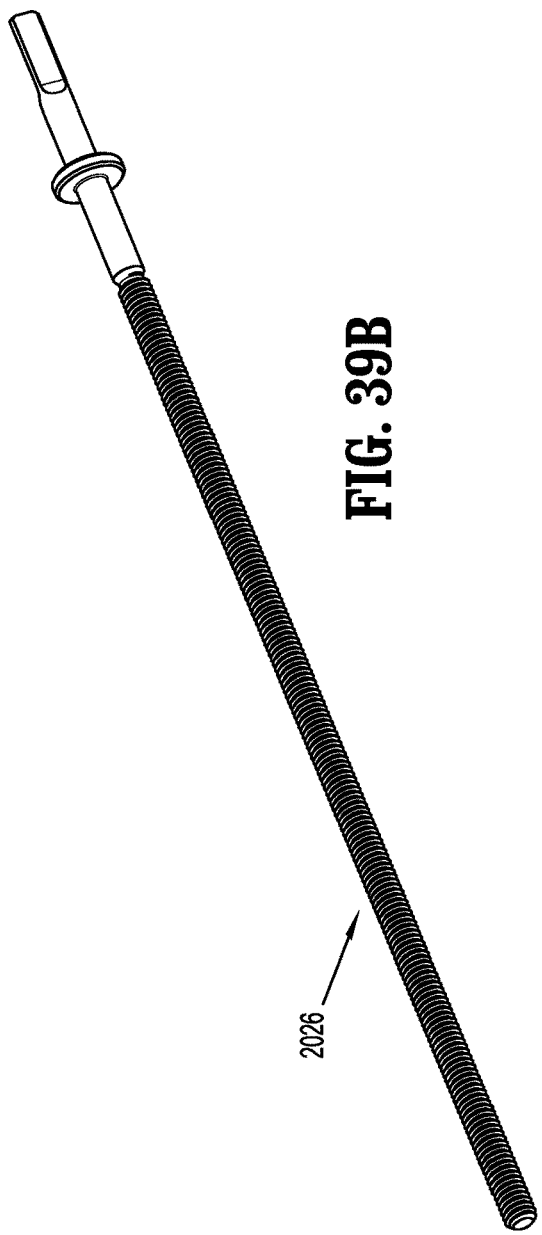
FIG. 39B is a perspective view of the lead screw of the adapter assembly.
Figure 46:
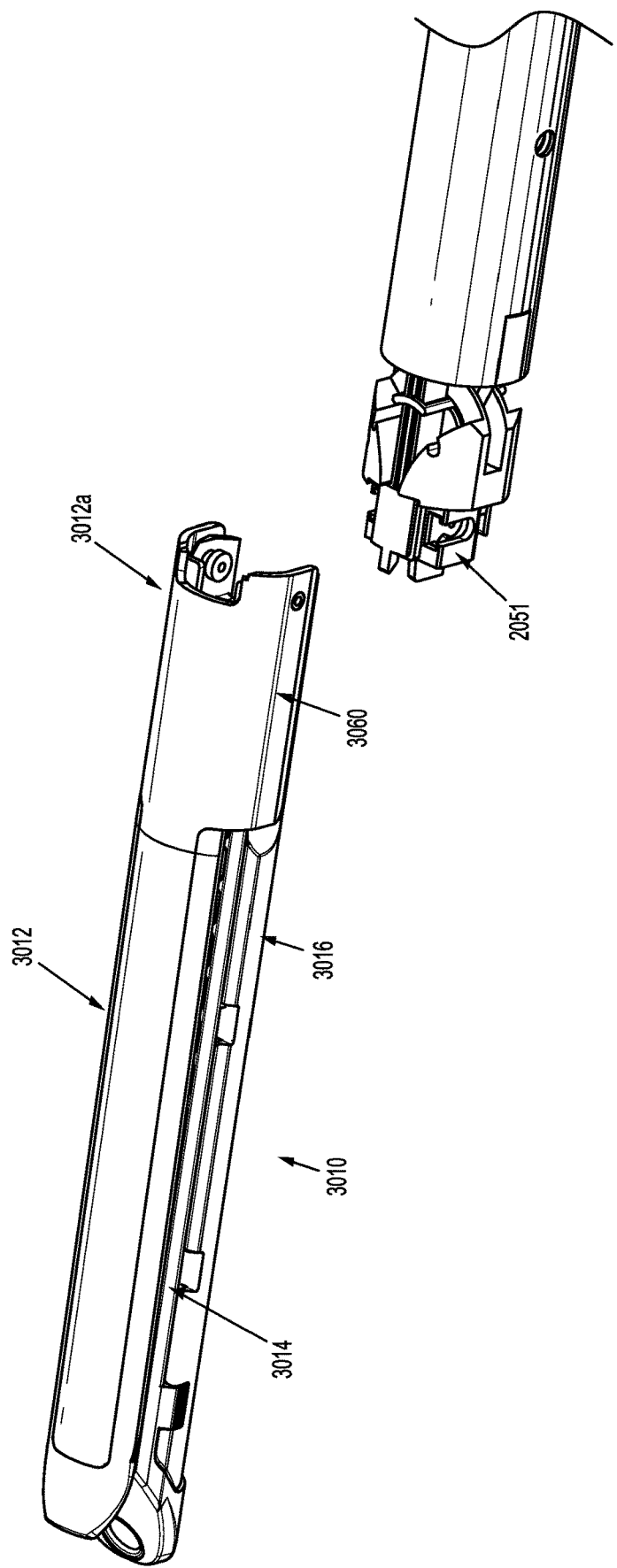
FIG. 46 is a perspective view of the end effector reload and distal end of the adapter assembly.

I-beam 2042 and bar 2036 are moved by the inner tube 2030 in a distal direction to effect the closing of the end effector jaw members onto tissue, and to fire staples and cut tissue. (FIGS. 39A and 39B). The end effector reload 3010 has an anvil assembly 3012, a cartridge assembly 3014, and a channel 3016 for receiving the cartridge assembly. The entire end effector reload 3010 can be attached to the adapter assembly 2016, and removed and replaced after use. (FIG. 46). Another end effector 3010 can be re-attached, and/or a different end effector, such as a dissecting tip end effector reload 3011, for example, can be attached to adapter assembly 2016 as seen in FIG. 34. Briefly, end effector 3011 is similar to end effector 3010 but includes a dissecting tip 3011a and buttresses 3011b supported thereon. The anvil assembly 3012 can be one or more parts machined and/or welded together, and having an anvil plate 3012a with recesses shaped for forming the staples into a closed shape when they are driven against the anvil plate 3012a. The staple cartridge assembly 3014 is attached to the channel 3016 and has an upper surface with slots (also seen in FIG. 50) that house the unformed staples and allow their ejection from the cartridge assembly 3014 and into tissue.

Figure 40:
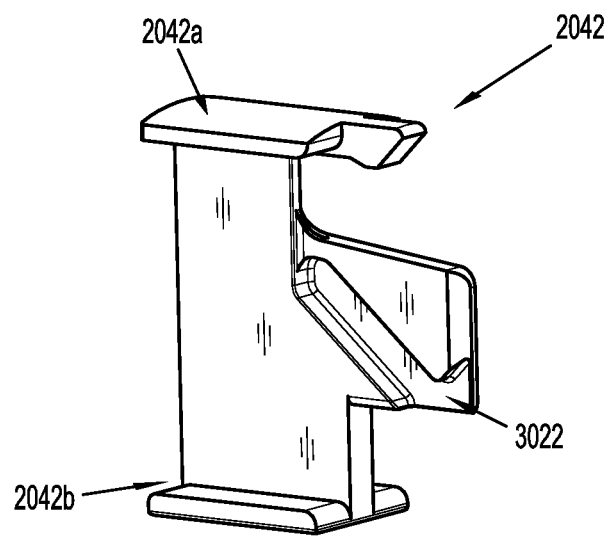
FIG. 40 is a perspective view of an I-beam for the surgical stapling instrument.
Figure 40A:
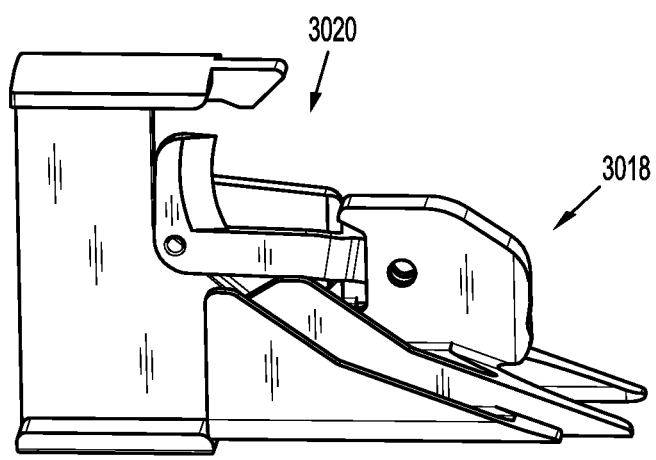
FIG. 40A is a perspective view of the I-beam and sled for the surgical stapling instrument.
Figure 40B:
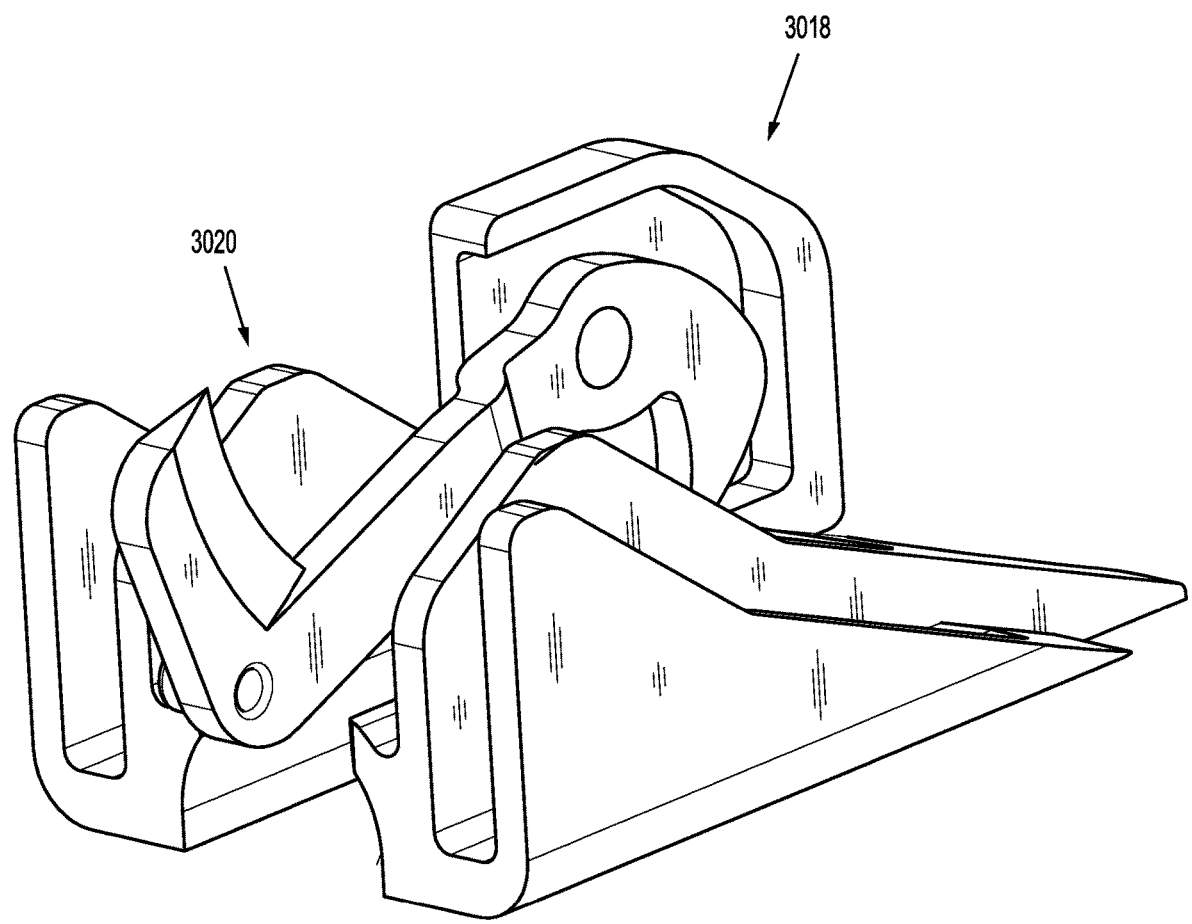
FIG. 40B is a perspective view of the I-beam and sled for the surgical stapling instrument.

The anvil assembly 3012, staple cartridge assembly 3014, and channel 3016 have slots that allow the passage of the I-beam 2042 and bar 2036. The layers of the bar 2036 are dimensioned so that they extend into both the slot in the anvil assembly 3012 and the slot in the channel 3016. The staple cartridge assembly 3014 has a sled 3018 that carries a knife 3020 rotartably supported on the sled. The knife can be biased in an upward position for cutting tissue, or it can be biased in a downward position where it does not access tissue, and/or the knife 3020 can be moved by a feature on the I-beam 2042. As shown in FIG. 40, the feature of the I-beam can be a slot 3022 for camming a protrusion 3024 on the knife 3020. When the bar and I-beam are moved distally, the engagement of the flanges 2042a and 2042b of the I-beam with the anvil assembly and channel move the anvil assembly, staple cartridge assembly, and channel into approximation to engage tissue. In further movement distally, the I-beam 2042 pushes the sled 3018 and knife 3020 distally. (FIGS. 40 and 40A). The sled interacts with pushers in the staple cartridge assembly to drive the staples out of the slots. In other examples, the knife can be formed directly on the I-beam 2042.

Figure 41:
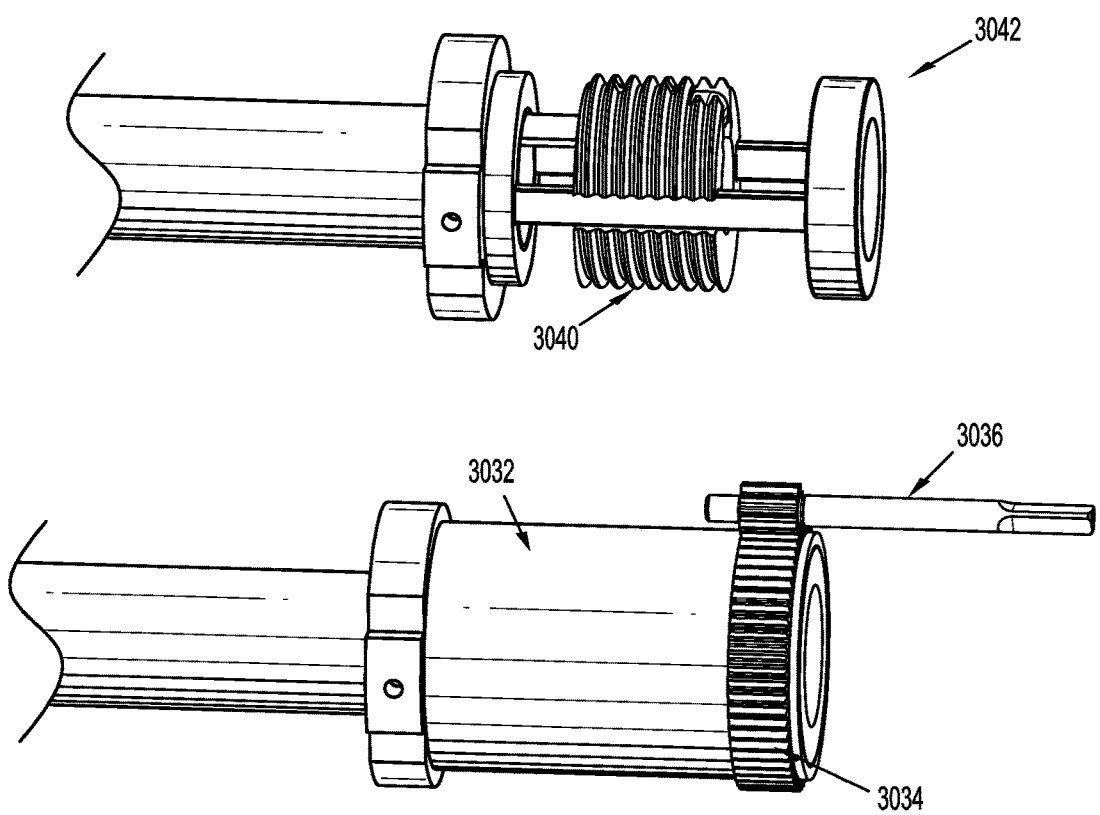
FIG. 41 is a perspective view of the articulation mechanism in the proximal end of the adapter assembly.
Figure 42:
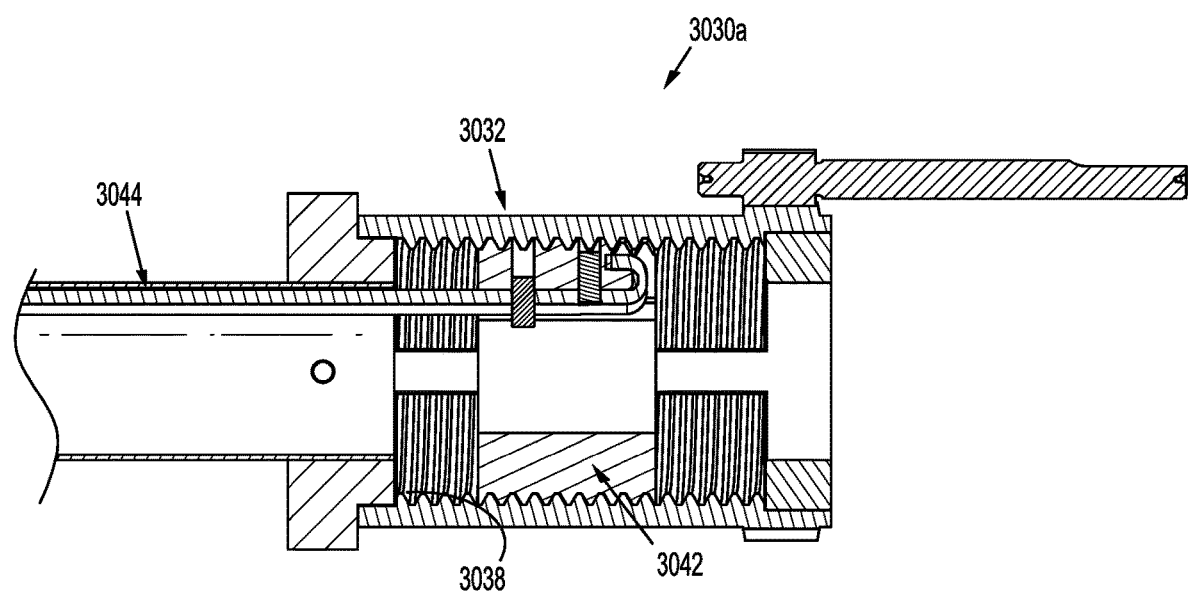
FIG. 42 is a cross-sectional view of the articulation mechanism in the proximal end of the adapter assembly.

The proximal end 3030a of the articulation mechanism 3030 of the adapter assembly 2016 is shown in FIG. 41. A cylindrical articulation nut 3032 having threads on its proximal end 3034. An input shaft 3036 with corresponding threads is enmeshed with the threads of the nut 3032. The rotating shaft 3036 will rotate the nut 3032 through the operation of the threads. The interior of the nut 3032 is hollow and also has a helical groove 3038. The groove 3038 is engaged with a groove 3040 on the outside of a screw 3042 (FIG. 42) disposed inside the nut 3032. When the nut 3032 rotates, the screw moves distally or proximally, to move an articulation link 3044. In this way, distal movement of the link will articulate or pivot the end effector in one direction, and proximal movement of the link 3044 will articulate or pivot the end effector in the other direction.

Figure 43:
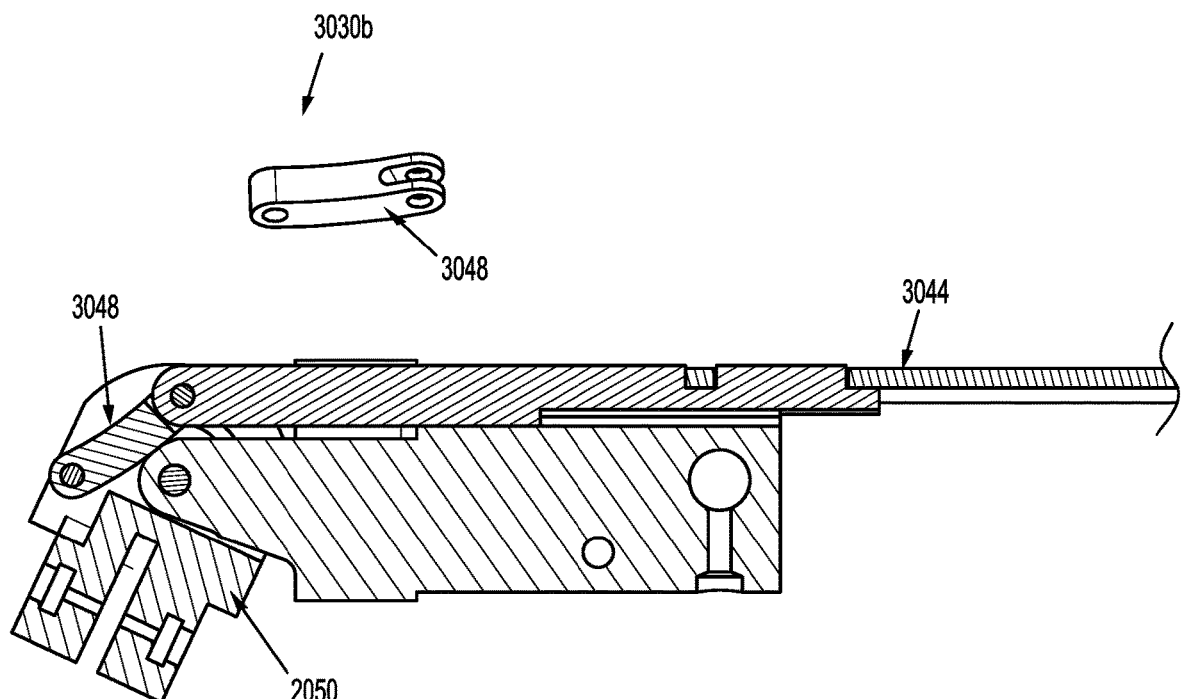
FIG. 43 is a plan view of the articulation mechanism in the distal end of the adapter assembly.
Figure 44:
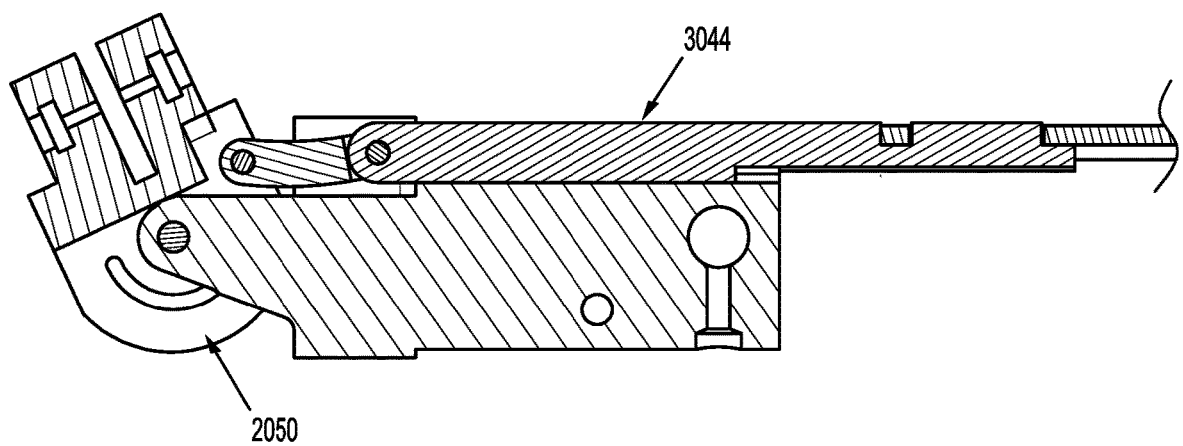
FIG. 44 is a plan view of the articulation mechanism in the distal end of the adapter assembly.

The distal end 3030b of the articulation mechanism 3030 of the adapter assembly 2016 is shown in FIG. 43. The articulation link 3044 ends in a connection to a second link which is a short link 3048, via a pin. The short link is curved and also pinned to the mounting member 2050 at an off-center location. (FIG. 44). The mounting member 2050 is connected to the adapter assembly 2016 at a pin 3050a and the mounting member 2050 pivots about the pin 3050 when the links 3044, 3048 are moved. (See FIGS. 44 and 45).

Figure 45A:
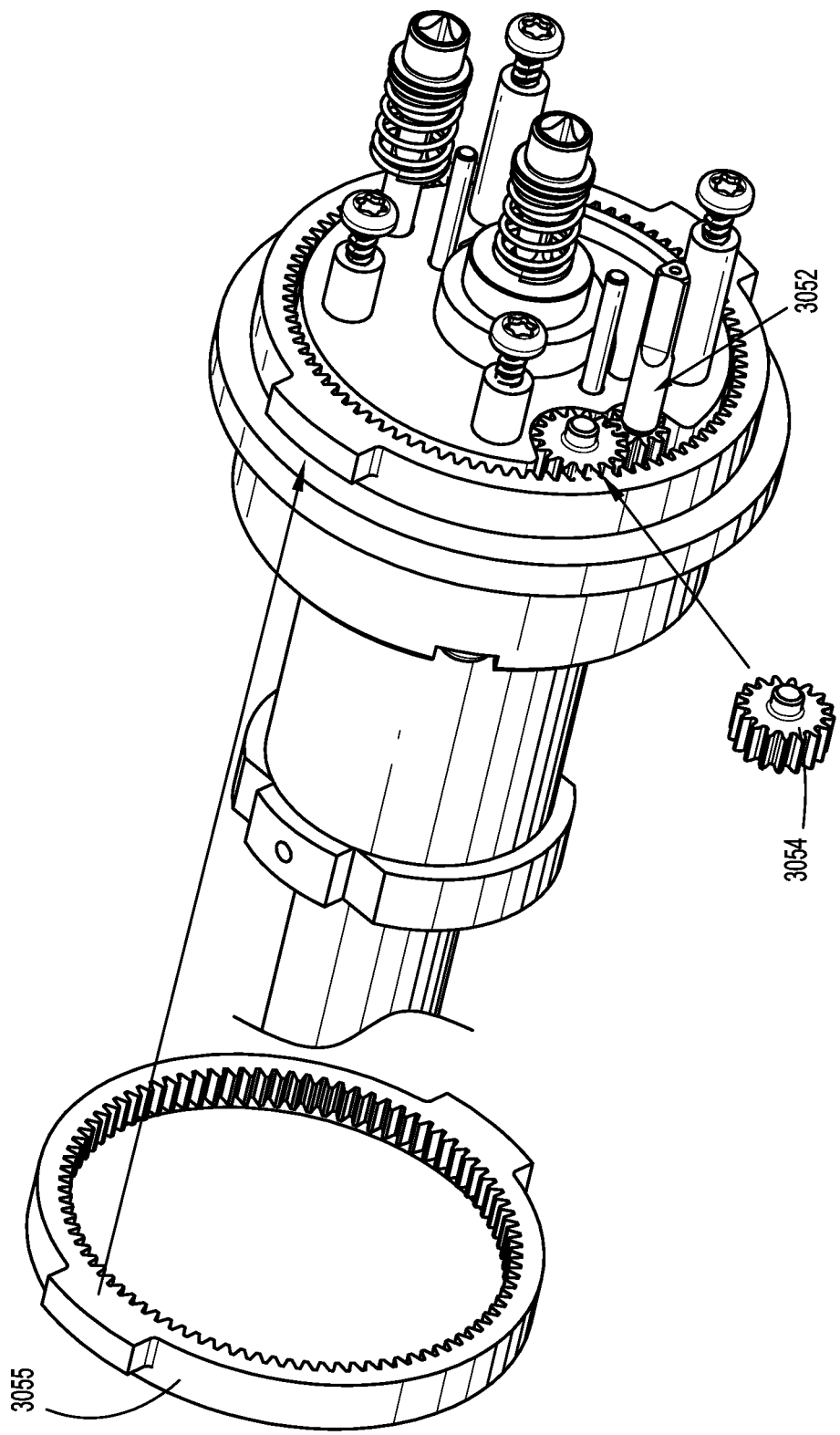
FIG. 45A is a perspective view of a gear assembly in the adapter assembly.

The adapter assembly 2016 proximal end 2018 knob 2020 houses a mechanism for rotating the entire adapter assembly about its own longitudinal axis "A". A rotation input shaft 3052 rotates a gear 3054 that is enmeshed with a ring gear 3055. When the input shaft rotates, it rotates the knob 2020, outer tube 2021, and everything attached to it. (FIG. 45A).

Figure 47:
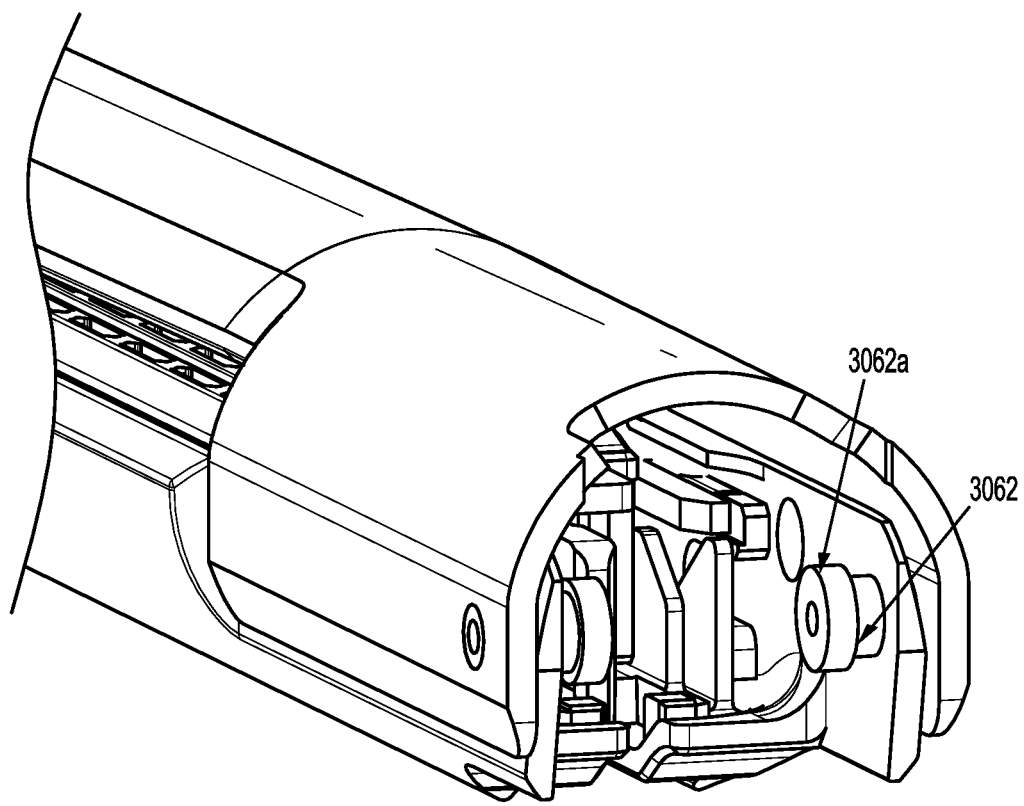
FIG. 47 is a perspective view of the proximal end of the end effector reload.
Figure 48:
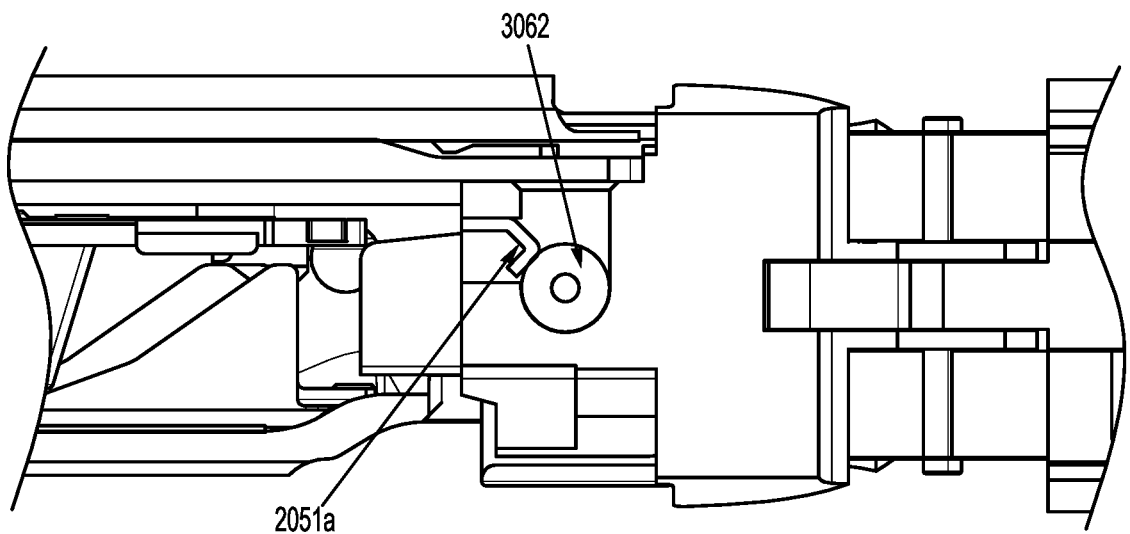
FIG. 48 is a plan view of the end effector reload and distal end of the adapter assembly.
Figure 48A:
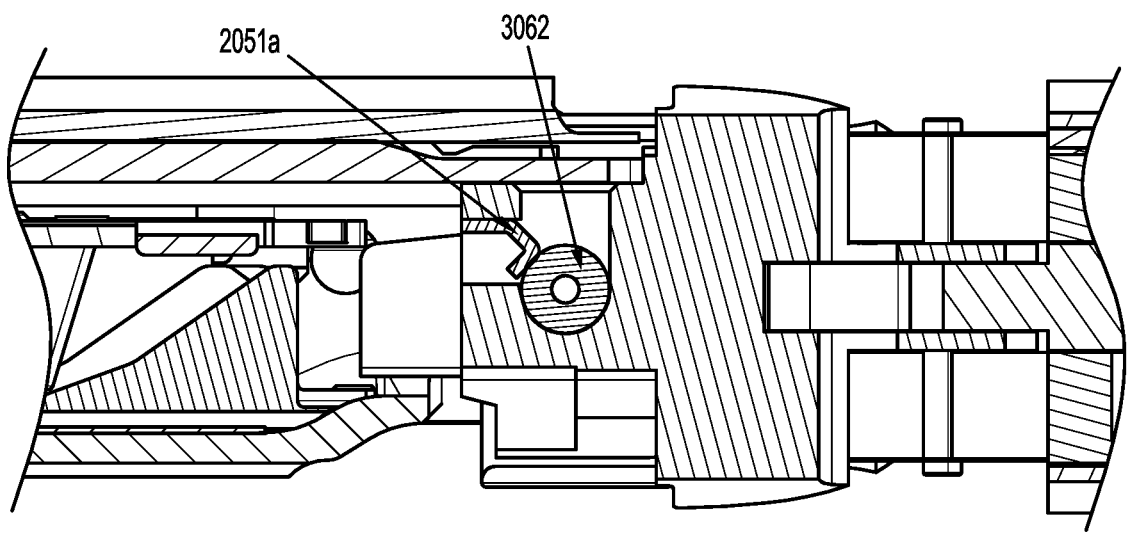
FIG. 48A is a cross-sectional view of the end effector reload and distal end of the adapter assembly.

FIG. 46 shows the attachment of the end effector reload 3010 to the adapter assembly. The anvil assembly 3012 has a semi-cylindrical proximal end 3012a that forms tissue stops 3060. The tissue stops 3060 form walls, one on each side of the reload 3010. On an interior surface of each tissue stop 3060 a locking tab 3062 is defined. The locking tabs each have an extension 3062a that is received in a connection feature of the mounting member. The connection feature of the mounting member is a pair of keyways 2051 defined in the mounting member 2050. (FIGS. 46, 47, 48). The keyways each form a slot that receives the extension 3062a to lock the reload onto the adapter assembly. The keyways slots are upwardly open, so that the end effector reload is locked onto the adapter assembly through movement of the reload downwardly. (FIGS. 47 and 48). Spring fingers 2051a engage the locking tab extensions. (FIG. 48A).

Figure 49:
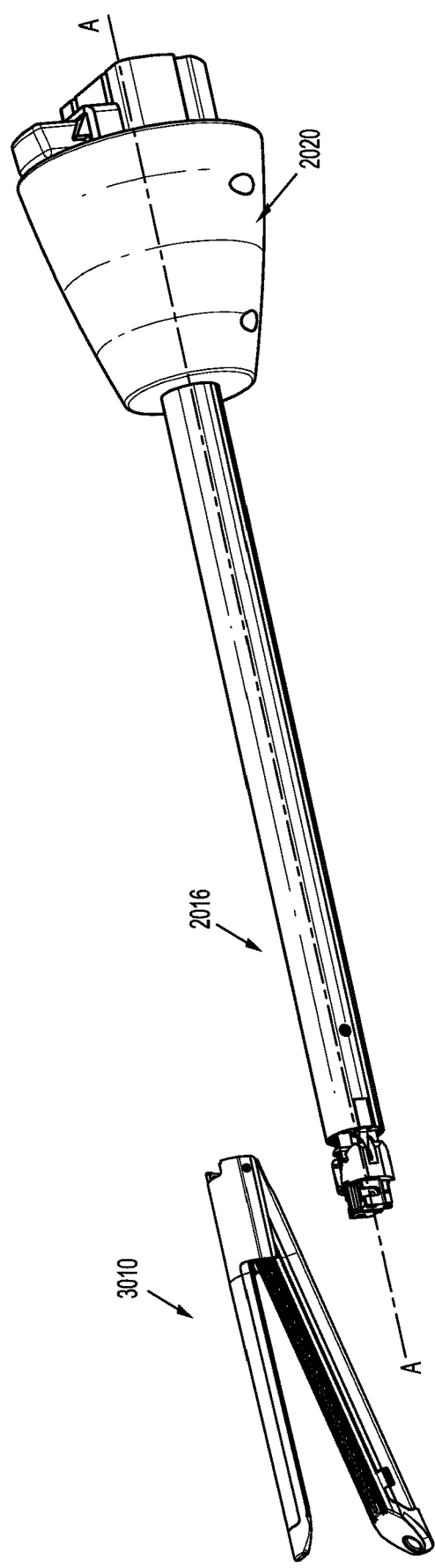
FIG. 49 is a perspective view of the adapter assembly and end effector reload showing the reload unattached to the adapter assembly.
Figure 50:
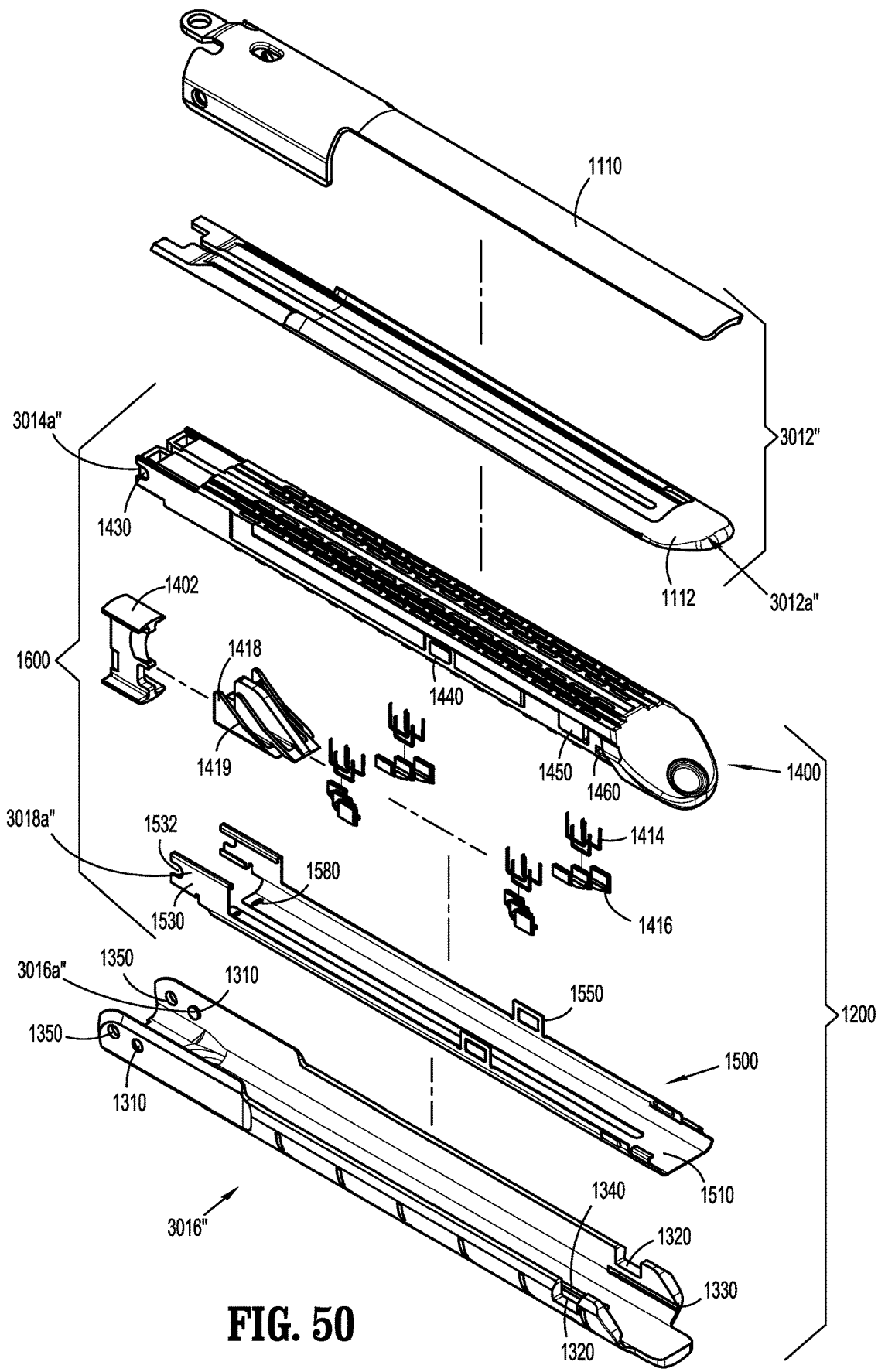
FIG. 50 is an exploded view of the staple cartridge assembly and anvil assembly.

The example described above has a staple cartridge assembly that is not intended to be removed and replaced in the end effector reload 3010. In further examples, the adapter assembly 2016 and end effector reload 3010 are as described above, except that the end effector reload has a removable and replaceable staple cartridge assembly. As shown in FIGS. 49 and 50, the staple cartridge assembly 3014″ has a snap-fit arrangement at its proximal end, formed by a rearwardly facing opening 3014a″ in the staple cartridge body 4015 and a corresponding opening 3018a″ in the support tray. These openings engage a boss 3016a″ in the channel 3016″ in a snap-fit relationship. In this way, the end effector reload, adapter assembly, and stapler handle can be reused to fire another set of staples, without replacing the end effector reload. As the length of the staple lines depends on the selection of the end effector reload, that component must be replaced to change the length of the staple lines formed in tissue. However, the size of the staples, and the arrangement of staples (more than one staple size, or all the same size staples), whether there is a pre-loaded buttress or curved tip or other feature, can be changed by changing the selection of the staple cartridge assembly 3014″. A manually actuated stapler handle, in an instrument having a removable and replaceable staple cartridge assembly, is disclosed in U.S. Pat. No. 9,016,539, the entire disclosure of which is hereby incorporated by reference herein.

Figure 51:
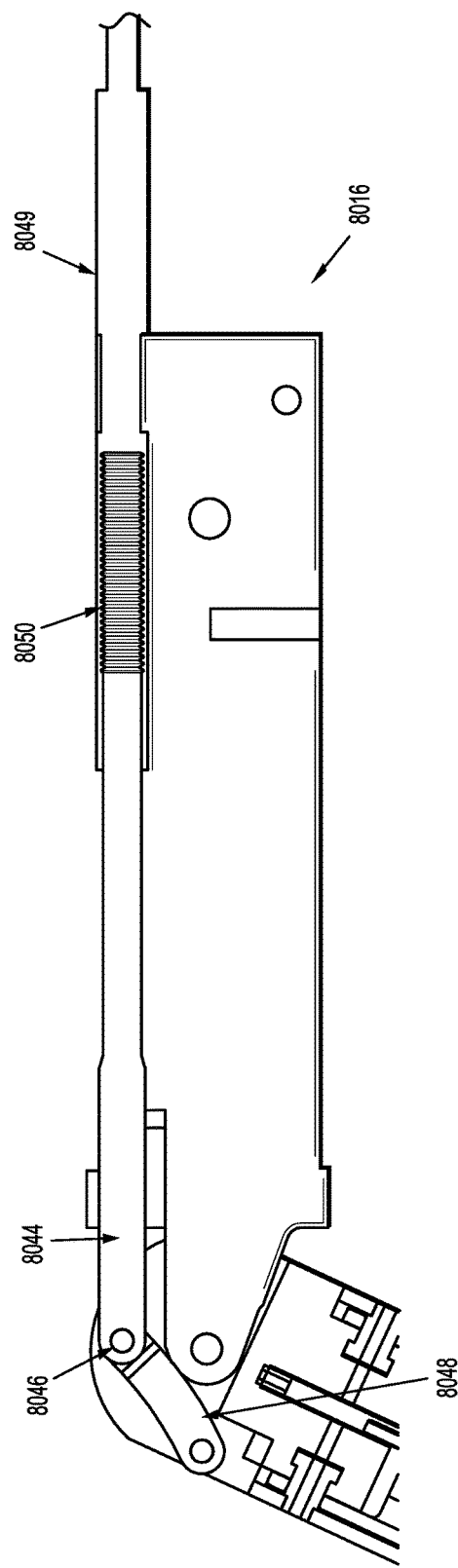
FIG. 51 is a plan view of a different example of an articulation mechanism in the distal end of an adapter assembly.

In a further alternative example of an articulation mechanism in the adapter assembly, FIG. 51 shows an articulation mechanism having a threaded engagement in the distal portion of the adapter assembly 8016. The articulation mechanism is as described above, and has an articulation link 8044, and a short link 8048, connected to one another by a pin 8046. The drive shaft 8049 extends to the distal end of the adapter assembly 8016 and forms a series of threads 8050 on its distal end. The threads 8050 are engaged with threads on the articulation link and are used to translate the articulation link 8044 when the drive shaft 8049 rotates.

It will be understood that various modifications may be made to the embodiments disclosed herein. For example, surgical instrument 100 and/or end effector 300 need not apply staples but rather may apply two part fasteners as is known in the art. Further, the length of the linear row of staples or fasteners may be modified to meet the requirements of a particular surgical procedure. Thus, the length of the linear row of staples and/or fasteners within a staple cartridge assembly may be varied accordingly. Therefore, the above description should not be construed as limiting, but merely as exemplifications of preferred embodiments. Those skilled in the art will envision other modifications within the scope and spirit of the claims appended thereto.

What is claimed:

1. A surgical stapling system comprising:
 a hand-held instrument handle having a battery, a motor and computer and memory components;
 a removable and replaceable adapter assembly extending to a mounting member configured to articulate relative to a remaining portion of the adapter assembly;
 a first linear surgical stapling reload having a first end effector, the first linear surgical stapling reload being removably and replaceably attachable to the mounting member of the adapter assembly;
 a second linear surgical stapling reload having a second end effector and being removably and replaceably attachable to the mounting member of the adapter assembly, each of the first linear surgical stapling reload and the second linear surgical stapling reload having a staple cartridge assembly and an anvil assembly; and
 a drive mechanism that is longitudinally movable in a longitudinal direction through one of the first or second end effectors to fire staples therefrom, wherein when the one of the first or second end effectors articulates relative to the removable and replaceable adapter assembly, the drive mechanism extends through a support block movably seated within an elongated slot defined in the mounting member, the slot including openings defined in a thickness direction of the mounting member, the thickness direction being transverse to the longitudinal direction, the support block extending through at least one of the openings of the elongated slot, the drive mechanism positioned to move laterally across the mounting member between a centered position along the mounting member and an off-centered position along the mounting member.

2. The surgical stapling system according to claim 1, wherein the adapter assembly corresponds to the first linear surgical stapling reload and the second linear surgical stapling reload.

3. The surgical stapling system according to claim 1, wherein the second linear surgical stapling reload includes a dissecting tip on a distal end of the anvil assembly thereof.

4. The surgical stapling system according to claim 1, wherein the second linear surgical stapling reload includes a stapling buttress on each of the anvil assembly and the staple cartridge assembly thereof.

5. The surgical stapling system according to claim 1, wherein the handle is sterilizable and re-used for a prescribed number of procedures.

6. The surgical stapling system according to claim 1, wherein the support block is rectangular.

7. The surgical stapling system according to claim 1, wherein the slot is arcuate.

* * * * *